US007718651B2

(12) United States Patent
White et al.

(10) Patent No.: US 7,718,651 B2
(45) Date of Patent: May 18, 2010

(54) INHIBITORS OF FTSZ AND USES THEREOF

(75) Inventors: E. Lucile White, Birmingham, AL (US); Robert C. Reynolds, Birmingham, AL (US); William J. Suling, Pelham, AL (US)

(73) Assignee: Southern Research Institute, Birmingham, AL (US)

( * ) Notice: Subject to any disclaimer, the term of this patent is extended or adjusted under 35 U.S.C. 154(b) by 889 days.

(21) Appl. No.: 10/519,731

(22) PCT Filed: Jul. 2, 2003

(86) PCT No.: PCT/US03/20984

§ 371 (c)(1),
(2), (4) Date: Jul. 5, 2005

(87) PCT Pub. No.: WO2004/005472

PCT Pub. Date: Jan. 15, 2004

(65) Prior Publication Data

US 2006/0241103 A1    Oct. 26, 2006

Related U.S. Application Data

(60) Provisional application No. 60/393,680, filed on Jul. 2, 2002.

(51) Int. Cl.
*A61K 31/5513* (2006.01)
(52) U.S. Cl. .................................... 514/221; 424/93.41
(58) Field of Classification Search ............. 424/93.41; 514/221
See application file for complete search history.

(56) References Cited

U.S. PATENT DOCUMENTS

| 3,710,795 A | 1/1973 | Higuchi et al. ............... 128/260 |
| 6,319,958 B1 * | 11/2001 | Johnson et al. ............. 514/739 |
| 6,518,252 B2 | 2/2003 | Wooley ....................... 514/290 |

FOREIGN PATENT DOCUMENTS

| WO | WO 00/40269 | 7/2000 |
| WO | WO 02/46193 | 6/2002 |

OTHER PUBLICATIONS

White, L. E. 2002. 2-Ikoxycarbonylaminopyridines: inhibitors of Mycobacterium tuberculosis FtsZ, Journal of Antimicrobial Chemotherapy, vol. 50, pp. 111-114.*
White et al. 2002. 2-Alkoxycarbonylaminopyridines: inhibitors of Mycobacterium tuberculosis FTSE, Journal of Antimicrobial Chemotherapy, vol. 50, pp. 111-114.*
Allen et al. "Identification and cloning of *waaF* (*rfaF*) from *Bordetella pertussis* and use to generate mutants of *Bordetella* spp. with deep rough lipopolysaccharide." J Bacteriol. Jan. 1998;180(1):35-40.

Anthony-Cahill et al., "Site specific mutagenesis with unnatural amino acids" TIBS, 14 (10): 400-403 (1989).
Barry III et al. "Use of genomics and combinatorial chemistry in the development of new antimycobacterial drugs." Biochem Pharmacol. Feb. 1, 2000;59(3):221-231.
Benner, "Expanding the genetic lexicon: incorporating non-standard amino acids into proteins by ribosome-based synthesis" TIB Tech, 12 : 158-163 (1994).
Bodnar et al. J. Org. Chem. 62: 4737-4745,1997.
Brown et al., "Efficient diastereoselective synthesis of anti α-bromo-β-hydroxyketones" Tet. Lett. ; 40, 7875-7877,1999.
Bulman-Page et al. "A convenient preparation of symmetrical and ynsymmetrical 1,2-Diketones: Application to fluorinated pheytoin synthesis" Tet. Lett. 48 35 : 7265-7274,1992.
Creighton, T.E. "Proteins: Structure and Molecular Properties" W. H. Freeman & Co. , San Francisco pp. 79-86 [1983].
Curran, "Reduction $\Delta^2$-isoxazolines. A conceptually different approach to the formation of aldol adducts" Am. Chem. Soc., 104, 4024-4026, 1982.
Elliott et al. "Potentical fold acid antanists. II. Deaza analogs of methotrexate. II. 2,4-Diamino-6-methyl-3-deazapteridine" J. Org. Chem., 31 ; 1890-1894,1966.
Elliott et al., "Potential folic acid antangoists. VI. The syntheses of 1- and 3-deazamethotrexate" J. Org. Chem. 36: 2818-2823, 1971.
English Jr. and Bliss, "The preparation of deamination of some 1,3-amino alcohols" J. Am. Chem. Soc. 78, 4057-4060,1956.
Evans et al. "A review of antimicrobial peptides: defensins and related cationic peptides." Vet Clin Pathol. 1995;24(4):109-116.
Fridkin et al. "Design, synthesis and biological evaluation of polymyxin B nonapeptide analogs: novel antimicrobial compounds." Dept. of Org. Chem., pp. 212-213.
Fryer, R. I.; et al. In: Heterocyclic Compounds. John Wiley & Sons, Inc., pp. 209-420 (1991).
Haddad et al., "Stereocontrolled reductive amination of 3-Hydroxy ketones" TET Lett. 38 (34), 5981-5984,1997.
Horner, "Tremor-producing aminpopanols" J. Org. Chem. 10, 387-391,1967.
Hosokawa et al. "Palladium (II)-catalyzed cyclization of γ, σ-unsaturated alcohols synthesis of 2-vinyltetrahydrofurans" Tetrehedron Letters 21:1821-1824 (1976).
Ibba, "Strategies for in vitro and in vivo translation with non-natural amino acids" Biotechnology & Genetic Engineering Reviews 13: 197-216 (1995).
Ibba and Hennecke, "Towards Engineering Proteins by Site-Directed Incorporation in Vivo of Non-Natural Amino Acids" Bio/technology, 12: 678-682 (1994).
Jaeger et al. "Improved predictions of secondary structures for RNA" Proc. Natl. Acad. Sci. USA 86:7706-7710,1989.
Jaeger et al. "Predicting Optimal and Suboptimal Secondary Structure for RNA" Methods Enzymol. 183: 281-306, 1989.
Jiang, J.-L. et al. Synthetic Communications, 28 (2), 4137-4142,1998.

(Continued)

*Primary Examiner*—Ralph Gitomer
*Assistant Examiner*—Kailash C Srivastava
(74) *Attorney, Agent, or Firm*—Ballard Spahr, LLP

(57) ABSTRACT

The invention relates to inhibitors of FtsZ polymerization and uses thereof.

6 Claims, 9 Drawing Sheets

OTHER PUBLICATIONS

Kashimura et al., "Synthesis of symmetrical and unsymmetrical 1,2-Diketones through cathodic intramolecular coupling of diesters" Tet. Lett. 38 (38), 6717-6720, 1997.

Kobayashi and Haciya, "Lanthanide triflates as water-tolerant lewis acis. Activation of commercial formaldehyde solution and use in the aidol reaction of silyl enol ethers with aldehydes in aqueous media" J. Org. Chem. 59, 3590-3596, 1994.

Kokubo et al., "Rhodium-catalyzed coupling reaction of salicyl aldehydes via cleavage of the aldehyde C-H bond" J. Org. Chem. 62, 4564-4565, 1997.

Köpf-Maier and Saβ, "Antitumor activity of treosulfan in human lung carcinomas" Cancer Chemother. Pharmacol. (1996) 37:211-221.

Kuebrick et al., "The mechanism of the benzoin condensation" J. Am. Chem. Soc. 93: 1214-1220, 1971.

Kuwajima et al., "Regiospecific directed aldol reactions of methyl ketones with aldehydes" Tet. Lett. 21, 1817-1820, 1976.

Le Roux et al, "New effective catalysts for mukiyama-aldol and -michael reactions: $BiCl_3$-metallic iodide systems" J. Org. Chem. 58, 1835-1839, 1993.

Li, Chunhong, et al. "Design and synthesis of potent sensitizers of gram-negative bacteria based on cholic acid scaffolding" J. Am. Chem. Soc. 1998, 120:2961-2962.

Lister, Synthesis from Pyrimidines, Chapter II, J. Wiley & Sons, Inc.; (Taylor, E. C.; Ed.), 1996, pp. 21-59.

Madison-Antenucci, et al. "Measurement of Fluorescent FtsZ from Mycobacterium tuberculosis in a High-Throughput Polymerization Assay." T.M. Abstract: Submitted to the Society for Biomolecular Screening, Portland, Oregon, Sep. 20-26, 2003.

Marks and Walborsky, "Matallo aldimines 3. Coupling of lithium adimines with aryl, vinyl, and acetylenic halides" J. Org. Chem. 47 : 52-56, 1982.

Marks and Walborsky, "Metalloaldimines. 4. Reaction of Lithium aldimines with carvbonyl comounds and with activated alkyl halides" J Org. Chem. 46: 5405-5407 (1981).

Matsumoto and Hayashi, "Catalytic asymmetric sysnthesis of β-Hydroxy ketones by Palladium—catalyzed asymmetric 1,4-disilylation of a α,β-unsaturated ketones" Tetrahedron, 50 (2), 335-346,1994.

Matyus et al., "Synthesis, antihypertensive and α-adrenoceptor activity of novel 2-aminoalkyl-3(2H)-pyridazinones" Eur. J. Med. Chem. 27,107-114, 1997.

Mitchell, et al "Synthesis of symmetrical diaryl 1,2-diketones from gringard reagents and 1,1[1]- oxalylimidazole" Tetrahedron Letters 34 (23) : 3683-3686, 1993.

Morihata, et al. "Stereoselective Synthesis of 1,3-Diol from β-Hydroxyacylsilane via rearrangement of phenyl group from silicon to carbon" TET. Lett. 6(31), 5555-5558,1995.

Mukaiyama, "Metal enolates in organic synthesis" Pure & Appl. Chem. 55 (11), 1749-1758,1983.

Mukaiyama, et al "New cross-aldol reactions, reactions of silyl enol ethers with carbonyl compounds activated by titanium tetrachloride" J. Am. Chem. Soc. 96.: 24, 7503-7509,1974.

Mukherjee and Lutkenhaus "Analysis of FtsZ assembly by light scattering and determination of the role of divalent metal cations." J Bacteriol. Feb. 1999;181(3):823-832.

Mukherjee et al. "*Escherichia coli* cell division protein FtsZ is a guanine nucleotide binding protein." Proc Natl Acad Sci U S A. Feb 1, 1993;90(3):1053-1057.

Noyori, et al. "Erythro-selective aldol reaction via tris(dialkylamino)sulfonium enolates" J. Am. Chem. Soc., 103, 2106-2108,1981.

Oishi, et al. "Remarkable enhancement of catalyst activity of trialkylsilyll sulfonates on the mukaiyama aldol reaction: a new approach using bulky organoaluminum cocatalysts" J. Am. Chem. Soc. 120, 8271-8272,1998.

Olah, G. A. et al. "One-Flask Preparation of Symmetrical Ketones and 1,2-Diketones from Esters" Synthesis, 1 177-1179, 1991.

Qunying et al "Preparation and characterization of cholic acid-derived antimicrobial agents with controlled stabilities" Organic Letters 2: 2837-2840,2000.

Ruegg et al., "Opioid-receptor subtype agonist-induced enhancements of sucrose intake are dependent upon sucrose concentration" Physiology & Behavior 62(1):121-128 (1997).

Seyferth, et al. "High yield acyl anion trapping reactions:synthesis of α-hydroxy ketones and 1,2-diketones" J. Org. Chem. 48 : 1144-1146,1948.

Shi, et al. "Synthesis of Symmetric Diketones from lmidazolinium Salt and Bis-Grignard Reagents" Chinese Chemical Letters, 11(9), 757-760, 2000.

Shortnacy, et al. "8-substituted furine reibosides: synthesis and biological activity" Nucleosides & Nucleotides, 8 (5&6): 911-913,1996.

Solladie-Cavallo and Quazzotti, "1,1-Dichloro-2m2m2-trifluroethyllithium in Asymetric synthesis II. A route to optically pure 4,4,4-trifluoro-2-hydroxybutanoic acid" Synthesis, 1177-1179, 1991.

Sossong et al. "Self-Activation of Guanosine Triphosphatase Activity by Oligomerization of the Bacterial Cell Division Protein FtsZ" Biochem. 38: 14843-14850,1990.

Stergiadesa and Tius, "α,β-unsaturated acyl silanes" J. Org. Chem. 64, 7547-7551,1999.

Stoilova et al. "A convenient one-flask synthesis of 1-Methylazetidines from 3-Aminoalkanol, Triphosphine, and Carbon Tetrachloride" Synthesis Communications, 105-106, 1997.

Suling et al "Effect of Surfactants on Antibiotic Resistance" Antimicrob. Agents Chemother. 8: 334-343,1975.

Suling et al. "Antimycrobial activities of 2,4-Diamino-5-Deazapteridine Derivatives and Effects of Myobacterial Dihydrofolate Reductase" Antimicrobial Agents and Chemotherapy 44, 2784-2793, 2000.

Suling et al. "Susceptibles of Mycobacterium tuberculosis and Mycobacterium avium complex to lipophillic deazapteridine derivates, inhibitors of dihydrofolate reductase" Journal of Antimicrobial Chemotherapy 42, 811-815, 1998.

Takahashi, et al. "An efficient method for synthesis of symmetrical diketones via reaction of α-amino-α-arylacetonitriles (masked acyl anion equivalents) with alkyl dibromides" J. Org. Chem. 48: 1909-1912,1983.

Temple et al "Synthesis of potential anticancer agents: imidazo[4,5-c]pyridines and imidazo[4,5-b]pyridines." J Med Chem. Oct. 1987;30(10):1746-1751.

Temple et al. "Synthesis of Potential Antimalarial Agents" J. Heterocyclic Chem. 7: 451-454,1970.

Temple, et al . "Antimitotic agents. Alterations at the 2,3-positions of ethyl (5-amino-1,2-dyhydropyido[3,4-b]pyrazin-7-yl)carbamates" J. Med. Chem. 34 : 3176-3181, 1991.

Temple, et al "Synthesis of potential antimalarial agents. VII. Azaquinolines I. The preparation of some pterdines and pyrido[3,4-b]pyrazines(I)" J. Heterocyclic Chem. 7: 1195-1202,1970.

Temple, et al. "Synthesis of potential antimalarial agents IV. The preparation of 8-amino-3-(p-chlorophenyl)-6-[4-(diethiamino)-1-methylbutyl]amino]pyrido[2,3-b]pyrazine" J. Med. Chem. 13: 853-857,1970.

Thorson et al., "A Biosynthetic Approach for the Incorporation of Unnatural Amino Acids into Proteins" Methods in Molec. Biol. 77: 43-73 (1991).

Tsubery et al. "Modulation of the hydrophobic domain of polymyxin B nonapeptide: effect on outer-membrane permeabilization and lipopolysaccharide neutralization." Mol Pharmacol. Nov. 2002;62(5):1036-1042.

Verlhac, et al. "A versatile access to unsymmetrical and symmetrical α-diketones via organotin reagents" Tet. Lett. 26 (49): 6075-6078, 1985.

Waring, Comprehensive Organic Chemistry. The Synthesis and Reactions of Organic Compounds. (Stoddart, J. R.; Ed.), Pergamon Press, pp. 1017-1095; 1979.

White et al."Slow polymerization of Mycobacterium tuberculosis FtsZ." J Bacteriol. Jul. 2000;182(14):4028-4034.

White et al. "Biochemistry of *Mycobacterium tuberculosis* FtsZ." Presentation.

White et al. "2-Alkoxycarbonylaminopyridines: inhibitors of *Mycobacterium tuberculosis* FtsZ." Journal of Antimicrobial Chemotherapy (2002) 50, 111-114.

Zoller, "New recombinant DNA methodology for protein engineering" Current Opinion in Biotechnology, 3: 348-354 (1992).

Zuker, M. "On Finding All Suboptimal Foldings of an RNA Molecule" Science 244: 48-52, 1989.

White, E.L.; Ross, L.J.; Reynolds, R.C., "Biochemistry of *Mycobacterium tuberculosis* FtsZ," Instituto Juan March de Estudios e Investigaciones, 146:23-5, 2002.

White, E.L.; Ross, L.J.; Borhani, D.W.; Reynolds, R.C., "FtsZ, An Essential Bacterial Division Protein," presented at Keystone Symposia on Tuberculosis: Integrating Host and Pathogen Biology, in Taos, New Mexico, Jan. 25-30, 2003.

Yoneda, et al. "Unequivocal synthesis of 6-arylpteridines by intramolecular cycloadditions of Azahexatrienes" J. C. S. Perkin Trans. 1, 11:1336-1339, 1977.

Bowdon et al. "Comparison of 1,2-dihydropyrido[3,4-b]pyrazines (1-diaza-7,8-dihydropteridines) with several other inhibitors of mitosis," Cancer Research 47(15):1621-6, 1987.

Supplemental European Search Report for EP 07804990.5-1221, mailed Nov. 19, 2008.

* cited by examiner

INHIBITORS OF FTSZ AND USES THEREOF

CROSS REFERENCE TO RELATED APPLICATIONS

The present application claims priority to and the benefit of the filing date of U.S. Application No. 60/393,680, filed on Jul. 2, 2002, which application is incorporated herein fully by this reference.

BACKGROUND OF THE INVENTION

1. Field of the Invention

This invention generally relates to the field of anti-microbial agents and their uses, particularly inhibitors of FtsZ.

2. Background Art

The mechanisms of action of many anti-bacterial agents have been well documented. For example, the mechanism of action of penicillin and other β-lactam drugs in inhibiting bacterial cell wall synthesis has been well studied. However, in other cases the mechanisms of action are not understood. There are six generic categories of action for anti-bacterial compounds, including inhibition of: 1) cell wall synthesis; 2) cell division; 3) cell membrane function; 4) protein synthesis; 5) nucleic acid synthesis; and 6) intermediary metabolism.

The development of tolerance and/or resistance to anti-bacterial agents is a significant threat to the ability to treat disease. Many factors have contributed to this increased observance of resistant strains, including 1) over-use of anti-bacterial agents; 2) inappropriate use of anti-bacterial agents; 3) the capability of many bacteria to exchange genetic material which confers resistance; 4) and the rapid mutation rate observed in many bacteria, allowing for selection of resistant strains. Once an organism has developed resistance to a particular anti-bacterial agent, it becomes important that an effective replacement be identified. If the organism develops resistance to this second anti-bacterial agent, another replacement is needed. As a result, continual development of new agents is required. The agent should selectively target the physiology of the organism, yet allow for action against a broad spectrum of organisms. Thus, needed in the art are anti-bacterial agents that serve as an effective replacement drug for single and multiple-drug resistant strains.

SUMMARY OF THE INVENTION

In accordance with the purpose(s) of this invention, as embodied and broadly described herein, this invention, in one aspect, relates to a method of inhibiting bacterial growth comprising contacting a bacterium with an effective amount of one or more compounds having the structure:

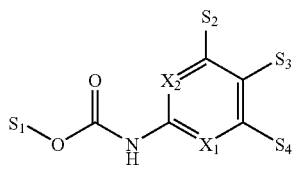

wherein
(a) $X_1$ and $X_2$ are CH or N, and at least one of $X_1$ and $X_2$ are N;
(b) $S_1$ is an organic radical;
(c) $S_2$, $S_3$, and $S_4$ are independently selected from hydrogen, amino, halogen, or one or more organic radicals;
(d) or a salt thereof.

In another aspect, the invention relates to a method of killing a bacterium comprising contacting the bacterium with an effective amount of one or more compounds having the structure and the various embodiments disclosed herein.

In yet another aspect, the invention relates to a method of inhibiting FtsZ polymerization in a bacterium comprising contacting the bacterium with an effective amount of one or more compounds having the structure and the various embodiments disclosed herein.

In a further aspect, the invention relates to a method of inhibiting bacterial growth comprising contacting a bacterium with an effective amount of a compound having the structure 4-[(6-Amino-2,3-diphenyl-pyrido[2,3-b]pyrazin-8-ylamino)-methyl]-N,N-diethyl-benzenesulfonamide.

The invention also relates to a method of treating a subject with a bacterial infection, comprising administering to the subject an effective amount of one or more compounds having the structure and various embodiments disclosed above.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

Figure 1:
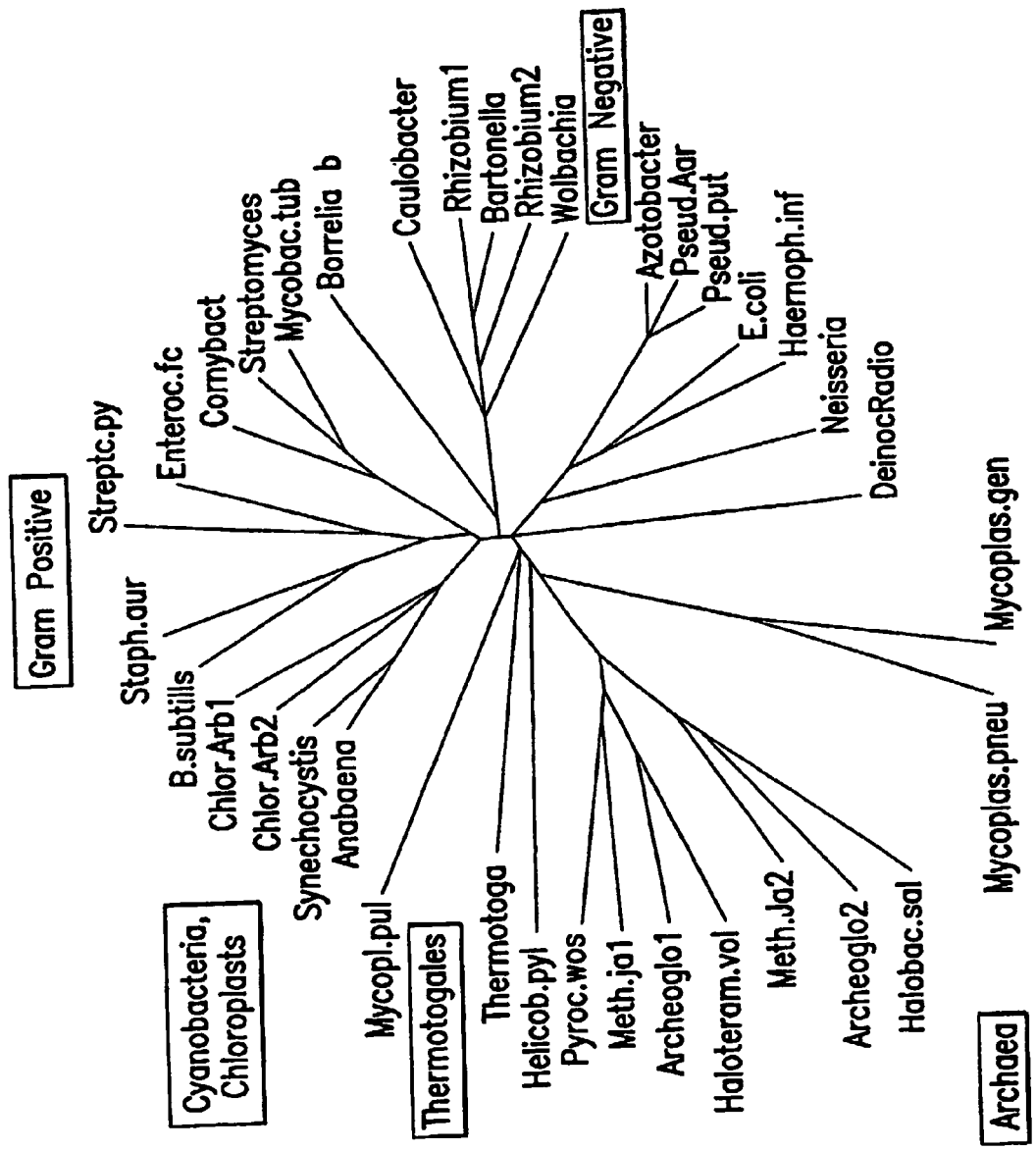
FIG. 1 shows the phylogenetic tree of FtsZ sequences from a variety of sources.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific mutants, or to particular screening methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a bacterium" includes cultures and populations of multiple bacteria, and reference to "bacteria" includes two or more bacterium, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

In the present disclosure, the use of compounds as inhibitors of bacterial cell growth and of FtsZ activity is described. As used in this specification and appended claims, the term "FtsZ" refers to the polypeptide listed in SwissProt Protein Data Base under accession number 008378 from *M. Tuberculosis*, and derivatives thereof.

"Derivatives" of FtsZ relates to a polypeptide that possesses a biological activity (either functional or structural) that is substantially similar to the biological activity of FtsZ, and includes "fragments," "variants," "analogs," "homologues," and "chemical alterations." Preferably, the derivative retains the ability to polymerize.

The term "fragment" is meant to refer to any polypeptide subset of FtsZ amino acid sequence incorporating 3 or more sequential or contiguous amino acids of FtsZ. The term "variant" is meant to refer to a molecule substantially similar in amino acid structure to either the entire FtsZ molecule, or to a fragment thereof. The term "analog" refers to a molecule substantially similar in function to either the entire FtsZ molecule, or to a fragment thereof. The term "homologue" is meant to refer to the corresponding FtsZ counterpart, or its derivative, in various bacteria, including but not limited to both Gram positive and Gram negative bacteria. The term "chemical alteration" means a derivative of FtsZ that has been modified structurally in some manner, but that functions in an analogous manner to FtsZ. Chemical alterations may be created by modification of the nucleotide sequence encoding the FtsZ genes (e.g., by substitution, addition, deletion, etc.), alternatively generated by synthesis of polypeptides in vitro, such as by chemical means, in vitro translation of mRNA, any other equivalent method known to one of skill in the art, or through the addition of chemical moieties to FtsZ. Also included are mutations to the ftsz gene, or protein thereof, that are naturally occurring.

A molecule is "substantially similar" or "homologous" to FtsZ in terms of structure if both molecules have more than 50% identity or 50% similarity, including 60%, 70%, 80%, 90%, or 95% identity between their respective amino acid sequences, or in terms of function if both molecules possess similar biological activity regardless of the similarity or identity of the amino acid sequences. Those of skill in the art readily understand how to determine the homology of two proteins.

The term "variants" refers to variations in the sequence of either a nucleic acid or a peptide molecule. It is understood that when variants are referred to, the variants designate specific properties dependent on the specific substitutions denoted, however, other substitutions, deletions, and/or insertions, for example, conservative substitutions, insertions, and/or deletions at positions other than the specifically denoted positions are also contemplated provided the variants retain the disclosed activities.

Most FtsZ amino acid sequences have a short N-terminal segment and a short to long C-terminal segment that display almost no sequence conservation among species. However, there is a conserved core sequence that is conserved across species. In *E. coli*, the conserved core extends from amino acids 10-316 and starts and ends with the following sequences (DAVIK (SEQ ID NO: 2)-VATGIG (SEQ ID NO: 3)). When the conserved core is used for comparison, the FtsZ sequences display 40-60% identity. A representative list of bacteria with conserved FtsZ sequences is shown in FIG. 1. The FtsZ core sequences share a remarkable degree of similarity over a wide range of organisms.

As discussed herein there are numerous variants of the FtsZ molecule that are known and herein contemplated. In addition to the known functional strain variants, there are derivatives of the FtsZ protein which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl-terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Substitutional variants are those in which at least one residue has been removed and a different residue inserted in its place. Such substitutions generally are made in accordance with the following Tables 1 and 2 and are referred to as conservative substitutions.

TABLE 1

Amino Acid abbreviations

| Amino Acid | Abbreviations | |
|---|---|---|
| Alanine | Ala | A |
| Allosoleucine | AIle | |
| Arginine | Arg | R |
| Asparagines | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Phenylalanine | Phe | F |
| Proline | Pro | P |
| pyroglutamic acid | Glup | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative Substitutions, others are known in the art.

| | |
|---|---|
| Ala | gly. Ser |
| Ar | glys, gln |
| Asn | gln; his |
| Asp | glu |
| Cys | ser |
| Gln | asn, lys |
| Glu | asp |
| Gly | ala, pro depending upon whether the gly plays a packing role [ala] or a turn role [pro] |
| His | asn; gln |
| Ile | leu; val |
| Leu | ile; val |
| Lys | arg; gln; |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of some types of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the FtsZ molecule. For example, there are numerous D amino acids or amino acids which have a different functional substituent than the amino acids shown in Table 1 and Table 2. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid or amino acid sequences. Many of the methods for determining homology between two evolutionarily related molecules are routinely applied to any two or more nucleic acids or proteins for the purpose of measuring sequence similarity regardless of whether they are evolutionarily related or not.

It is understood that the description of conservative mutations and homology can be combined together in any combination, such as embodiments that have at least 60%, 70%, 80%, 85%, 90%, 95%, 96%, 97%, 98%, or 99% homology to a particular sequence and wherein the variants include conservative amino acid substitutions.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 40, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using any of the calculation methods (although, in practice, the different calculation methods will often result in different calculated homology percentages).

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

The term "alkyl" denotes a hydrocarbon group or residue which is structurally similar to a non-cyclic alkane compound modified by the removal of one hydrogen from the non-cyclic alkane and the substitution therefore of a non-hydrogen group or residue. Alkyls comprise a noncyclic, saturated, straight or branched chain hydrocarbon residue having from 1 to 12 carbons, or 1 to 8 carbons, or 1 to 6 carbons. Examples of such alkyl radicals include methyl, ethyl, n-propyl, iso-propyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms.

The term "alkoxy" as used herein denotes an alkyl residue, defined above, bonded to an oxygen atom to form an ether radical, wherein the oxygen atom is also bonded to another radical. Examples include methoxy, ethoxy, n-propoxy, iso-propoxy, n-butoxy, t-butoxy, iso-butoxy and the like.

The term "mono-substituted amino" denotes an amino (—NHR) radical wherein the R radical is an organic radical. Suitable organic radicals include but are not limited to alkyl, haloalkyl, hydroxy, alkoxy, or acyl, wherein the terms have the definitions found herein. Examples of mono-substituted amino groups include methylamino (—NH—$CH_3$); ethylamino (—$NHCH_2CH_3$), hydroxyethylamino (—NH—$CH_2CH_2OH$), methoxyethylamino (—NH—$CH_2CH_2OCH_3$) and the like.

The term "di-substituted amino" denotes a disubstitued amino radical (—$NR_1R_2$) wherein $R_1$ and $R_2$ are organic radicals that can be same or different. Suitable organic radicals include but are not limited to alkyl, haloalkyl, hydroxy, alkoxy, or acyl, wherein the terms have the definitions found herein. Some examples include dimethylamino, methylethylamino, diethylamino, dihydroxyethylamino, and like radicals.

The term "haloalkyl" denotes a alkyl residue as defined above, wherein one or more hydrogens on the alkyl radical is replaced with one or more halogens. In some embodiments, the halogens are fluoro radicals. Examples include chloromethyl, trifluoromethyl, pentafluoroethyl and the like.

The term "haloalkoxy" denotes a haloalkyl residue as defined above, that is directly attached to an oxygen to form an ether radical having an haloalkyl substituent radical. Examples include trifluoromethoxy, pentafluoroethoxy and the like.

The term "acyl" denotes a R—C(O)— wherein the R radical is hydrogen or has a carbon of an organic radical bound to the carbonyl carbon atom. Examples include but are not limited to formyl, acetyl, propionyl, butanoyl, iso-butanoyl, pentanoyl, hexanoyl, heptanoyl, benzoyl and the like.

The term "acyloxy" denotes an acyl radical as defined above directly bonded to an oxygen to form an R—C(O)O— radical. Examples include but are not limited to acetyloxy, propionyloxy, butanoyloxy, iso-butanoyloxy, benzoyloxy and like radicals.

The term "aryl" denotes a hydrocarbon ring radical containing 6 to 18 carbons, or preferably 6 to 12 carbons, comprising at least one aromatic six-membered "benzene" ring therein. Examples of such aryl radicals include phenyl, biphenyl, and naphthyl. The term "substituted aryl" denotes an aryl ring radical as defined above that is substituted with one or more, or preferably 1, 2, or 3 organic rings, radicals, or inorganic substituents, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups can comprise from 1 to 12 carbon atoms, or from 1 to 6 carbon atoms, or from 1 to 4 carbon atoms.

The term "heteroaryl" denotes an aromatic ring radical containing 1 to 18 ring carbons, or 2 to 15 ring carbons, or 3 to 12 ring carbons, or 4 to 10 ring carbons, or 5 to 8 ring carbons, wherein at least one carbon of an aromatic ring therein has been replaced with a heteroatom, which include but are not limited to nitrogen, oxygen, and sulfur atoms. Heteroaryls may have one, two, three, four, five, or six independently selected ring heteroatoms. Examples of heteroaryl residues include pyridyl, bipyridyl, furanyl, and thiofuranyl residues. Substituted "heteroaryl" residues can have one or more organic radicals, or inorganic substituent s, or preferably 1, 2, or 3 such groups, as referred to herein-above, bound to the carbon atoms of the heteroaromatic rings. The organic substituent groups can comprise from 1 to 12 carbon atoms, or from 1 to 6 carbon atoms, or from 1 to 4 carbon atoms.

The term "halo" or "halogen" refers to a fluoro, chloro, bromo or iodo radical.

The term "thioalkyl" denotes a sulfide atom bonded to an alkyl radical, linear or branched. Examples include methylsulfide, ethyl sulfide, isopropylsulfide and the like.

The term "thiohaloalkyl" denotes a thioalkyl radical wherein one or more hydrogens has been replaced with a halogen atom. Examples include trifluoromethylthio, 1,1-difluoroethylthio, 2,2,2-trifluoroethylthio and the like.

The term "cycloalkyl" denotes a hydrocarbon radical which is structurally similar to a cyclic alkane compound modified by the removal of one hydrogen from the cyclic alkane and substitution therefore of a non-hydrogen group or residue. Cycloalkyl groups, or residues radical contain 3 to 18 carbons, or preferably 4 to 12 carbons, or 5 to 8 carbons. Examples include as cyclopropyl, cyclobutyl, cyclopentyl, cyclohexyl, cycloheptyl, decahydronapthyl, adamantyl, and like residues.

The term "substituted cycloalkyl" denotes a cycloalkyl residue as defined above that is further substituted with one, two, or more additional organic radicals or inorganic substituents that can include but are not limited to halogen, alkyl, substituted alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one substituent group, they can be the same or different. The organic substituent groups can comprise from 1 to 12 carbon atoms, or from 1 to 6 carbon atoms, or from 1 to 4 carbon atoms.

The term "cycloalkenyl" denotes a cycloalkyl radical as defined above that comprises at least one carbon-carbon double bond. Examples include but are not limited to cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like. The term "substituted cycloalkenyl" denotes a cycloalkyl as defined above further substituted with one or more organic radicals or inorganic substituents. Suitable substitutent radical include but are not limited to halogen, alkyl, hydroxyl, alkoxy, substituted alkoxy, haloalkoxy, carboxy, carboalkoxy, alkylcarboxamide, dialkylcarboxamide, amino, mono-substituted amino or di-substituted amino radicals. When the cycloalkenyl is substituted with more than one group, they can be the same or different. The organic substituent groups can comprise from 1 to 12 carbon atoms, or from 1 to 6 carbon atoms, or from 1 to 4 carbon atoms.

"Organic radicals" as the term is defined and used herein contain one or more carbon atoms. An organic radical can have, for example, 1-26 carbon atoms, 1-18 carbon atoms, 1-12 carbon atoms, 1-8 carbon atoms, or 1-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

The expression "prodrug" refers to compounds that are drug precursors that, following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula (I) compounds include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as b-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Methods of the Invention

The present invention provides in vivo and in vitro anti-bacterial methods. By "anti-bacterial" is meant inhibiting or preventing bacterial growth, killing bacteria, or reducing the number of bacteria. Thus, the present invention provides a method of inhibiting or preventing bacterial growth comprising contacting a bacterium with an effective amount of one or more compounds having the structure:

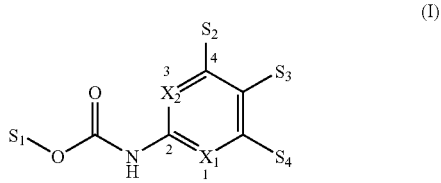

(I)

Additional structures for the compounds of the invention are provided herein.

Also, the present invention provides a method of inhibiting or preventing bacterial growth comprising contacting a bacterium with an effective amount of one or more compounds having the formula 4-[(6-Amino-2,3-diphenyl-pyrido[2,3-b]pyrazin-8-ylamino)-methyl]-N,N-diethyl-benzenesulfonamide.

"Inhibiting bacterial growth" is defined as reducing the ability of a single bacterium to divide into daughter cells, or reducing the ability of a population of bacteria to daughter cells. The ability of the bacteria to reproduce can be reduced by about 10%, about 20%, about 30%, about 40%, about 50%, about 60%, about 70%, about 80%, about 90%, or 100% or more.

The present invention also provides a method of killing a bacterium or population of bacteria comprising contacting the bacterium with one or more of is the compounds disclosed and described herein.

"Killing a bacterium" is defined as causing the death of a single bacterium, or reducing the number of a plurality of bacteria, such as those in a colony. When the bacteria are referred to in the plural form, the "killing of bacteria" is defined as cell death of a given population of bacteria at the rate of 10% of the population, 20% of the population, 30% of the population, 40% of the population, 50% of the population, 60% of the population, 70% of the population, 80% of the population, 90% of the population, or less than or equal to 100% of the population.

The FtsZ inhibitors of the invention have anti-bacterial activity in vitro or in vivo. A series of compounds are shown in Table 3 and Table 8. These compounds were screened for potential anti-bacterial activity against *M. tuberculosis* H37Rv at a concentration of 12.5 g/ml. Compounds that demonstrated at least 90% inhibition of bacterial growth were selected for further study.

As shown in Table 3 and Table 8, several of the compounds demonstrated activity against *M. tuberculosis* H37Rv in the primary screen. These included SRI-7405, SRI-3072, SRI-7614, SRI7462, 4427-026-15, 4427-143, CAO-040, 3491-23 and 3302-98F. Several of these compounds were tested at lower concentrations against *M. tuberculosis* H37Rv to determine the minimum inhibitory concentration ($MIC_{99}$) (BACTEC assay) and against mammalian Vero cells to determine the $IC_{50}$ (MTS assay) as described below. Using the $MIC_{99}$ and the $IC_{50}$ values, the selectivity index (SI, defined as the $IC_{50}/MIC_{99}$) for these compounds was determined. SRI-7614 had an $MIC_{99}$ of 6.25 mg/L (19 μM) and an $IC_{50}$ of >200 μg/ml. The resulting SI for SRI-7614 was >32. SRI-3072 had an $MIC_{99}$ of 0.15 μg/ml (0.28 μM) and an $IC_{50}$ of 6.3 μg/ml. The resulting SI for SRI-3072 was 42.0. Additional results are shown in Table 3. These results indicate a wide range of anti-bacterial activity for the compounds of the invention.

Figure 2:
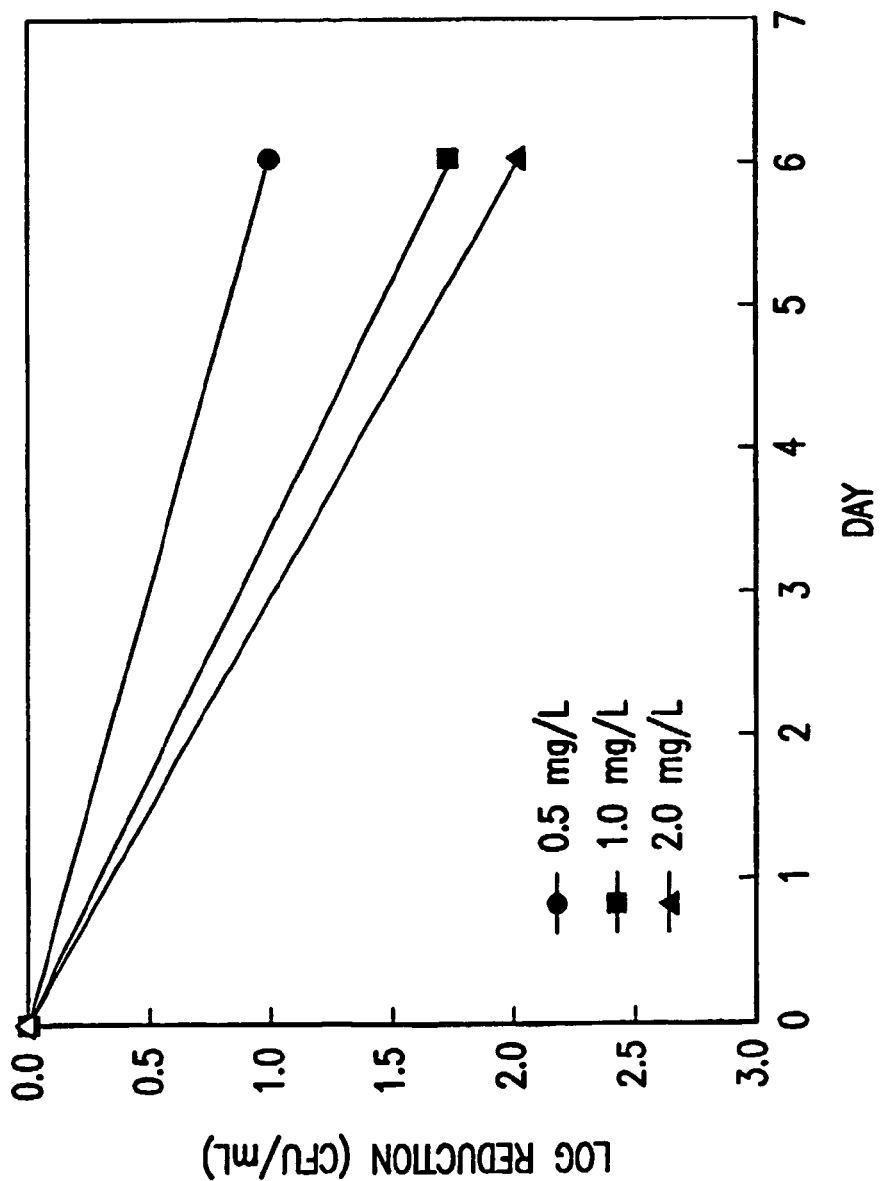
FIG. 2 shows the bactericidal activity of SRI-3072 for *M. tuberculosis* H37Ra. The cfu/ml in the presence of 2, 4, and 8 times the MIC (0.25 mg/ml) was determined by plating onto 7H11 agar after six days of incubation in the presence of drug.
Figure 3:
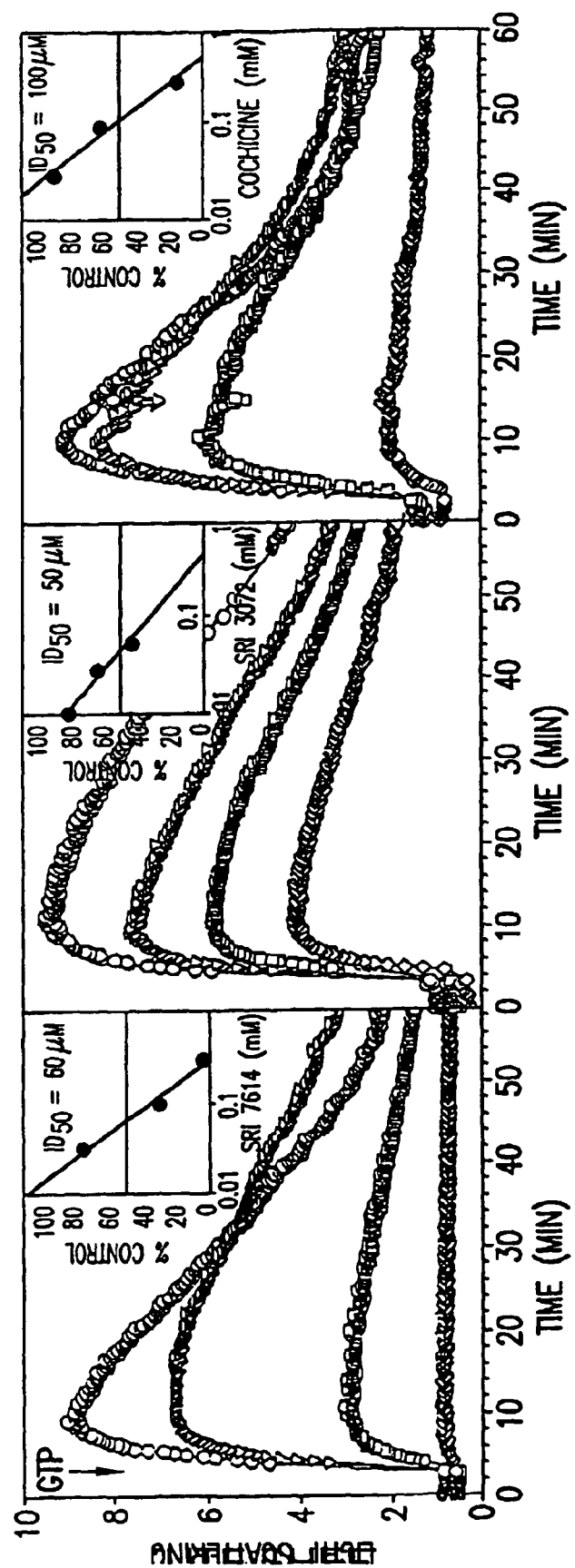
FIG. 3 shows inhibition of *M. tuberculosis* FtsZ polymerization. FtsZ (13 µM) was incubated with different concentrations of SRI-7614, SRI-3072 and colchicine in polymerization buffer. Polymerization was initiated by the addition of 40 uM GTP and the increase in fluorescence was measured using a 90 degree light scattering assay. The inserts illustrate determination of $ID_{50}$ values. The maximum light scattering was calculated by subtracting the baseline value before GTP addition from the peak value.
Figure 4:
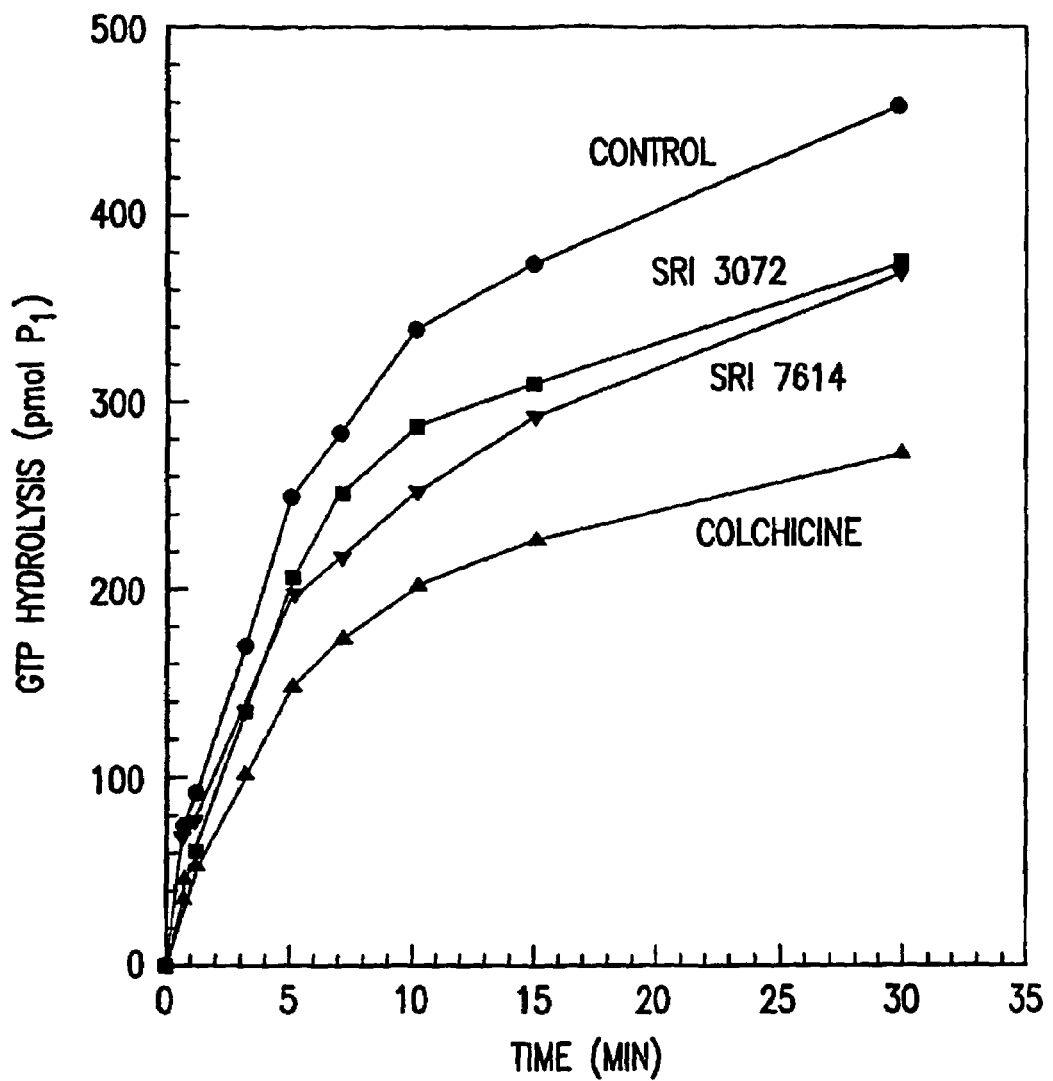
FIG. 4 illustrates inhibition of GTP hydrolysis. FtsZ was assayed under the same condition described in the polymerization assay. At various time points, 25 µl aliquots were withdrawn and assayed for the release of $^{32}P$ The time course for GTP hydrolysis was determined in the presence of 100 µM colchicine, SRI-7614 and SRI-3072 and compared to control.
Figure 5:
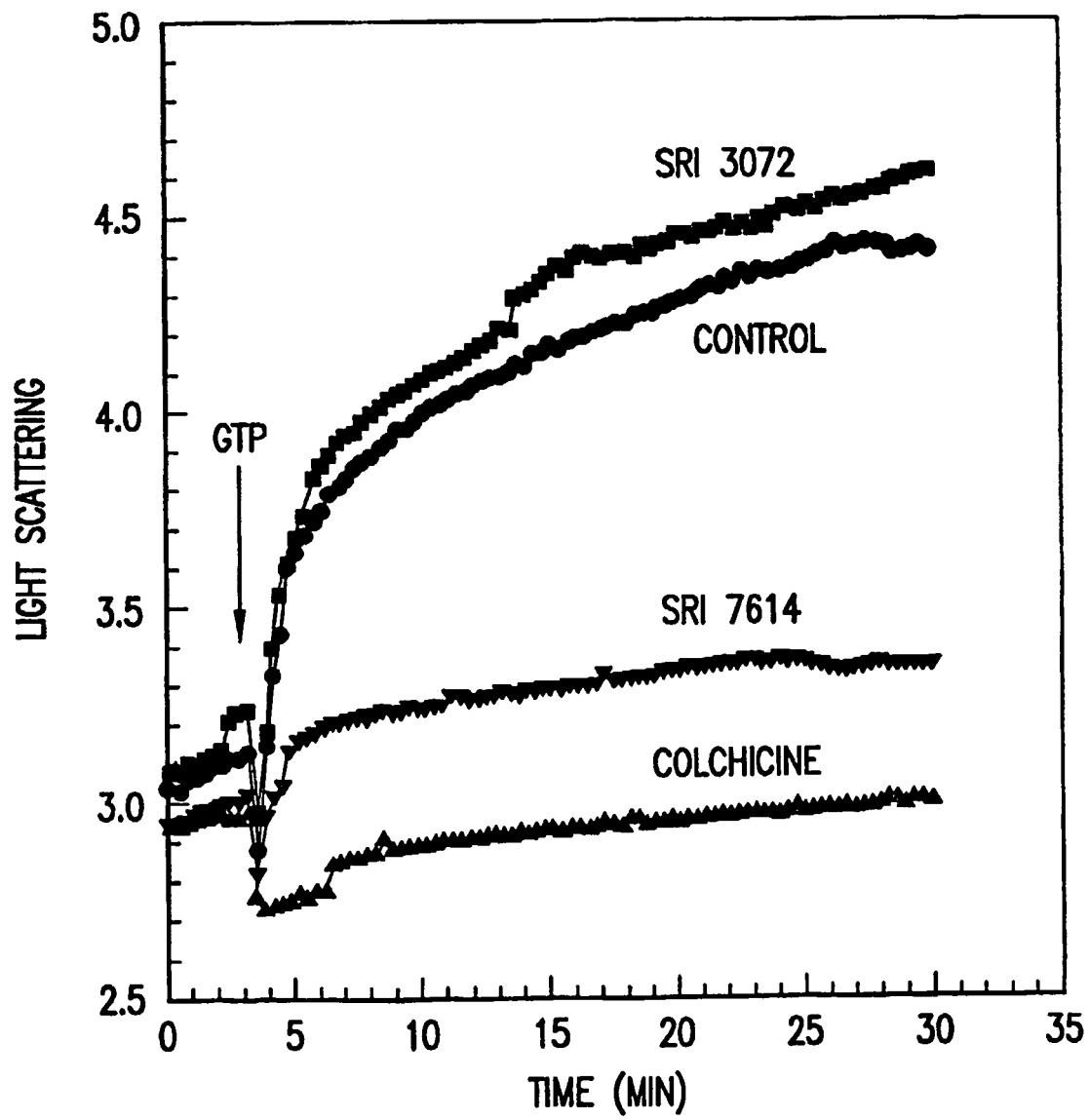
FIG. 5 illustrates inhibition of tubulin polymerization. Tubulin (20 uM) was incubated with 100 uM colchicine, SRI-7614 and SRI-3072 in polymerization buffer and compared to control. Polymerization was initiated by the addition of 1 mM GTP and the increase in fluorescence was measured using a 90 degree light scattering assay.

Strains of *M. tuberculosis* that were singly resistant to either isoniazid, rifampin, ethambutol, kanamycin, pyrazinamide, thiacetazone, or cycloserine were uniformly susceptible to SRI-7614 and SRI-3072 with $MIC_{99}$ values similar to those of the wild type strain (Table 5). Thus, the compounds of the invention are useful against antibiotic resistant bacteria The MIC and MBC of SRI-3072 for *M. tuberculosis* H37Ra were 0.25 mg/L (0.47 μM) and 1-2 mg/L (1.9-3.8 μM) (FIG. 2). The log reduction in cfu/mL in the presence of 0.95, 1.9 and 3.8 μM drug was 0.98±0.11, 1.7±0.06 and 2.0±0.12, respectively. Growth in the viability control without drug was estimated to have increased ≧1–$log_{10}$ cfu/mL after six days of incubation (see Example 1).

In a preferred embodiment, a bactericidal ratio of MBC to MIC is ≦about 4. For SRI-3072, this ratio was 4 using a value for the MBC of 1.9 μM.

SRI-3072 inhibited the growth of *M. tuberculosis* in infected mouse bone marrow macrophages. The concentration effecting 90% and 99% reduction in mycobacterial growth after seven days was 0.23 μM (0.12 μg/ml, $EC_{90}$) and 2.7 μM (1.42 μg/ml, $EC_{99}$), respectively. The $EC_{90}$ was similar to the MIC values for H37Rv, H37Ra, Erdman, and the drug-resistant strains indicating adequate permeability of SRI-3072 into macrophages.

Furthermore, SRI-3072 was assayed against *Escherichia coli, Enterococcus hirae,* and *Staphylococcus aureus,* representing a Gram negative rod and Gram positive cocci, respectively (Table 7). The drug was then tested against an expanded panel of Gram positive rods and cocci, which included methicillin-resistant staphylococci, multi-drug-resistant staphylococci and vancomycin-resistant enterococci. MICs against these organisms were in the range of 32-64 μg/mL except for the single Gram positive rod tested, *Bacillus subtilis,* which was inhibited at an MIC of 16 μg/mL. In conclusion, SRI-3072 showed moderate activity against several Gram-positive bacteria, including drug resistant strains (Example 8).

The compounds of the invention showed anti-bacterial activity as demonstrated by inhibition of several different types of bacteria. SRI-3072 was also shown to inhibit the growth of *M. tuberculosis* Erdman in infected mouse bone macrophages.

The present invention also provides a method of treating a subject with a bacterial infection, comprising administering to the subject a therapeutically effective amount of a compound of the invention.

By the term "therapeutically effective amount" of a compound as provided herein is meant a nontoxic but sufficient amount of the compound to provide the desired reduction in one or more symptoms. As will be pointed out below, the exact amount of the compound required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation.

The compound or compounds of the invention are prepared using techniques known in the art. The compounds are individually or jointly combined with a pharmaceutically acceptable carrier or vehicle for administration to the subject. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses and without interacting with the other components of the composition in a deleterious manner. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the agents and which is incorporated by reference herein.

The compounds may be administered orally, parenterally (e.g., intravenously), intramuscularly, intraperitoneally, topically, transdermally, locally, systemically, intraventricularly, intracerebrally, subdurally, intra-articularly, or intrathecally, intranasally or by intubation. Depending upon the agent and the mode of administration, special provisions may be required to promote the agent to cross the blood brain barrier. One skilled in the art would know to modify the mode of administration, the pharmacologic carrier, or other parameters to circumvent restrictions posed by the blood brain barrier. The amount of active compound administered will, of course, be dependent on the subject being treated, the subject's weight, the manner of administration and the judgment of the prescribing physician, veterinarian, or nutritionist.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

This invention also encompasses pharmaceutical compositions containing prodrugs of compounds of the Formula (I) or other formulas provided herein. This invention also encompasses methods of treating or preventing disorders that can be treated or prevented by the inhibition of FtsZ comprising administering prodrugs of compounds of the Formula (I) or other formulas provided herein. Compounds of Formula (I) having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula (I) or other formulas provided herein. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently bonded to the above substituents of Formula (I) through the carbonyl carbon prodrug sidechain.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

The therapeutic compositions of the present disclosure can also be administered in the form of liposome delivery systems, such as small unilamellar vesicles, large unilamellar vesicles and multilamellar vesicles, microspheres or nanospheres and other delayed release compositions. Liposomes can be formed from a variety of phospholipids, such as cholesterol, stearylamine or phosphatidylcholines.

Therapeutic compositions of the present disclosure may also be delivered by the use of monoclonal antibodies as individual carriers to which the compound molecules are coupled. The therapeutic compositions of the present disclosure may also be coupled with soluble polymers as targetable drug carriers. Such polymers can include, but are not limited to, polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the therapeutic compositions of the present disclosure may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and crosslinked or amphipathic block copolymers of hydrogels.

For topical administration, liquids, suspension, lotions, creams, gels or the like may be used as long as the active compound can be delivered to the surface of the skin.

Preferably at least about 3%, more preferably about 10%, more preferably about 20%, more preferably about 30%, more preferably about 50%, more preferably 75% and even more preferably about 100% of the bacterial infection is reduced due to the administration of the compound. A reduction in the infection is determined by such parameters as reduced white blood cell count, reduced fever, reduced inflammation, reduced number of bacteria, or reduction in other indicators of bacterial infection. To increase the percentage of bacterial infection reduction, the dosage can increase to the most effective level that remains non-toxic to the subject.

As used throughout, "subject" refers to an individual. Preferably, the subject is a mammal such as a primate, and, more preferably, a human. "Subjects" can include domesticated animals (such as cats, dogs, etc.), livestock (e.g., cattle, horses, pigs, sheep, goats, etc.), laboratory animals (e.g., mouse, rabbit, rat, guinea pig, etc.) and fish.

A "bacterial infection" is defined as the presence of bacteria in a subject or sample. Such bacteria can be an outgrowth of naturally occurring bacteria in or on the subject or sample, or can be due to the invasion of a foreign organism.

The compounds of the invention can be used in the same manner as antibiotics. Uses of antibiotics are well established in the art. One example of their use includes treatment of animals. When needed, the compounds of the invention can be administered to the animal via injection or through feed or water, usually with the professional guidance of a veterinarian or nutritionist. They are delivered to animals either individually or in groups, depending on the circumstances such as disease severity and animal species. Treatment and care of the entire herd or flock may be necessary if all animals are of similar immune status and all are exposed to the same disease-causing microorganism.

Another example of a use for the compounds includes reducing a microbial infection of an aquatic animal, comprising the steps of selecting an aquatic animal having a microbial infection, providing an antimicrobial solution comprising a compound of the invention, chelating agents such as EDTA, TRIENE, adding a pH buffering agent to the solution and adjusting the pH thereof to a value of between about 7.0 and about 9.0, immersing the aquatic animal in the solution and leaving the aquatic animal therein for a period that is effective to reduce the microbial burden of the animal, removing the aquatic animal from the solution and returning the animal to water not containing the solution. The immersion of the aquatic animal in the solution containing the EDTA, a compound of the invention, and TRIENE and pH buffering agent may be repeated until the microbial burden of the animal is eliminated. (U.S. Pat. No. 6,518,252).

Other uses of the compounds of the invention include, but are not limited to, dental treatments and purification of water (this can include municipal water, sewage treatment systems, potable and non-potable water supplies, and hatcheries, for example).

One embodiment of the above method is that the compound that inhibits FtsZ polymerization does not inhibit polymerization of tubulin. Tubulin is the protein that polymerizes into long chains or filaments that form microtubules, hollow fibers which serve as a skeletal system for living cells. Microtubules have the ability to shift through various formations which is what enables a cell to undergo mitosis or to regulate intracellular transport.

"Inhibiting polymerization of tubulin" is defined as reducing the amount of polymerized tubulin (i.e. a reduction in the size and/or number of polymers) as compared to a control. Preferably such inhibition will include inhibiting 100% or less of tubulin polymerization, inhibiting 90% or less of tubulin polymerization, or 80% or less of tubulin polymerization, or 70% or less of tubulin polymerization, or 60% or less of tubulin polymerization, or 50% or less of tubulin polymerization, or 40% or less of tubulin polymerization, or 30% or less of tubulin polymerization, or 30% or less of tubulin polymerization, or 20% or less of tubulin polymerization, or 10% or less of tubulin polymerization, or 5% at least of tubulin polymerization.

At present, several highly active anti-bacterial compounds in the compounds of the invention have shown a structure-activity relationship (SAR) significantly different from that demonstrated by members of the 2-ACP class that show anti-neoplastic/tubulin inhibiting properties. Therefore, there are differences between the human tubulin and bacterial FtsZ proteins. Furthermore, while both FtsZ and tubulin both share the tubulin-identity motif (GGGTGS/TG) (SEQ ID NO:1), the overall amino acid sequence similarity of FtsZ and tubulin is low (<20% identity). Nevertheless, FtsZ and tubulin were found to have similar three-dimensional folds, and FtsZ appears to be the bacterial homologue of tubulin.

The present invention also provides for a method of inhibiting FtsZ polymerization in a bacterium comprising contacting the bacterium with a compound of the invention.

FtsZ plays a key role in the cell division process of most bacterial cells. FtsZ is a 40 kDa protein which is almost ubiquitous in bacteria. FtsZ is also present in chloroplasts. FtsZ polymerizes in a GTP dependent manner and has been shown to be the bacterial tubulin homolog. Both FtsZ and tubulin first form into linear protofilaments and these protofilaments then associate into larger structures such as sheets and tubes. As discussed above, the sequence similarity between FtsZ and tubulin, however, is generally low (<20% identity), but both FtsZ and tubulin share a stretch of amino acids known as the tubulin-identity motif (GGGTGS/TG) (SEQ ID NO: 1) which functions to bind and hydrolyze GTP. FtsZ from *Methanococcus jannaschii* was shown to have a similar three-dimensional fold as tubulin. In the cell division process, bacteria first select the proper site for cell division (the site at which the septa forms) usually with the aid of the Min C, D, and E proteins. FtsZ is the first non-regulatory element to appear at the septum site of bacteria, and the function of the septum has been shown to depend on correct FtsZ function. Inhibition of FtsZ function has been linked to defects in cell division in several types of bacteria and chloroplasts. In fact, a single amino-acid substitution within the tubulin-identity motif of FtsZ leads to a failure to initiate septum formation. During the cell division process, or septation, the diameter of the FtsZ ring becomes smaller as it remains at the leading edge of the invaginating cell wall. Therefore, FtsZ is a very promising target for new anti-bacterial agents because of its plays a central role in bacterial cell division.

"Inhibiting FtsZ polymerization" is defined as reducing or inhibiting the amount of FtsZ polymerization (either in the size and/or the number of polymers) that takes place in a single bacterium or in a population of bacteria as compared to a control. As used throughout, "control" is an untreated bacterium or population of bacteria. The untreated bacterium or population of bacteria can be the pre-treated or post-treated bacterium or bacteria or can be a unique bacterium population.

FtsZ polymerization can be reduced by less than 10%, 20%, 30%, 40%, 50%, 60%, 70%, 80%, 90%, or less than or equal to 100%.

The compounds were tested for inhibition of FtsZ and tubulin polymerization and FtsZ GTP hydrolysis. Colchicine, a known tubulin inhibitor, was also included as a reference compound. SRI-3072, SRI-7614, and colchicine inhibited *M. tuberculosis* FtsZ polymerization in a dose dependent fashion with $ID_{50}$ values of 52±12, 60±0.0, and 104±2.0 μM, respectively (Table 6). As GTP hydrolysis by FtsZ is required for polymerization of FtsZ to proceed, each compound was tested for inhibition of GTP hydrolysis. SRI 3072, SRI 7614, and colchicine inhibited GTP hydrolysis by 20%, 25%, and 30%, respectively.

SRI-3072, SRI-7614 and colchicine were also evaluated as inhibitors of tubulin polymerization (Table 5). As expected, colchicine was more effective as an inhibitor of tubulin than FtsZ. SRI-3072 was specific for FtsZ; no inhibition of tubulin was seen. Like colchicine, SRI-7614 inhibited polymerization of both proteins ($ID_{50}$=60 μM FtsZ, $ID_{50}$=4 μM tubulin). As discussed above and shown in Table 6, SRI 3072 and SRI-7614 were effective and specific inhibitors of *M. tuberculosis*. Also, as discussed in Example 8, SRI-3072 was also an effective and specific inhibitor of other types of bacteria.

Thus, in one embodiment, the compound inhibits FtsZ polymerization without inhibiting tubulin polymerization. The absence of inhibition of tubulin polymerization includes any inhibition less than 1.5 times the background of the assay or any inhibition that lacks statistical significance. There is a correlation between the antibacterial activity of selected compounds (as illustrated by SRI-3072 and SRI-7614) and inhibition of FtsZ polymerization and GTP hydrolysis.

The Structures of the Compounds

The methods of the invention relate to or utilize substituted 2-alkoxycarbonylaminopyrimidine or 2-alkoxycabonylamino-pyridine ("2-ACP") compounds. The general chemical structure of the compounds employed in the various methods of the invention are exemplified by the compound of Formula (I):

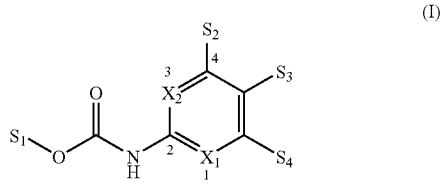

(I)

wherein $X_1$ and $X_2$ can be N or CH radicals, provided at least one of $X_1$ and $X_2$ is N. If both $X_1$ and $X_2$ are N, the compound is a substituted pyrimidine compound having structure (Ia) shown below. If only one of $X_1$ and $X_2$ are N, the compound is a substituted pyridine compound of Formulas (Ib) or (Ic) shown below.

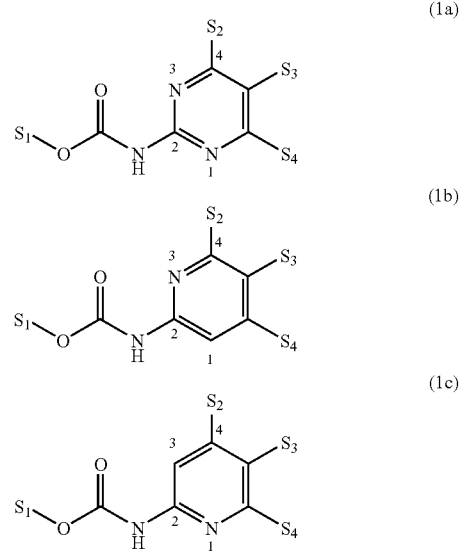

$S_1$ is an organic radical which includes but is not limited to an alkyl group or lower alkyl group. Several substitutions can be made to the 2-ACP nucleus, accordingly $S_2$, $S_3$, and $S_4$ can independently be hydrogen, amino, halogen, or one or more organic radicals as the term is further defined elsewhere herein, as will be further discussed hereinbelow, including organic radicals having N, O, S, and halogen heteroatoms therein. When $S_1$ is an alkyl group, an alkoxycarbonylamino radical (i.e. a carbamate radical, an ester of a carbamic acid) results and is bonded to the carbon at the "2" position of the heteroaromatic pyrimidine or pyridine rings, hence the "2-ACP" terminology. It is to be understood however that this "2-ACP" terminology does not necessarily limit the identity or composition of possible $S_1$ radicals to only alkyls.

In many embodiments, the 2-ACP compounds relating to the methods of the invention are bicyclic heteroaromatic compounds of Formula (II), as shown below:

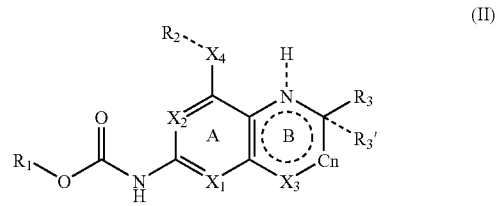

(II)

In the compounds of Formula (II), the "A" ring is a 6-membered aromatic heterocycle (i.e. heteroaryl) that is either a pyrimidine (both $X_1$ and $X_2$ are N), or a pyridine (one of $X_1$ and $X_2$ are N and the other is CH). $X_4$ can be hydrogen, halogen, an organic radical including but not limited to an alkyl or methylene group, or an oxygen, sulfur, phosphorus, or halogen atom, but in many embodiments is a nitrogen based radical such as an amino, mono-substituted amino, or disubstituted amino radical.

The nature of the "B" ring can vary. The $X_3$ radical can be a CH, N, O, S, or NH radical. The "B" ring can be aromatic, or it can be partially or completely saturated. The "B" ring comprises at least one N atom or NH radical, and at least one $X_3$ radical, as shown in the drawing. Bridging the N atom and the $X_3$ radical is at least one carbon based radical having at least one $R_3$ substituent, and an optional $R_{3'}$ substituent, so that the "B" ring has at least 5 ring atoms.

The compounds of Formula (II) may also comprise 6 or 7 membered "B" rings, corresponding to zero, one, or two additional "Cn" bridging carbon radicals (i.e. n can be 0, 1, or 2). The Cn bridging carbon-based radicals have an $R_4$ or $R_5$ substituent, and optionally may have an additional $R_{4'}$ or $R_{5'}$ substituent. If n=0, there is no additional Cn radical, and a 5-membered "B" ring results, as discussed above. If n=1, a $CR_4$ bridging radical is present in the "B" ring, that may optionally have an additional $R_{4'}$ substituent that may be the same or different than $R_4$, and a 6-membered "B" ring results. If n=2, an additional $CR_5$ bridging radical is also present (and optionally an additional $R_{5'}$ substituent), to form a 7-membered "B" ringed heterocycle. The $R_1$, $R_2$, $R_3$, $R_4$, and $R_5$ substituents can be hydrogen, halogen, oxygen (to form a carbonyl group), amino, hydroxy, or any organic radical, as the term is defined elsewhere herein. $R_2$ is an optional substitutent.

In many embodiments of the compounds of Formula (II), $X_3$ is N, $R_1$ is a lower alkyl group, such as methyl or ethyl; $R_2$ is an amino, mono-substituted amino, or di-substituted amino radical, and one or more of $R_3$, $R_4$, $R_5$, $R_{3'}$, $R_{4'}$, or $R_{5'}$ is hydrogen. In related embodiments, $R_2$ through $R_5$ can be phenyl, $(C_1-C_{20})$alkyl, X-Ph, X-PhCH$_2$, HetArCH$_2$, Me$_2$NCH$_2$(CH$_2$)n, MeOCH$_2$(CH$_2$)$_n$, etc. It should be noted that in many cases in which one of the Cn carbon atoms bears two differing $R_x$ groups, the resulting compound can potentially be chiral.

In some embodiments, the compounds of Formula (II) have an aromatic "B" ring. For example, if n=1, $X_1$, $X_2$, and $X_3$ are N, and the ring is aromatic so that $R_{3'}$ and $R_{4'}$ substitutents are not present, a genus of "pteridine" compounds of Formula (IIa) result. If n=1, and one of $X_1$ and $X_2$ is CH and the other is N, $X_3$ is N, and the "B" ring is aromatic genus of "deaza-pteridine" compounds of Formulas (IIb) and (IIb') result.

(IIa)

(IIb)

(IIb')

In some embodiments of the compounds of the invention, it is preferred that $R_1$ is a lower alkyl group including methyl or ethyl. In other embodiments, activity against bacteria can sometimes be enhanced by use of larger organic substituents, such as aryls, heteroaryls, or larger alkyls.

In some embodiments, $R_3$ and $R_4$ are benzene radicals. In some embodiments the $R_2$—$X_4$ radical is an amino or monosubstituted amino radical.

Examples of several compounds of Formula (IIb) are shown in Table 3 hereinbelow, including a compound "SRI-3072", which has been shown to be particularly effective when employed in the methods of the invention.

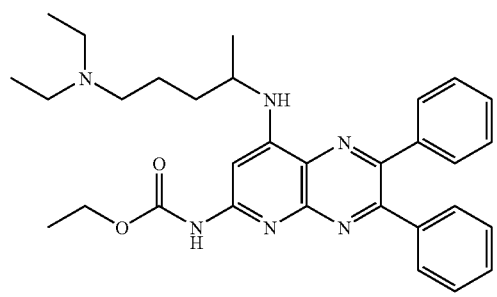

SRI-3072=[8-(4-Diethylamino-1-methyl-butylamino)-2,3-diphenyl-pyrido[2,3-b]pyrazin-6-yl]-carbamic acid ethyl ester The "B" ring need not be aromatic, and can be partially or completely saturated, with the result that $R_3'$ and/or $R_4'$ substituent radicals are present, as shown by compounds of Formulas (IIc) and (IId) below:

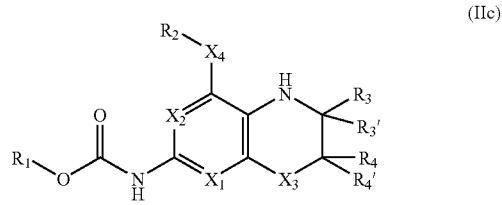

(IIc)

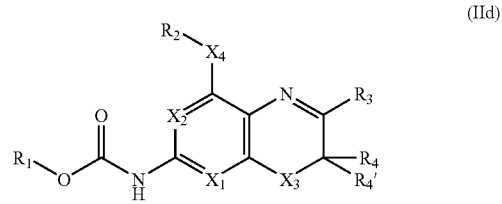

(IId)

Specific examples of deaza-pteridine compounds having a reduced, nonaromatic "B" ring are the compounds SRI-5713 and SRI-20158 as shown below.

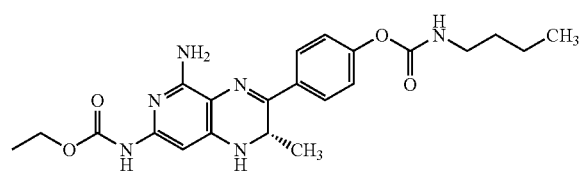

SRI-20158=[5-Amino-3-(4-butylcarbamoyloxy-phenyl)-2-methyl-1,2-dihydro-pyrido[3,4-b]pyrazin-7-yl]-carbamic acid ethyl ester

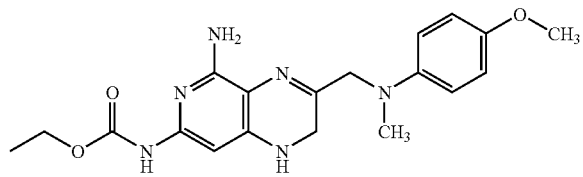

SRI-5713=(5-Amino-3-{[(4-methoxy-phenyl)-methyl-amino]-methyl}-1,2-dihydro-pyrido[3,4-b]pyrazin-7-yl)-carbamic acid ethyl ester In another genus of compounds having aromatic "B" rings, if n=0, $X_1$ is CH, $X_2$ is N, and $X_3$ is NH, a genus of 2-carbamate-substituted purine compounds having Formula (IIe) result:

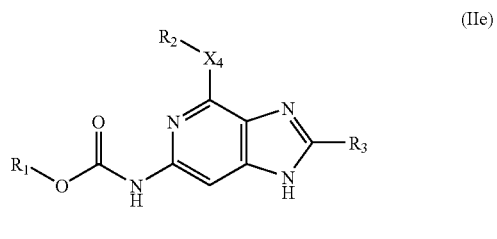

(IIe)

In yet another genus of compounds, if n=2, and $X_3$ is NH, a genus of 2-substituted diazapine compounds having Formula (IIf) result:

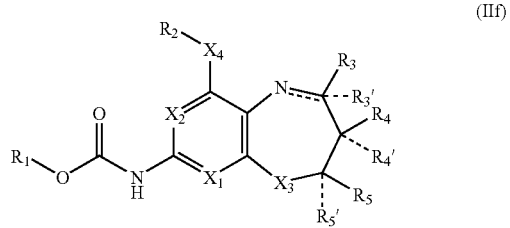

(IIf)

In some embodiments of the methods of the invention, the genus of diazapine compounds (IIg) shown below are of unusual interest;

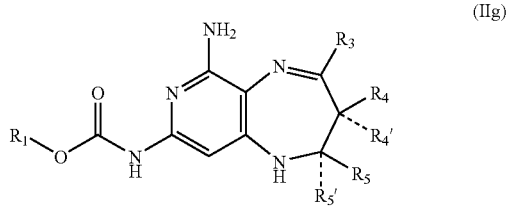

(IIg)

A particular pyrido-diazapine compound from the genus above, SRI-7614, has been found to be useful in the methods of the invention.

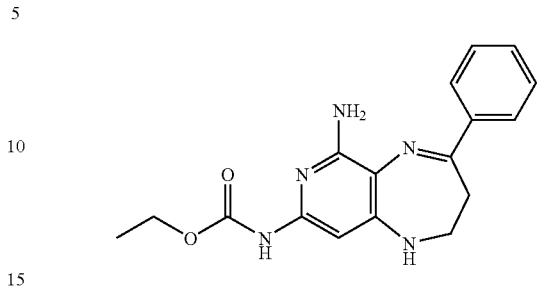

SRI-7614=(1-Amino-8-phenyl-6,7-dihydro-5H-2,5,9-triaza-benzocyclohepten-3-yl)-carbamic acid ethyl ester In yet other embodiments of the 2-ACP compounds of Formula (I), compounds have no "B" ring at all. A subgenus of such monocyclic compounds having Formula (III) is shown below.

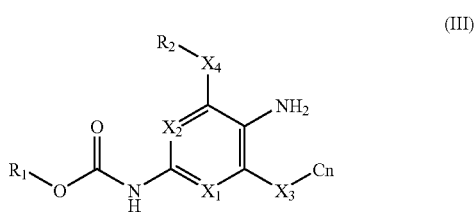

(III)

In the various embodiments of the invention relating compounds of formula (III), $R_1$, $R_2$, $X_1$, $X_2$, $X_3$ and $X_4$ can have any of the meanings described hereinabove for compound of Formulas (I) and (II). In these embodiments, Cn can be hydrogen or any organic radical as defined elsewhere herein. A species of this genus illustrated in Table 3 is SRI-7405, whose structure is shown below;

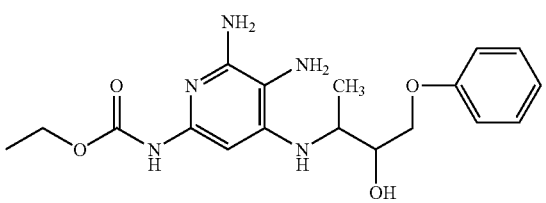

SRI-7405=[5,6-Diamino-4-(2-hydroxy-1-methyl-3-phenoxy-propylamino)-pyridin-2-yl]-carbamic acid ethyl ester Examples of compounds of the invention include, but are not limited to the compounds shown in Table 3 below, including, SRI-7405, SRI-3072, SRI-7614, SRI-7462, 4427-026-15, 4427-143, CAO-040, 3491-23 and 3302-89F, SRI-5713, and SRI-20158. Additional examples are in Table 8.

TABLE 3

Anti-bacterial Activity of 2-ACP Compounds

| Compound | Primary Screen PI | Screen 2 MIC$_{99}$ (µg/ml) | IC$_{50}$ (µg/ml) | SI (IC$_{50}$:MIC$_{99}$) |
|---|---|---|---|---|
| SRI-7405<br>[5,6-Diamino-4-(2-hydroxy-1-methyl-3-phenoxypropylamino)-pyridin-2-yl]-carbamic acid ethyl ester | 97 | 12.5 | >1000 | >80 |
| SRI-3072<br>[8-(4-Diethylamino-1-methyl-butylamino)-2,3-diphenyl-pyrido[2,3-b]pyrazin-6-yl)-carbamic acid ethyl ester | 100 | 0.15 | 6.3 | 42 |
| SRI-7614<br>(1-Amino-8-phenyl-6,7-dihydro-5H-2,5,9-triazabenzocyclohepten-3-yl)-carbamic acid ethyl ester | 100 | 6.25 | >200 | >32 |
| 4427-026-15<br>[2,3-Diphenyl-8-(4-sulfamoyl-benzylamino)-pyrido[2,3-b]pyrazin-6-yl]-carbamic acid ethyl ester | 97 | 0.39 | >6.25 | >16 |

TABLE 3-continued

Anti-bacterial Activity of 2-ACP Compounds

| Compound | Primary Screen PI | Screen 2 MIC$_{99}$ (μg/ml) | IC$_{50}$ (μg/ml) | SI (IC$_{50}$:MIC$_{99}$) |
|---|---|---|---|---|
| SRI-7462<br>(5-Amino-3-butyl-2-methyl-1,2-dihydro-pyrido[3,4-b]pyrazin-7-yl)-carbamic acid ethyl ester | 95 | 12.5 | 1.51 | 0.12 |
| 4427-143<br>4-[(6-Amino-2,3-diphenyl-pyrdo[2,3b]pyrazin-8-yl-amino)-methyl]-N,N-diethyl-benzenesulfonamide | 99 | 3.13 | ND | ND |
| CAO-040<br>(5-Amino-2,3-diphenyl-2H-pyrido-[4,3b][1,4]oxazin-7-yl)-carbamic acid ethyl ester ?? | 90 | 6.25 | ND | ND |
| 3491-23<br>(5-Ethoxy-2,3-diphenyl-pyrido[3,4-b]pyrazin-7-yl)-carbamic acid ethyl ester | 95 | ND | ND | ND |

TABLE 3-continued

Anti-bacterial Activity of 2-ACP Compounds

| Compound | Primary Screen P1 | Screen 2 MIC$_{99}$ (μg/ml) | IC$_{50}$ (μg/ml) | SI (IC$_{50}$:MIC$_{99}$) |
|---|---|---|---|---|
| 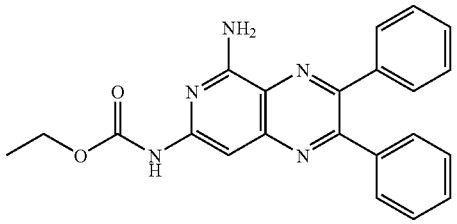<br>3302-89F<br>(5-Amino-2,3-diphenyl-pyrido[3,4-b]pyrazin-7-yl)-carbamic acid ethyl ester | 92 | ND | ND | ND |
| 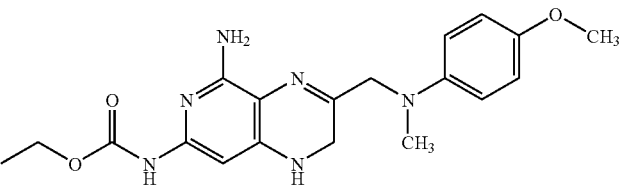<br>SRI-5713<br>(5-Amino-3-{[(4-methoxy-phenyl)-methyl-amino]-methyl-1,2-dihydro-pyrido[3,4-b]pyrazin-7-yl)-carbamic acid ethyl ester | 20 | ND | ND | ND |
| 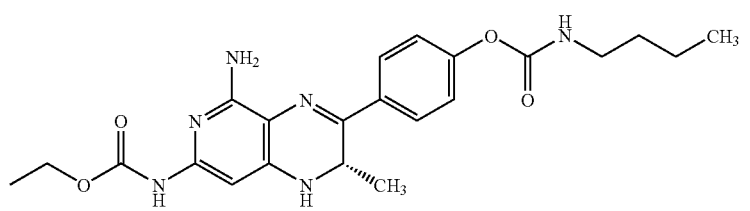<br>SRI-20158<br>[5-Amino-3-(4-butylcarbamoyloxy-phenyl)-2-methyl-1,2-dihydro-pyrido[3,4-b]pyrazin-7-yl]-carbamic acid ethyl ester | 10 | ND | ND | ND |

(P1 = % inhibition of growth at 12.5% μg/ml.)

Structure Activity Relationships of the Compounds

The above disclosures envision a range of substitutions at the $X_1$, $X_2$ and $X_3$ and a number of substituents at the $R_1$ through $R_5$ groups. While not wishing to be bound by either theory or empirical relationships, certain empirical relationships have been preliminarily observed between the substituent patterns of the compounds of Formula (I) and the activity observed in at least some of the methods of the invention.

For example, in the case of aromatic compounds of Formula (II), including Formulas (IIa) and (IIb), where Cn=1 and $R_3$ and $R_4$ are both relatively large and sterically bulky groups, such as phenyl groups, the interaction of the phenyl groups with one another can weaken the aromaticity of the pteridine structure and allow the side chain groups (phenyl groups in this case) to extend out of the plane of the aromatic ring structure. This may produce a conformation whereby one of the phenyl groups at $R_3$ and $R_4$ is able to interact with the active site of FtsZ.

In the case of compounds of Formula (IIf), where Cn=2, the 7 member ring will not be planar, placing the side chain groups at $R_3$-$R_5$ in a position where they may interact with the active site of FtsZ. Other mechanisms for the action of the compounds may exist and Applicants do not intend to remove from the scope of this disclosure other mechanisms of action.

The substitution patterns discussed above make the compounds more selective toward FtsZ inhibition than toward tubulin inhibition. Table 4 summarizes general structure activity relationships between of the compounds in regard to the selective inhibition of FtsZ using the 3-deazapteridines as an exemplary class. A similar structure-activity relationship for the other compounds, including the pyridodiazepine compounds may be expected.

TABLE 4

Structure-Activity Relationships of 2-ACP Compounds

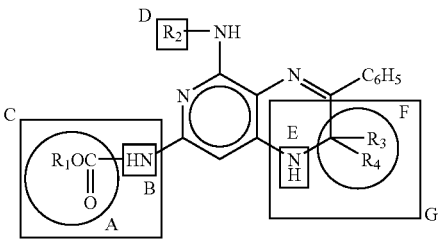

| Region | Effect on Mammalian Tubulin Inhibition | Effect on Bacterial Growth Inhibition |
|---|---|---|
| A | Activity reduced when $R_1$ = long chain or bulky aliphatic group, and when $R_1O_2C$ replaced by H or MeNHCO. Optimal: $R_1$ = Me, Et. | Larger steric groups can be tolerated. |
| B | Activity destroyed when NH removed. | Not determined. |
| C | Activity destroyed when replaced by H. | Not determined. |
| D | Activity reduced when $R_2$ = acyl or large group. Optimal: $R_2$ = H. | Larger steric groups can improve potency/selectivity |
| E | Activity reduced or destroyed by substitution with Me and by replacement with O or S. | Substitutions can maintain good activity. |
| F | Activity decreased: $R_3R_4$ = H, Me > H, H | Larger steric groups can be required for selectivity |
| G | Activity destroyed by aromatization. | Certain aromatic systems show high potency & selectivity |

The nomenclature and/or substitutent labeling of the compounds in Table 4 is different than that given in the compounds of Formulas (IIa-g) given above, however, it will be realized that substitutions at like positions in the structures of Formulas (IIa-g) may be equivalent.

For example, compounds substituted at Region D shown in Table 4 can maintain significant antitubercular activity (see Table 3, entries 2, 4, 6 & 8). Substitution at this "D" position in typical anticancer 7,8-dihydro-1-deazapteridines severely diminishes, or destroys, tubulin binding and anticancer activity. In fact, SRI-3072 (Table 3, entry 2) has good activity as an inhibitor in the FtsZ polymerization and GTP hydrolysis (Table 5), but shows no effect on polymerization of bovine tubulin at 100 µM. Clearly, the variability in Region D between these compounds (Table 6) affects the selectivity and activity of the compounds.

At Region A, the optimum $R_1$-group for anticancer activity is a methyl or ethyl group; larger alkyl groups can severely curtail tubulin binding capability. In contrast, a variety of compounds with larger $R_1$ alkyl groups (e.g. n-butyl, t-butyl, benzyl) show significant anti-bacterial activity (>95% inhibition of bacterial growth at 12.5 µg/mL), suggesting these compounds can also be capable of inhibition of FtsZ polymerization. Hence, alterations in the $R_1$-group of Region A can also affect the selectivity and activity of the compounds At Regions B & C the carbamate (Region C) is absolutely required as is the —HN-function (Region B) at the 2-position of the deazapteridine ring system for optimal anti-neoplastic activity. In contrast, compounds in the 3-deazapteridine class without the carbamate can retain significant anti-bacterial activity (see 4427-143, entry 6 in Table 3). Therefore, alterations in this region can also affect the selectivity and activity of the 2-ACP compounds.

Region G, composed of sub-Regions E & F, is a critical determinant in the tubulin binding and anticancer activity of the 1-deaza-7,8-dihydropteridines. At Region E (position 8 of the 1-deazapteridine ring), the heteroatom substitution must be an NH or activity is lost. In contrast, both O- and S-substituted compounds appear to retain significant anti-bacterial activity (e.g. compound CAO-040, entry 7 in Table 3). This alteration in the SAR profile at Region E represents another significant point where substitution with other heteroatoms may drive selectivity towards anti-bacterial activity and FtsZ inhibition.

Furthermore, the reduced form of the "B" ring of the pyridopyridazine, or the 1-deaza-7,8-dihydropteridine, ring system is absolutely required for optimum anti-neoplastic activity. Compounds such as SRI-3072, with a fully aromatic "B" ring system would not be expected to inhibit tubulin, as is shown in Table 6. Finally, substitutions at Region F in the 2-ACP compounds can critically influence activity and selectivity. Generally small groups are optimum for $R_3$ and $R_4$, typically H— or Me-substitution for tubulin binding and anti-neoplastic activity. Larger groups such as the 7-phenyl substitution in SRI-3072 are not tolerated for tubulin binding and anti-neoplastic activity. Nevertheless, compounds such as SRI-3072 show significant anti-bacterial activity, and their SAR is distinct from those compounds that inhibit mammalian tubulin polymerization. Furthermore, several of these compounds (such as SRI-3072) have impressive selectivity indices.

Additionally, it has been found that improved biological activity is often obtained when the molecular weight of the compounds of the invention is below about 500 grams per mole, or preferably about 450 or 400 grams per mole.

Synthesis of Representative Compounds

Synthetically, many of the compounds of Formulas (I), (IIa-g), and (III) are accessible through one of two key intermediates, whose structures are shown below.

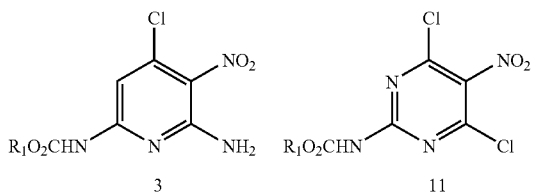

Figure 6:
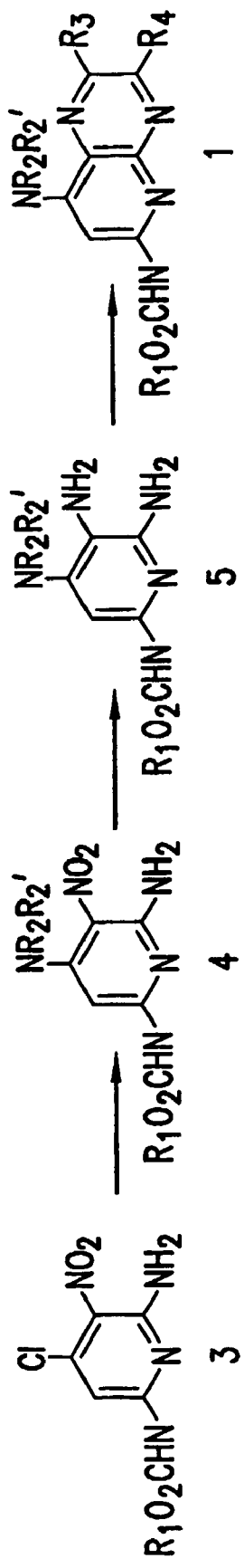
FIG. 6 shows one synthetic scheme for the synthesis of 3-deazapteridine compounds.

(6-Amino-4-chloro-5-nitro-pyridin-2-yl)-4,6-Dichloro-5-nitro-pyrimidin-2-ylamine carbamic acid ester A suitable starting material for many pyridino 2-ACP compounds of Formulas (Ib) and (Ic) has structure 3, also shown in FIG. 6, and is available by methods outlined in the art (Elliott, R. D. et al. *J. Org. Chem.*, 31: 1890-1894, 1966; Temple et al. *J. Med. Chem.*, 30: 1746-1751, 1987; Lister, J. H. *Synthesis from Pyrimidines*, Chapter II, J. Wiley & Sons, Inc.; (Taylor, E. C.; Ed.), 1996, pgs 21-59; Barry et al. *Biochem. Pharm.*, 59: 221-231, 2000; Shortnacy, A. T. et al. *Nucleosides & Nucleotides*, 8(5&6): 911-913, 1996), in 8 steps with an overall yield of 14% from chelidamic acid (Aldrich Chemical Co., Milwaukee Wis. U.S.A.) These references are incorporated herein in their entirety for the methods. This preparation has been scaled up to give large quantities of compound 3. The preparation of the analogous key starting compound 11 needed for the preparation of pyrimidine compounds of Formula (Ia) is much more facile (see FIG. 6) from a much cheaper starting material, in higher yields, as disclosed in Marks et al., *J. Org. Chem.* 46:5405-5407 (1981), which is incorporated herein by reference in its entirety for the methods.

The 3-deazapteridine compounds of Formula I as shown in FIG. 6 (for example, SRI-3072) can be readily obtained through displacement of the 4-chloro group of compound 3 with a substituted primary or secondary amine to form compound 4, followed by selective reduction of the 5-nitro group by any of a variety of known reactions with stoichiometric hydride sources such as NaBH$_4$, or by catalytic hydrogenation over various catalysts, to yield the ortho diamine compound 5, which can be condensed with a 1,2-diketone or benzil derivative (a Gabriel Colman-type preparation) to give the final target class 1, (Fryer, R. I.; et al. In: *Heterocyclic Compounds*. John Wiley & Sons, Inc.; (Taylor, E. C.; Ed.), pgs 209-420, 1991; Haddad, M. et al. *Tet. Lett.* 38(34), 5981-5984, 1997; English, J. et al. *J. Am. Chem. Soc.* 78, 4057-4060, 1956; Homer, J. K *J. Org. Chem.* 10, 387-391, 1967; Stoilova, V. et al. *Synthesis Communications*, 105-106, 1997). This reaction sequence is very useful for preparing symmetrical compounds having identical R$_3$ and R$_4$ radicals, and a variety of suitable diketones are available (Matyus, et al., *Eur. J. Med. Chem.* 27, 107-114, 1997; Curran, D. *J. Am. Chem. Soc.*, 104, 4024-4026, 1982; Mukaiyama, T. *Pure & Appl. Chem.* 55(11), 1749-1758, 1983 Mukaiyama, T. et al. *J. Am. Chem. Soc.* 96:24, 7503-7509, 1974; Le Roux, C.; Gaspard et al. *J. Org. Chem.* 58, 1835-1839, 1993; Kuwajima, I. et al. *Tet. Lett.* 21, 1817-1820, 1976; Kobayashi, S. et al. *J. Org. Chem.* 59, 3590-3596, 1994; Oishi, M. et al. *J. Am. Chem. Soc.* 120, 8271-8272, 1998; Noyori, R. et al. *J. Am. Chem. Soc.*, 103, 2106-2108, 1981). When unsymmetrical ketones are employed in this reaction sequence mixtures of isomers at R$_3$ and R$_4$ may be obtained. The ratios of products obtained can be controlled by the reactivity of the diamine (the amine derived by reduction of the nitro group meta to the ring nitrogen is the most reactive) as well as as differential reactivity of the ketones. In some cases, mixtures have been prepared that were readily separable.

Reactions can sometimes be utilized that will give unequivocal regiochemistry with respect to R$_3$ and R$_4$ For example in a Timmis-type preparation of pteridines, readily available halocarbonyl compounds can react regiospecifically to yield 7,8-dihydrodeazapteridines that can readily air oxidize to give the fully aromatic system. An interesting and useful reaction of 5,6-diamino-pyrimidines can also be adapted to this situation (Bodnar et al. *J. Org. Chem.* 62:4737-4745, 1997). In this reaction, the more reactive 5-amino group is first reacted with an aldehyde followed by reaction of the 6-amino group with an orthoester. Heating initiates ring closure to give 6,7-disubstituted pteridines. This situation is analogous except that the more reactive meta amino group can form the reactive imine, and ring closure can be executed by reaction of the remaining 6-amino group with the orthoester and heating. Other alternatives such as -hydroxy and -amino ketones can also prove useful (Matsumoto, *Tetrahedron*, 50(2), 335-346, 1994; Marks, M. J.; *J. Org. Chem.* 47: 52-56, 1982; Stergiades, I. A.; *J. Org. Chem.* 64, 7547-7551, 1999; Brown, H. C. et al. *Tet. Lett.;* 40, 7875-7877, 1999; Kokubo, K. et al. *J. Org. Chem.* 62, 4564-4565, 1997; Morihata, K. et al. *Tet. Lett.* 6(31), 5555-5558, 1995; Elliott, R. D. *J. Org. Chem.* 36:2818-2823, 1971; Temple, C., Jr. et al. *J. Heterocyclic Chem.* 7:451-454, 1970). It is notable that regiochemistry is easily controlled in the 1-deazapteridine ring system, the fully aromatic 6,7-disubstituted deazapteridines can be of interest. Finally, several alternative approaches similar to those discussed for the pyridodiazepine targets (2) could be used to obtain appropriately substituted 3-deazapteridines.

Figure 7:
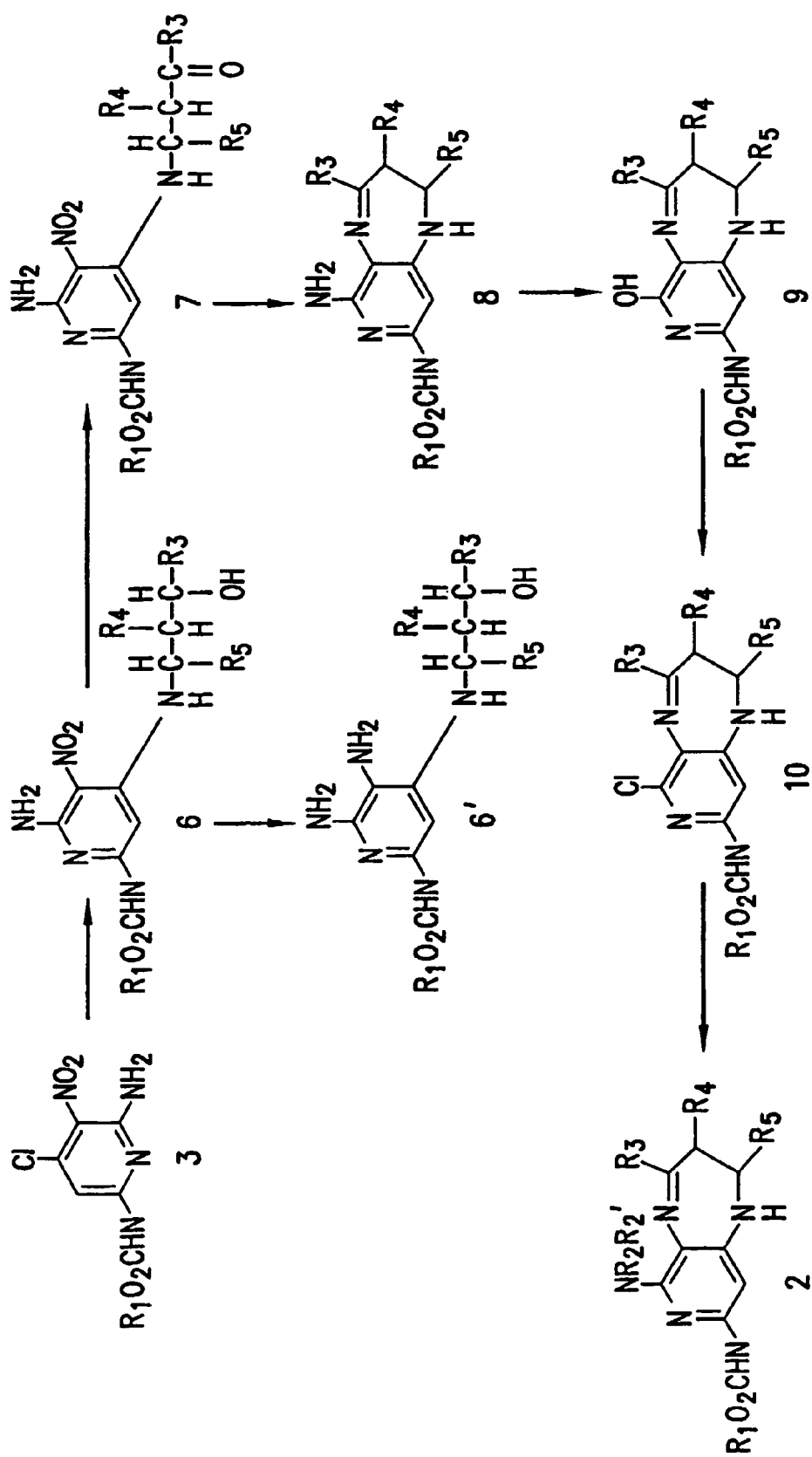
FIG. 7 shows one synthetic scheme for the synthesis of pyridodiazepine compounds.

Bicyclic diazepines of Formula (IIf), such as compound 2 shown in FIG. 7 are typically prepared by reaction of an o-arylenediamine with α,β-unsaturated aldehydes, α,β-unsaturated ketones, β-haloketones, β-aminoketones, or β-hydroxyketones. If either the diamine or the carbonyl function is asymmetrical, mixtures may result. In the case of the pyridodiazepines, regioselectivity can be controlled by reaction of the reactive 4-chloro group of 3 with a 3-aminopropanol (Temple et al. *J. Heterocyclic Chem.* 7:451-454, 1970). A wide variety of substituted 3-aminopropanols are synthetically accessible (Temple, C. et al. *J. Heterocyclic Chem.* 7: 1195-1202, 1970; Temple, C. et al. *J. Med. Chem.* 13: 853-857, 1970; Waring, A. J. *Comprehensive Organic Chemistry. The Synthesis and Reactions of Organic Compounds.* (Stoddart, J. R.; Ed.), Pergamon Press, pgs. 1017-1095; 1979; Bulman-Page, P. C. et al. *Tet. Lett.* 48(35): 7265-7274, 1992; Olah, G. A. et al. *Synthesis*, 1177-1179, 1991). For example, a diversity of 3-aminopropanols can be prepared through the reductive amination of 3-hydroxy ketones, which are in turn typically prepared via the Mukaiyama-Aldol reaction as well as other methods (Mitchell, R. H. et al. *Tetrahedron Letters* 34(23): 3683-3686, 1993; Takahashi, K.; et al. *J. Org. Chem.* 48: 1909-1912, 1983; Shi, Z. et al. *Chinese Chemical Letters*, 11(9), 757-760, 2000; Jiang, J.-L. et al. *Synthetic Communications*, 28(2), 4137-4142, 1998; Kashimura, S. et al. *Tet. Lett.* 38(38), 6717-6720, 1997; Verlhac, J. B. et al. *Tet. Lett.* 26(49): 6075-6078, 1985; Yoneda, F. et al. *J.C.S. Perkin I*, 1336-1339; Temple, C. et al. *J. Med. Chem.* 34:3176-3181, 1981; Seyferth, D. et al. *J. Org. Chem.* 48: 1144-1146, 1948.)

Figure 8:
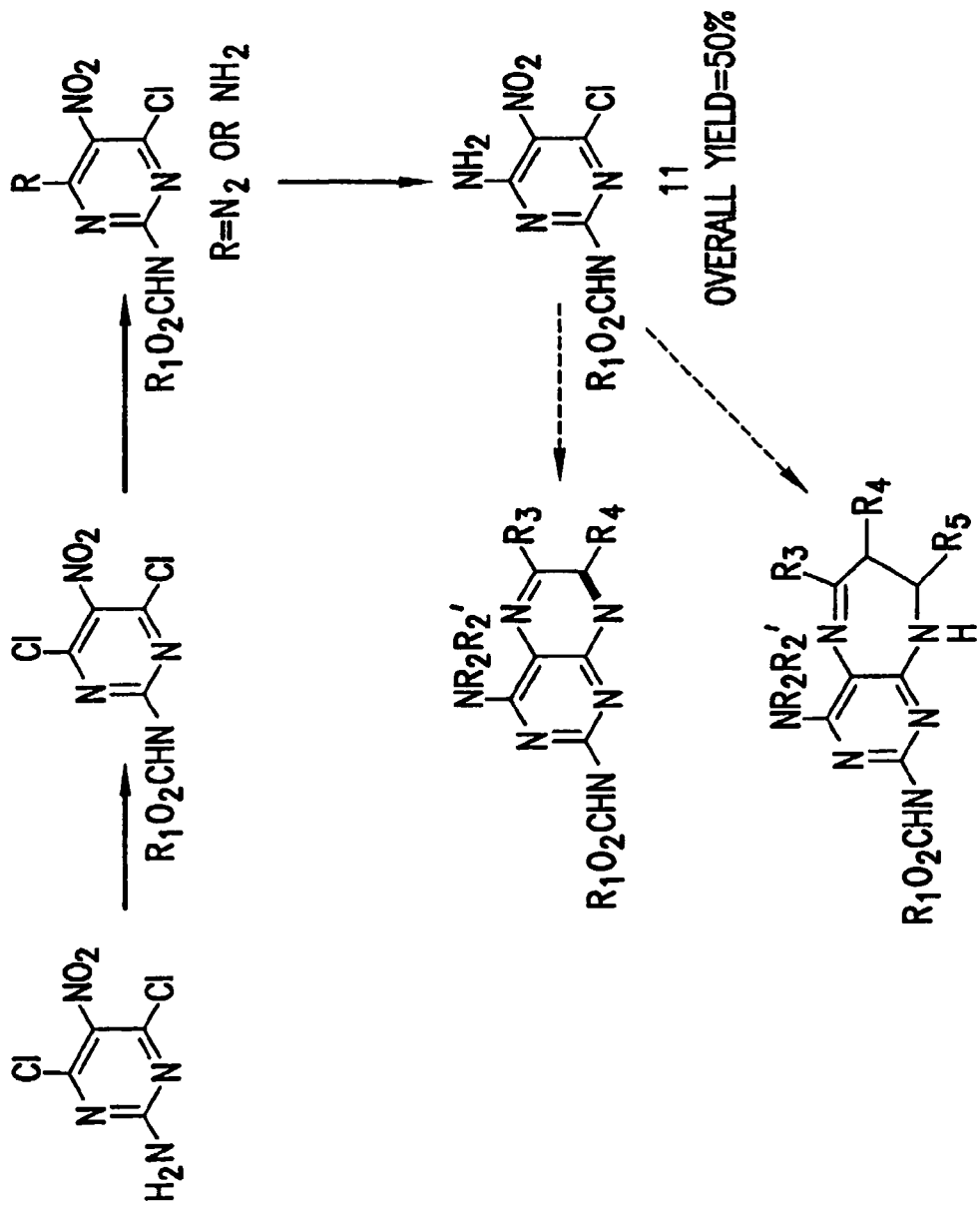
FIG. 8 shows one synthetic scheme for the synthesis of a key intermediate for the synthesis of aza analogues of 3-deazapteridine and pyridodiazepine compounds.

As shown in FIG. 8 the amino group of the 3-aminopropanol can react so as to displace the chloride substituent of the aromatic ring of compound 3, to yield compound 6. Other compounds analogous to compound 6 can be prepared by reacting the amino group of compound 3 with various organic and inorganic electrophiles, such as alkyl halides, acyl halides, epoxides, and the like. The nitro group of compound 6 and its analogs can be reduced to give an amine compound 6'. Compound 6' and it's analogs are members of the genus of compounds having Formula (III) disclosed above.

Oxidation of the hydroxyl group of compound 6 yields nitro-ketone 7, and reductive coupling of the 5-nitro group of the aromatic ring is followed by internal cyclization to form the diazepine ring. The potent compound SRI-7614 is a good example of the genus of diazapine compounds having structure 8 (R1=Et, R4, R5, R6=H). This reaction scheme can allow the preparation of a variety of compound having significant diversity at $R_1$, $R_4$, $R_5$, and $R_6$. Alterations at positions $R_4$, $R_5$, and $R_6$ can affect biological activity in view of the analogous effects in the 3-deazapteridine ring system appear to have a significant influence on biological activity and selectivity. and substitutions at the analogous amino group of the 3-deazapteridines also can significantly alter biological activity and selectivity (SRI-3072 & 4427-026-15).

The reactions leading to compound 8 shown in FIG. 8 may not readily allow alterations at the 4-amino group of the pyridine ring. In order to vary substitution at the amino group, hydrolysis of the amino group of compound 8 via diazotization followed by chlorodehydroxylation of the resulting hydroxyl group results in the chloro group of compound 10, which can then be displaced with various amines in order to obtain diversity at this position. The chloro groups in pyridines have typically been substituted with electron donating functional groups. Less nucleophilic amines may require harsh conditions. Some diversity at this position can be derived by the initial reductive amination of 3 before proceeding to make the diazepine ring system in 8. Interestingly, reductive amination with various amines on structure 8 can also be employed, but can yield over-reduced tetrahydro diazepines.

It can also be possible to change the 6-amino to a 6-chloro group in FIG. 8 (3) via a series of reactions exemplified by 8 to 10, by selectively displacing the 6-chloro in the presence of the 4-chloro group. Finally, as an alternative for generation of diversity at the critical 6-amino group, it can be possible to start with another pyridine carboxylic acid, citrazinic acid, by following a series of reactions detailed by Temple et al (*J. Med. Chem.* 30:1746-1751, 1987). The series of steps to form the pyridodiazepine system from citrazinic acid can be utilized to produce fully oxidized 1,5-diazepines, or 2,3-dihydro- or tetrahydro-1,5-diazepines. SRI-7614 is a 2,3-dihydrodiazepine.

Pyrimidine compounds of Formula (Ia) can also be synthesized. First, the preparation of the analogous key intermediate is much more facile (compare 3 versus 11 in FIG. 8) from a much cheaper starting material (Kuebrick et al., *J. Am. Chem. Soc.* 93:1214-1220, 1971). A small number of these aza analogs have been prepared at applicants' institution and screened for activity against tubulin. The pyrimidine analogues were found to be much less toxic than the corresponding deaza analogs, and acted similarly to the pyridodiazepines (structure 2 in FIG. 8) in terms of activity and toxicity.

The preparation of compounds represented by 1 is directly analogous to approaches outlined above. The preparation of the aza analog of 2 can require nitration of the dichloro analog, and displacement of one chloro group with a 3-aminopropanol analog. The remaining chloro group can be displaced with substituted amines, or the set of reactions can produce ring closure to the diazepine, followed by displacement of the chloro group with various amines.

As is understood by those of ordinary skill in the pharmaceutical arts and the art of synthetic organic chemistry, most or all of the compounds of the invention contain basic nitrogen atoms, which renders the compounds suitable for the ready preparation of salts of the compounds, including pharmaceutically acceptable salts, by the reaction of the nitrogen containing compounds with acids, such as HCl, H2SO4, lactic acid, succinic acid and the like, so as to form desirable salts that can be more easily dissolved in polar organic or aqueous carriers.

As is understood by those of ordinary skill in the art of synthetic organic chemistry, the various synthetic strategies, organic reactions, and/or functional group transformations utilized herein can be performed by a number of strategies, reactions, or procedures other than those explicitly described above. References for other synthetic procedures that can be utilized for the synthetic steps leading to the compounds disclosed herein can be found in, for example, March, J., *Advanced Organic Chemistry*, 4$^{th}$ Edition, Weiley-Interscience (1992); or Larock, R. C., *Comprehensive Organic Transformations, A Guide to Functional Group Preparations*, VCH Publishers, Inc. (1989), both incorporated herein by reference.

Bacterium

The bacterium targeted by the methods of the invention can be gram positive or gram negative. The gram positive bacterium can be selected from the group consisting of: *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinomyces israelii* and other *Actinomyces* species, and *Propionibacterium acnes*.

The gram negative bacterium can be selected from the group consisting of: *Clostridium tetani, Clostridium perfringens, Clostridium botulinum*, other *Clostridium* species, *Pseudomonas aeruginosa*, other *Pseudomonas* species, *Campylobacter* species, *Vibrio cholerae, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species, as well as other Enterobacteriacae, *Brucella abortus* and other *Brucella* species, *Burkholderia cepacia, Burkholderia pseudomallei, Francisella tularensis, Bacteroides fragilis, Fusobascterium nucleatum, Provetella* species and *Cowdria ruminantium*.

The above examples of gram positive and gram negative bacteria are not intended to be limiting, but are intended to be representative of a larger population including all gram positive and gram negative bacteria, as well as non-gram test responsive bacteria. Examples of other species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloio-* coccus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia, and Yokenella.

Permeability Enhancers

In one embodiment, the compound is modified or combined with other agents to promote permeability of the target bacterium. Prodrugs can be designed that allow for enhanced permeability. The compound can optionally be linked to a permeability enhancer, wherein the permeability enhancer allows the compound to cross the cell wall of the bacterium. By "linked" is meant chemically bound or conjugated to or part of compounds of Formula (1). The permeability enhancers might for example, be chemically linked to one of $S_1$, $S_2$, $S_3$, or $S_4$ radicals of the compounds of Formula (I). In the case of gram negative bacteria, the main component of the cell envelope is lipopolysaccharide (LPS). Alternatively, compositions comprising a compound of the invention and a permeability enhancer can be used. The LPS surface layer can act as a permeability barrier to some heterocyclic compounds in some strains of gram negative bacteria. There are, however, strains of gram negative bacteria which do not have a permeability barrier to the compounds. Examples include, but are not limited to, strains of bacteria containing the deep rough mutation (rfa), such as Salmonella typhimurium, Bordatella pertussis, B. parapertussis, and B. bronchiseptica (Allen et al. J. Bacteriol. 180 (1): 35-40, 1998.)

A "permeability enhancer" is defined as any substance or compound that is capable of enhancing the passage of a compound of the invention through the cell envelope of a bacterium. The permeability can be enhanced by more than 1%, more than 10%, more than 20%, more than 30%, more than 40%, more than 50%, more than 60%, more than 70%, more than 80%, more than 90%, more than 100%, more than 2 fold, more than 10 fold, more than 100 fold, or more than 1000 fold of the permeability of the cell before enhancement or as compared to a control. In one embodiment, the level of permeability can be tested by measuring the MIC of a population of bacterium after exposure to a permeability enhancer.

Examples of permeability enhancers include, but are not limited to, polymyxin B, cationic steroid antibiotics, surface active agents, defensins, other membrane active peptides (Evans et al. Vet Clin Pathol 24(4):109-116, 1995) and chelating agents (Suling et al. Antimicrob. Agents Chemother. 8:334-343, 1975). Some of the prodrug forms of the compounds of Formula (1), as defined elsewhere herein, can serve as permeability enhancers, such as for example the membrane active peptide types of prodrugs. Polymyxin B is a naturally occurring cyclic docapeptide isolated from Bacillus polymyxa (Tsubery et al. Mol Pharmacol. 62(5):1036-42, 2002.) Cationic steroid antibiotics selectively act upon the cell envelope to increase the envelope's permeability. (Qunying Guan et al., Organic Letters 2:2837-2840, 2000; Chunhong Li et al., J. Am. Chem. Soc. 120:2961-2962, 1997).

In one embodiment, permeability enhancers are used with the compound of the invention without being linked to the compound.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Anti-Tubercular Assay

Most anti-tubercular assays were conducted by the NIH Tuberculosis Antibacterial Acquisition and Coordination Facility (TAACF) screening facility against M. tuberculosis H37Rv (ATCC 27294; American Type Culture Collection, Manassas, Va.) using a BACTEC 460 radiometric system to determine the minimum inhibitory concentration ($MIC_{99}$). Rifampin was the positive control. The $MIC_{99}$ was also determined for SRI-7614 and SRI-3072 against strains of M. tuberculosis resistant to isoniazid, rifampin, ethambutol, kanamycin, pyrazinamide, thiacetazone, or cycloserine (Table 5). Concurrent with the determination of $MIC_{99}$, compounds were tested for cytotoxicity ($IC_{50}$) in Vero cells. After 72 h exposure, viability was assessed on the basis of cellular conversion of 3-(4,5-dimethylthiazol-2-yl)-5-(3-carboxymethoxyphenyl)-2-(4-sulfophenyl)-2H-tetrazolium salt (MTS) into a formazan product using the Promega CellTiter 96® $AQ_{ueous}$ Non-radioactive Cell Proliferation assay. The selectivity index (SI) of a compound is defined as the $IC_{50}$:$MIC_{99}$ ratio.

TABLE 5

Activity of SRI7614 and SRI-3072 against single drug resistant strains of *M. tuberculosis*

| | MIC (μg/mL) | | | | | | | |
|---|---|---|---|---|---|---|---|---|
| | WT | INH-R | RMP-R | EMB-R | KM-R | PZA-R | TAC-R | CS-R |
| SRI-7614 | 6.25 | 6.25 | 3.12 | 3.12 | 6.25 | 3.12 | 3.12 | 3.12 |
| SRI-3072 | 0.2 | 0.78 | ≦0.1 | ≦0.1 | ≦0.1 | | | |

WT = wildtype (H37Rv),
INH-R = isoniazid resistant,
RMP-R = rifampin resistant,
EMB-R = ethambutol resistant,
KM-R = kanamycin resistant,
PZA-R = pyrazinamide resistant,
TAC-R = thiacetazone resistant,
CS-R = cycloserine resistant MIC/MBC of SRI-3072 for *M. tuberculosis* H37Ra The MIC of SRI-3072 was determined for *M. tuberculosis* H37Ra (ATCC 25177) as described elsewhere (Suling et al. *Journal of Antimicrobial Chemotherapy* 42, 811-815, 1998; Suling et al. Antimicrobial Agents and Chemotherapy 44, 2784-2793, 2000) using a colorimetric (alamar blue) microdilution broth assay. The compound was dissolved in DMSO and diluted serially in two-fold increments in 7H9 broth supplemented with ADC enrichment and 0.2% glycerol (assay medium). The final amount of DMSO in each dilution was 1.3%. SRI-3072 was assayed in quadruplicate. Medium, drug and viability controls were incorporated in the assay. Ethambutol was the positive control and had a MIC of 2 μg/ml. The bactericidal activity of SRI-3072 was determined just prior to the addition of the redox dye to the plate after six days of incubation. At that time, the plate was examined visually. Each well with no visible growth was mixed by carefully drawing liquid in and out of a microliter pipetter and plated (10 μL) onto 7H11 agar. The plates were incubated for 21 days in polyethylene bags at 36-37° C. and the colonies counted with the aid of a dissecting microscope. The counts were compared to those of the initial inoculum to calculate the percent survivors and the $\log_{10}$ reduction in survivors. The MBC was defined as the lowest drug concentration that reduced the cfu by $2\text{-}\log_{10} \pm SD$ (N=4).

Activity of SRI-3072 in *M. tuberculosis*-infected Macrophages

SRI-3072 was assayed at 0.25, 1, 4 and 16 times the MIC (0.2 μg/ml) through the TAACF for activity against *M. tuberculosis* Erdman (ATCC 35801) in monolayers of mouse bone marrow macrophages as described previously (Kelly et al. *Anti. Agents & Chemo.* 44:2784-2793, 1994). Activity was reported as the lowest drug concentration yielding a 90% ($EC_{90}$) and 99% ($EC_{99}$) reduction in cfus after seven days relative to drug-free controls. Toxicity was determined by visual inspection.

EXAMPLE 2

Purification and Characterization of FtsZ from *M. tuberculosis*

The purification of FtsZ was performed as described previously (White et al. *J. Bact.* 182:4028-4034, 2000). The *M. tuberculosis* FtsZ coding sequence was subcloned into the NcoI site of pET15b (Novagen). This plasmid, pJD168, was used to transform *E. coli* BL21 (DE3)/pLysS. Cells were incubated at 32° C. in LB media containing 0.4% glucose for 1 h. Five hundred μl of transformed cells were added to 250 ml of fresh LB media containing 0.4% glucose, 100 μg/ml ampicillin, and 34 μg/ml chloramphenicol and incubated overnight at 32° C. The cells were pelleted by centrifugation at room temperature. The cells were resuspended in four liters of prewarmed LB media containing 0.2% glucose, 100 μg/ml ampicillin, and 34 μg/ml chloramphenicol; the culture was shaken with good aeration at 32° C. When the culture reached an $A_{600}$ of ~0.4, expression of FtsZ was induced with 1 mM isopropyl β-D-thiogalactoside. Cells were harvested 3 h later, chilled (8-10° C.) quickly, centrifuged, washed with ice-cold phosphate-buffered saline, repelleted, and stored at −80° C.

The following procedures were performed at 4° C. The frozen cell pellet from 1 liter of *E. coli* culture was resuspended in 30 ml of lysis buffer (20 mM sodium phosphate buffer, pH 7.8, 500 mM NaCl, 2 mM PMSF, 4 μg/ml pepstatin A, 4 μg/ml leupeptin, 1 mM benzamidine, and 20 μg/ml soybean trypsin inhibitor) and sonicated briefly to loosen the gum-like pellet. The cell suspension was digested for 30 min with 1 mg DNAse and then extracted by two passes through a French press at 15,000-20,000 lb/in². The solution was clarified by centrifugation at 27,000 g for 20 min and then applied to a $Ni^{2+}$-agarose cartridge (Pharmacia) equilibrated with 10 mM imidazole, 20 mM sodium phosphate, 0.5 M NaCl, pH 7.8. The column was washed with 15 ml of equilibration buffer containing 100 mM imidazole. Recombinant FtsZ was eluted with 5 ml of equilibration buffer containing 250 mM imidazole. The eluate was immediately passed over Sephadex G-25 columns (PD-10, Pharmacia) equilibrated with 25 mM HEPES-NaOH (pH 7.2), 100 mM KCl, 0.1 mM EDTA, 1 mM DTT, and 10% glycerol. The N-terminal $His_6$ tag was removed by digestion on ice for 2 h with 0.5 units of thrombin (Sigma)/ml FtsZ. Thrombin was removed by passing the sample over a benzamidine-agarose column (Sigma, flow rate ~1 ml/min) equilibrated with desalting buffer. The FtsZ was polymerized under conditions that gave stable polymers (i.e. no salt, 1 mM GTP) centrifuged at 100,000 g to precipitate the polymers, depolymerized by resuspending the pellet in buffer containing 150 mM KCl, and finally centrifuged a second time at high speed to remove any aggregates. Protease inhibitors (2 mM 1,10-phenanthroline, 20 µg/ml soybean trypsin inhibitor, 4 µg/ml pepstatin A, 10 µg/ml APMSF, 50 µg/ml aprotinin, 2 mM PMSF, 4 µg/ml leupeptin, 40 µg/ml TLCK, and 1 mM benzamidine) were added to the pooled fractions. The sample was applied to a gel filtration column (Pharmacia HiLoad 26/60 Superdex 200 prepgrade) equilibrated with 25 mM HEPES-NaOH (pH 7.2), 1 mM EDTA, 50 mM KCl, 1 mM DTT, and 10% glycerol. Absorbance was monitored at 280 nm. The protease cocktail was added to the pooled fractions. After concentration (Millipore BioMax 15-1000) to 20 mg/ml, the sample was dialyzed against 25 mM HEPES-NaOH (pH 7.2), 1 mM DTT, 0.1 mM EDTA, and 10% glycerol. The protease cocktail was added a third time and the protein stored at −80° C.

The majority of FtsZ eluted from the column in a single peak corresponding to a molecular weight of 95,500 daltons. The fractions from the peak were pooled, concentrated, dialyzed against buffer containing 10% glycerol, and stored in aliquots at −80° C. Under these conditions the protein was stable for several months. A typical yield from a 1-1 $E.$ $coli$ culture was 30 mg of FtsZ.

The molecular weight of FtsZ, determined by 15% SDS-PAGE, was 45,700 daltons. Mass spectrometric analysis (MALDI-TOF) confirmed that it had the correct mass (observed, 39,064.30; calculated, 39,036.45; masses include an N-terminal Gly-Ser-His that remains after thrombin digestion). N-terminal sequencing confirmed the expected sequence of GSHMTPPHNY. FtsZ eluted from a gel filtration column as a series of aggregates of decreasing molecular weight from ~2,000,000 Da (void volume) to 95,500 Da (major peak). Since the subunit molecular weight is 39,036 Da, the 95,000-Da peak is likely a FtsZ dimer. Under similar conditions (no nucleotide or $Mg^{2+}$), $E.$ $coli$ FtsZ has been shown by analytical ultracentrifugation and chemical cross-linking to exist as a mixture of ~70% dimer, 15% trimer, and 15% monomer. $M.$ $jannaschii$ FtsZ has also been reported to exist as an oligomer.

Purified FtsZ (5 µM) had GTPase activity, converting around 6.9 nmol of GTP to GDP per mg of FtsZ per hour. Unlike $E.$ $coli$ FtsZ, heating $M.$ $tuberculosis$ FtsZ did not increase the GTPase activity. GDP was bound at a ratio of 1:1 moles of GDP/mole FtsZ, about the same ratio as that found for $E.$ $coli$ FtsZ. Since the GTPase activity is cooperative, it is difficult to make direct comparisons between the published specific activity of $E.$ $coli$ FtsZ and our specific activity for $M.$ $tuberculosis$ FtsZ of 6.9 nmol $mg^{-1}$ $hour^{-1}$. However, it appears that $M.$ $tuberculosis$ FtsZ hydrolyzes GTP at a significantly slower rate than $E.$ $coli$ FtsZ, which has been reported to have a $V_{max}$ of 30 µmol $mg^{-1}$ $hr^{-1}$.

EXAMPLE 3

Light Scattering Assay for FtsZ Polymerization

The polymerization and depolymerization of purified FtsZ was followed by the method described by Mukherjee and Lutkenhaus for $E.$ $coli$ FtsZ ($J.$ $Bact.$ 181:823-832, 1999). Light scattering was measured in a thermostatically (30° C.) controlled Aminco-Bowman series 2 luminescence spectrometer using 0.5 ml quartz cuvets (cell 2×10 mm, Hellma). Excitation and emission wavelengths were 400 nm with a slit width of 2 nm. The gain was typically set at 540 V but was increased if needed to give a maximum response around 8. FtsZ (500 µg/ml; 13 µM) was incubated in 50 mM MES-NaOH pH 6.5, 100 mM KCl, and 5 mM $MgCl_2$ to establish a baseline. GTP (40 µM) was added (final volume 300 µl) and the increase in light scattering measured for an additional 50-60 min. Changes in concentrations of a component for a particular experiment are indicated in the text or figure legend.

EXAMPLE 4

Characterization of $M.$ $tuberculosis$ FtsZ with Light Scattering Assay $M.$ $tuberculosis$ FtsZ polymerization was measured using the conditions described for $E.$ $coli$ FtsZ. FtsZ (10 uM) was incubated at 30° C. in 50 mM MES-NaOH, pH 6.5, containing 10 mM $MgCl_2$, and 25 mM KCl. There was an immediate increase in light scattering upon addition of 1 mM GTP, reaching a plateau in about 10 min. The light scattering was remarkably stable, dropping by <10% in 5 h. Once polymerization had occurred, neither increasing the temperature to 45° C. nor lowering it to 1° C. induced depolymerization (data not shown). However, addition of 20 mM EDTA caused the light scattering to immediately return to baseline. FtsZ could be re-polymerized, as measured by an increase in light scattering, by adding 25 mM $MgCl_2$ to the reaction.

Polymerization and depolymerization of $M.$ $tuberculosis$ FtsZ is clearly much slower than that of $E.$ $coli$ FtsZ. Polymerization occurs very rapidly for $E.$ $coli$ FtsZ (<30 s), with a stable phase lasting about 15 min, followed by complete depolymerization within another 10 min. Under identical conditions, $M.$ $tuberculosis$ FtsZ takes about 10 min to reach maximum polymerization followed by a stable phase lasting at least 5 hours, kinetics that are more similar to mammalian tubulin. Unlike tubulin, however, FtsZ could not be depolymerized by a temperature shift to 1° C. It is tempting to speculate that the slower dynamics of $M.$ $tuberculosis$ FtsZ, compared to $E.$ $coli$ FtsZ, are related to its lower GTPase activity. Perhaps the rates of polymerization and depolymerization of FtsZ are proportional to the growth rate of the organism. $E.$ $coli$, with its much faster cell division time, may need a more dynamic cell division protein than the slower growing $M.$ $tuberculosis$. Polymerization and depolymerization were dependent on the concentration of GTP used to initiate the reaction. With 5 mM $MgCl_2$, 0.2-1 mM GTP initiated an increase in light scattering that was still increasing 25 min after addition. Lower concentrations of GTP (0.05-0.1 mM) resulted in both polymerization and depolymerization within 25 min. No increase in light scattering was seen when either 1 mM GDP or 5'-guanylylimidodiphosphate (GMP-PNP), a nonhydrolyzable GTP analog, replaced GTP.

Since the rate of GTP hydrolysis by *E. coli* FtsZ is affected by the KCl concentration (Mukherjee et al. *Proc. Natl. Acad. Sci.* 90:1053-1057, 1993), the effect of KCl on polymerization of *M. tuberculosis* FtsZ was examined. With 10 or 50 mM KCl, addition of GTP started an increase in light scattering that continued for 1 h. Without KCl, polymerization was slower than with low KCl but was still continuing at the end of 1 h. Higher concentrations of KCl (100 and 200 mM) led to an increase in light scattering followed by a decrease. The maximum amount of light scattering decreased with increasing KCl concentration. The effect on depolymerization by KCl appears to be specific, since in the presence of 100 or 200 mM NaCl polymerization was still increasing at 1 h. *E. coli* FtsZ GTPase activity can be stimulated by KCl but not NaCl and increasing the KCl concentration is associated with a shortening of the steady state phase of polymerization.

*M. tuberculosis* FtsZ, like other GTPases, requires $Mg^{2+}$ for hydrolysis of GTP to GDP. As $MgCl_2$ was increased from 1 to 5 mM, there was an augmentation in the maximum polymerization of *M. tuberculosis* FtsZ followed by a return to baseline. Above 5 mM $MgCl_2$, only polymerization was observed. FtsZ did not polymerize in the absence of $MgCl_2$. This is in contrast to *E. coli* FtsZ, in which the addition of GTP in the absence of $MgCl_2$ produces an increase in light scattering approximately one-third the level obtained with 10 mM $MgCl_2$.

Examination of light scattering as a function of FtsZ concentration allowed determination of the minimum concentration of protein required for polymerization. FtsZ at different concentrations was incubated in polymerizing buffer containing 100 mM KCl and 5 mM $MgCl_2$. After the addition of 0.05 mM GTP, the maximal amount of light scattering was measured and plotted against the FtsZ concentration. The value for the critical concentration required for polymerization was 3 M (120 g/ml). This is slightly higher than the critical concentration for *E. coli* FtsZ, determined by sedimentation to be 1.5 M, but is similar to the value of 2.5 M obtained from a light scattering assay.

*M. tuberculosis* FtsZ polymerization was markedly reduced at neutral or alkaline pH. GTP-dependent polymerization was followed at pH 6.5, 7.0 and 7.4 in a buffer system that maintained constant ionic strength over this range (50 mM HEPES, 50 mM MES, 100 mM ethanolamine). The maximum light scattering at pH 7.0 was less than one-quarter of that at pH 6.5. No polymerization was seen at pH 7.5. *E. coli* FtsZ appears to be more tolerant of pH changes.

EXAMPLE 5

Inhibitor Studies

The effect of different compounds on *M. tuberculosis* FtsZ polymerization and depolymerization (Table 6) was monitored using the light scattering assay described above. Compounds were added to the reaction and a baseline established. GTP was added to initiate polymerization and light scattering data were collected for an additional 50-60 min. The maximum light scattering was calculated by subtracting the baseline value before GTP from the peak value. The % control activity was calculated by comparison with an assay without compound. When DMSO was used as solvent, the control also contained the same amount of DMSO (2%). Compounds were initially evaluated at 100 µM. If inhibition was observed, then the compounds were retested at several concentrations. A semi-log plot of % control activity vs. compound concentration was used to calculate the 50% inhibition concentration. Three independent curves were run for each compound. Colchicine was purchased from Sigma. The GTP initiated polymerization of purified bovine tubulin (Sigma) was followed by a light scattering assay. Bovine tubulin (I mg/mL; 20 M) was incubated in 100 mM MES-NaOH, pH 6.5, 1 mM EGTA, 100 µM EDTA, 2 M glycerol, and 0.5 mM $MgCl_2$ plus inhibitor or solvent to establish a baseline. GTP (1 mM) was added (final volume 500 L) and the increase in light scattering was measured for an additional 50-60 min. The maximum light scattering was calculated by subtracting the baseline value from the peak value. When DMSO was used as solvent, the control also contained the same amount of DMSO (2%). Compounds were initially evaluated at 100 µM. If inhibition was observed, then the compounds were retested at several concentrations. The $ID_{50}$ value and percent inhibition were calculated as described above.

TABLE 6

Activity of SRI7614 and SRI-3072 against FtsZ Activity and Tubulin Activity

| | *M. tuberculosis* FtsZ | | Bovine Brain Tubulin |
|---|---|---|---|
| Compound | Polymerization $ID_{50}$ (µM) | GTP Hydrolysis % Inhibition (100 µM) | Polymerization $ID_{50}$ (µM) |
| Colchicine | 104 ± 2 µM | 35% | 6.5 µM |
| SRI-3072 | 52 ± 12 µM | 20% | no inhibition (100 µM) |
| SRI-7614 | 60 ± 0 µM | 25% | 4 µM |

EXAMPLE 6

Mass Spectrometry and Amino Acid Sequencing

MALDI-TOF mass spectra were obtained on a Voyager Elite mass spectrometer (positive mode) with delayed extraction technology (PerSeptive Biosystems). The acceleration voltage was set at 25 kV and 10-50 laser shots were summed. The matrix was sinapinic acid (Aldrich) dissolved in $CH_3CN$-0.1% $CF_3CO_2H$ (1:1). The spectrometer was calibrated with apomyoglobin. Samples were diluted 1:10 with matrix before pipetting 1 µl onto a smooth plate. N-terminal sequencing was done by automated Edman degradation on a gas-phase microsequencing system (Model P1 2090E, Beckman). The amino acid residue released in a given cycle was identified from the difference chromatogram (comparison with the previous cycle).

EXAMPLE 7

Antibacterial Activity Against a Panel of Bacteria

A microdilution broth assay was used to determine the MIC. SRI-3072 was dissolved in DMSO and then diluted in serial two-fold dilutions in assay medium (Mueller-Hinton broth). The final DMSO amount in the medium was 1.3% and had no affect on the growth of the panel of organisms (Table 7). The drug dilutions (50 µl) were added to appropriate wells of 96-well (U-shaped) plates. Inocula of the test organisms were prepared by inoculating Mueller-Hinton broth with growth from fresh slant cultures followed by incubation at 37 degrees C. for 5-6 hr at which time the growth was measured turbidmetrically. Each culture was then diluted in medium to a turbidity equivalent of about $1 \times 10^6$ CFU/ml and used as an inoculum (50 µL/well). The assay plates also contained viability controls, and uninoculated medium and drug controls. Trimethoprim was used as a positive drug control and had MICs in the range of 0.13 to >16 µg/ml for the trimethoprin-resistant strains. The plates were incubated for 18-20 hr and the wells examined visually for growth. The MIC was defined as the highest drug dilution that results in no visible growth. SRI-3072 was assayed against *Escherichia coli*, *Enterococcus hirae*, and *Staphylococcus aureus*, representing a Gram negative rod and Gram positive cocci, respectively. The drug was not active against *E. coli* and had moderate activity against the two cocci (MIC of 32 µg/mL). The drug was then tested against an expanded panel of Gram positive rods and cocci, which included methicillin-resistant staphylococci, multi-drug-resistant staphylococci and vancomycin-resistant enterococci. MICs against these organisms were uniformly in the range of 32-64 µg/mL except for the single Gram positive rod tested, *Bacillus subtilis*, which was inhibited at an MIC of 16 µg/mL. Since the drug was not active against *E. coli*, another gram negative rod, *S. typhimurium* was tested. This particular strain of *S. typhimurium* contained a deep rough (rfa) mutation in the polysaccharide side chain of the LPS component of the cell envelope. Such strains possess an increased permeability to heterocyclic compounds. SRI-3072 was active against this gram negative mutant. In conclusion, SRI-3072 was not active against the single Gram-negative bacterial representative but did have moderate activity against several Gram-positive bacteria, including drug resistant strains. Also, the deep rough mutant was susceptible to SRI-3072, indicating that the lack of activity of *E. coli* was due to permeability rather than a lack of effect on *E. coli*.

TABLE 7

MIC of SRI 3072 for Representative Gram Positive and Gram Negative Bacteria

| Organism | Strain Properties | MIC (µg/mL) |
|---|---|---|
| *Escherichia coli* SRI 1218 | Wild type | >64 |
| *Salmonella typhimurium* SRI 993 | Deep rough mutant | 64 |
| *Staphylococcus aureus* SRI 1323 | Wild type | 32 |
| *S. aureus* SRI 1186 | Wild type | 32 |
| *S. aureus* SRI 1343 | Multi-drug resistant | 64 |
| *S. aureus* SRI 1279 | Methicillin resistant | 64 |
| *S. epidermidis* SRI 1296 | Trimethoprim resistant | 32 |
| *Enterococcus hirae* SRI 76 | Wild type | 32 |
| *E. faecalis* SM 1414 | Vancomycin resistant | 64 |
| *E. faecalis* SRl 1295 | Wild type | 64 |
| *E. faecium* SRI 1421 | Vancomycin resistant | 32 |
| *Bacillus subtilis* SRI 1032 | Wild type | 16 |

EXAMPLE 8

Effect of Compounds on Cell Machinery

Figure 9:
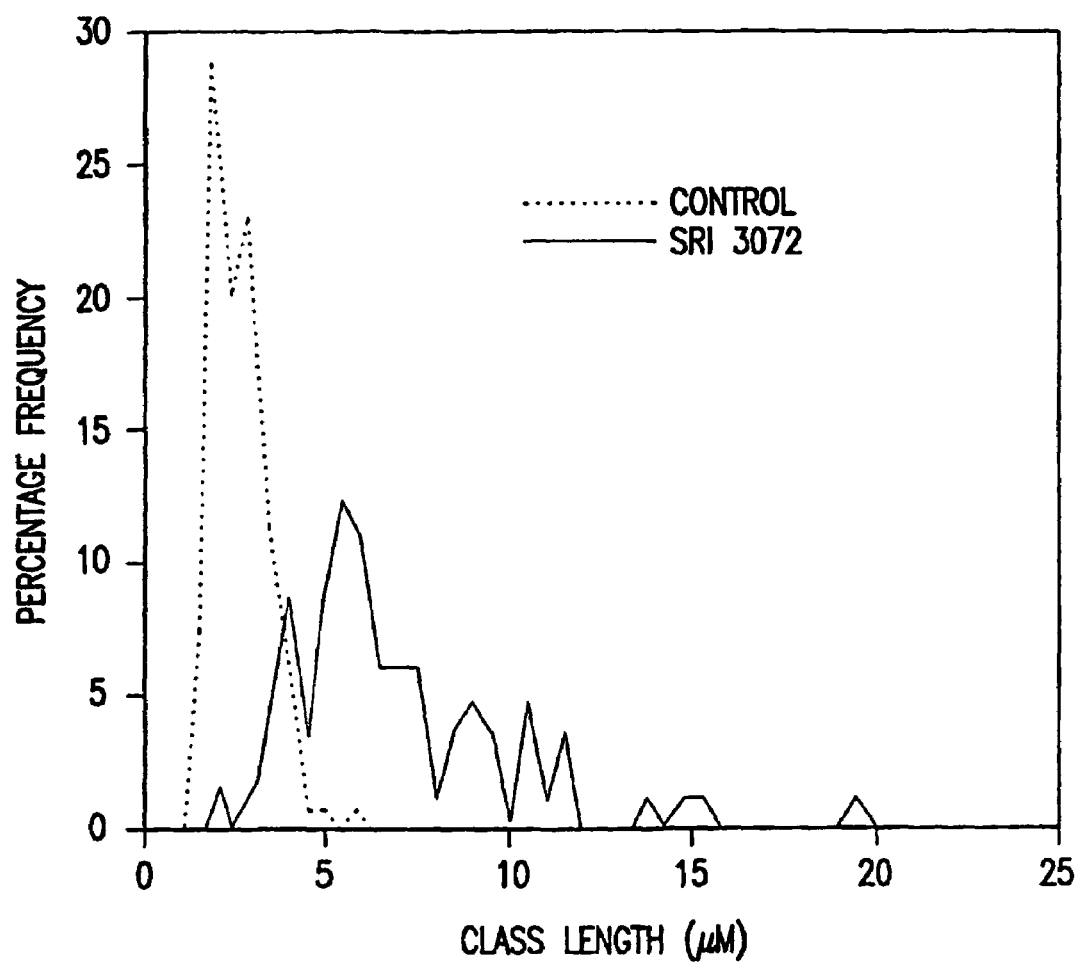
FIG. 9 shows the effect of SRI-3072 on cell length.

The effect of SRI 3072 on the cell division machinery of *Mycobacterium bovis* (BCG) was examined. (FIG. 9). BCG is an excellent surrogate for *M. tuberculosis* since their genome's are approximately 95% identical. BCG expressing green fluorescent protein was incubated with 0.3 µg/ml SRI 3072 (a sub-MIC concentration) for 5 days and assayed for cell length. The cells were spun down and washed in PBS, then air dried onto poly-1-lysine coated coverslips. DAPI (3 µg/ml) in 50% glycerol was pipetted onto the coverslip and inverted onto the slide. The slides were viewed on a Nikon eclipse microscope equipped with a DXM 1200 color CCD. Images were grabbed with Lucia G software version 4. Phase contrast images with fluorescence were taken. The control cells have a rather narrow cell length clustered around 2-3 µm. Whereas, those treated with SRI 3072 are much longer and branched. Unlike the control cells, the DNA in the SRI 3072-treated cells is dispersed throughout the abnormal cells. SRI 3072 disrupts the cell division machinery. Furthermore, when the cultured cells are washed to remove SRI 3072 from the media, they do not recover.

EXAMPLE 9

The GTPase activity of 25 µl of sample containing FtsZ was monitored using the method described by Mukherjee et al. (*Proc. Natl. Acad. Sci.* 90:1053-1057, 1993). Briefly, FtsZ was incubated at 30° C. with 40 µM [$\gamma$-$^{32}$P]GTP (250-400 cpm/pmol), 100 mM MES-NaOH, pH 6.5, 100 mM KCl, and 5 mM MgCl$_2$, for 60 mm (final volume 50 µl) Radioactive inorganic phosphate was extracted with 0.1 M HClO$_4$ containing 1 mM KH$_2$PO$_4$ followed by the addition of sodium molybdate and isopropyl acetate. Aliquots of the organic phase were measured in a liquid scintillation counter. Discontinuous sodium dodecyl sulfate-polyacrylamide gel electrophoresis (15% gel) was used to monitor the purification and to determine subunit molecular weight. Protein concentrations were determined by the Bradford procedure, using bovine gamma globulin as the standard. The amount of nucleotide bound to the protein (50 µM FtsZ) was determined from a 3% perchloric acid extract (Sossong et al. Biochem. 38: 14843-50, 1990). The supernatant was read at 257 nm and the concentration calculated from a standard curve of GDP (5-200 µM). Strong anion exchange HPLC was used to identify the nucleotide.

The disclosures of any referenced publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the claims.

EXAMPLE 10

The following compounds (Table 8) are examples of compounds of the invention, as well as their inhibitory concentrations.

TABLE 8

| Compound # | Structure | % Inh | MIC (µg/mL) | IC50 (µg/mL) | SI |
|---|---|---|---|---|---|
| A1 | 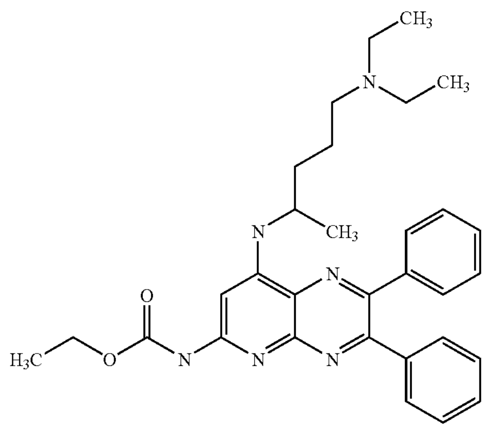 | 100 | 0.2 | 4.3 | 21.5 |
| A2 | 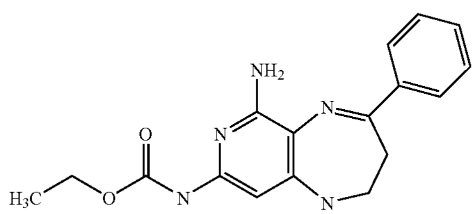 | 100 | 6.25 | >200 | >32 |
| A3 | 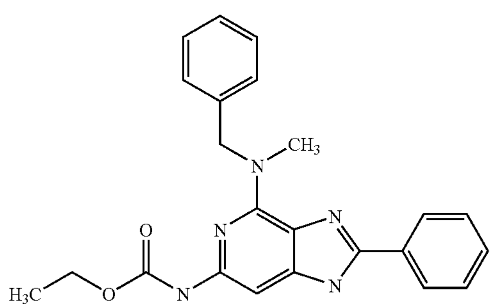 | 99 | | | |
| A4 | 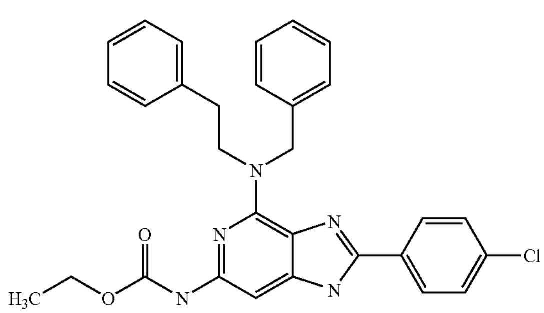 | 99 | | | |

TABLE 8-continued
| Compound # | Structure | % Inh | MIC (µg/mL) | IC50 (µg/mL) | SI |
|---|---|---|---|---|---|
| A5 | 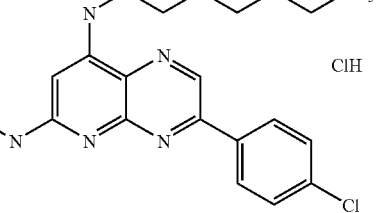 | 99 | 1.56 | | |
| A6 | 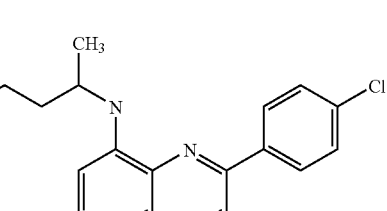 | 99 | 1.56 | | |
| A7 | 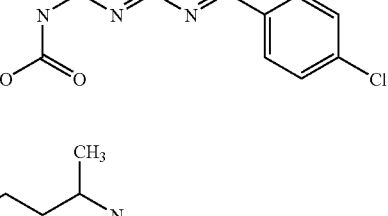 | 99 | 3.13 | 1.89 | 0.6 |
| A8 | 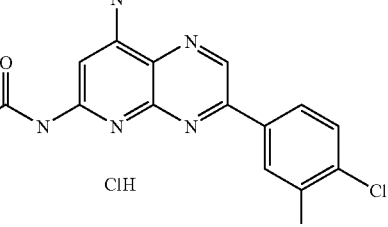 Chiral | 99 | 6.25 | | |
| A9 | 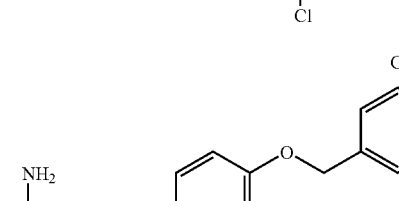 Chiral | 99 | 6.25 | | |

TABLE 8-continued

| Compound # | Structure | % Inh | MIC (μg/mL) | IC50 (μg/mL) | SI |
|---|---|---|---|---|---|
| A10 | 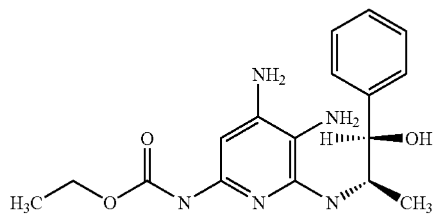 | 99 | 12.5 | >200 | >16 |
| A11 | 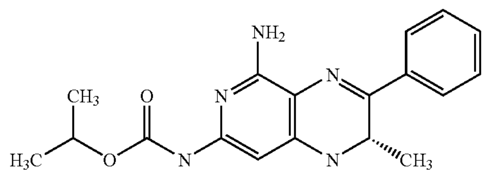 | 99 | 12.5 | 1.51 | 0.12 |
| A12 | 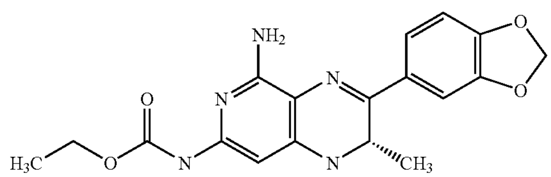 | 99 | 12.5 | 1.51 | 0.12 |
| A13 | 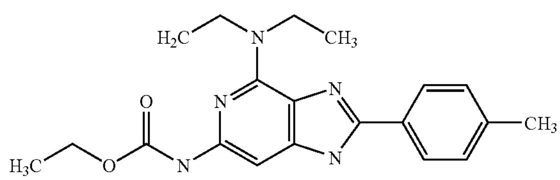 | 98 | | | |
| A14 | 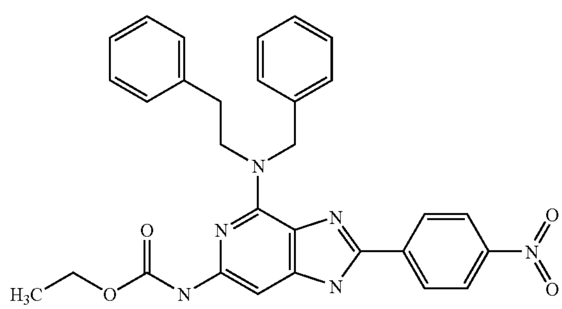 | 98 | | | |
| A15 | 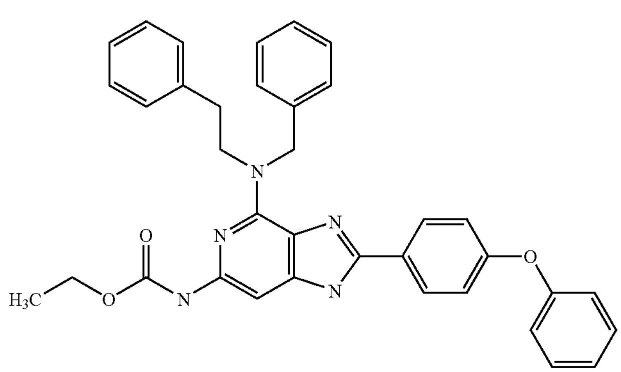 | 98 | | | |

TABLE 8-continued

| Compound # | Structure | % Inh | MIC (μg/mL) | IC50 (μg/mL) | SI |
|---|---|---|---|---|---|
| A16 | 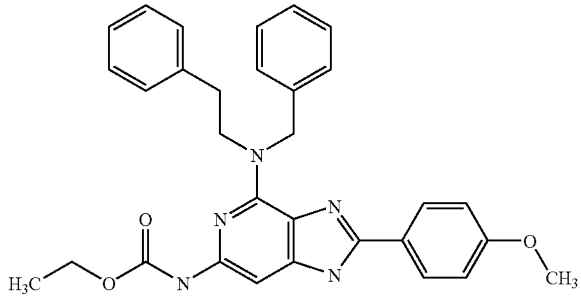 | 98 | | | |
| A17 | 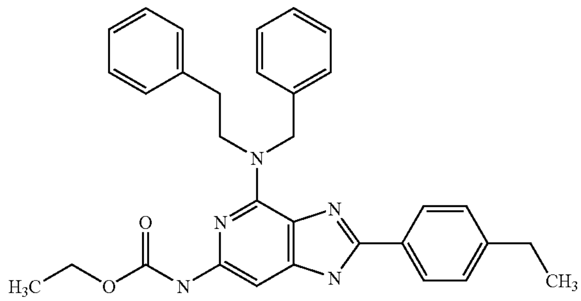 | 98 | | | |
| A18 | 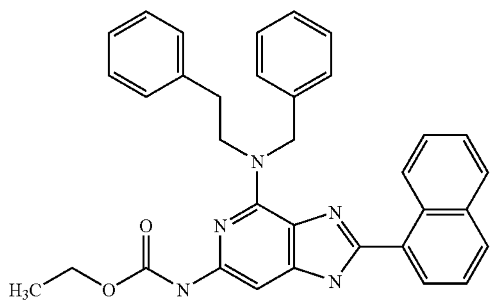 | 98 | | | |
| A19 | 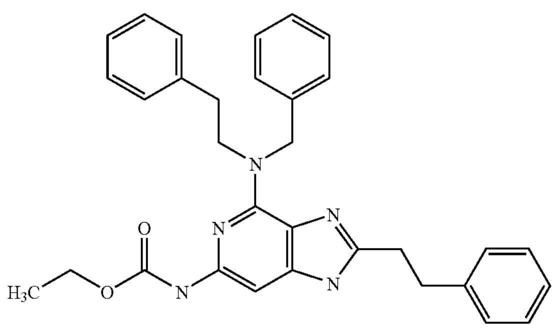 | 98 | | | |
| A20 | 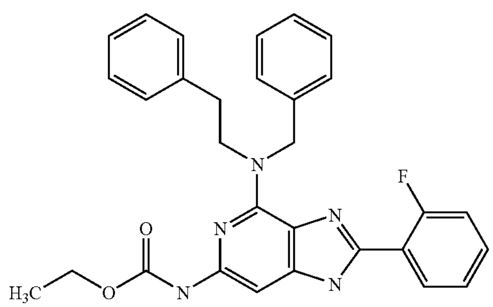 | 98 | | | |

TABLE 8-continued

| Compound # | Structure | % Inh | MIC (μg/mL) | IC50 (μg/mL) | SI |
|---|---|---|---|---|---|
| A21 | 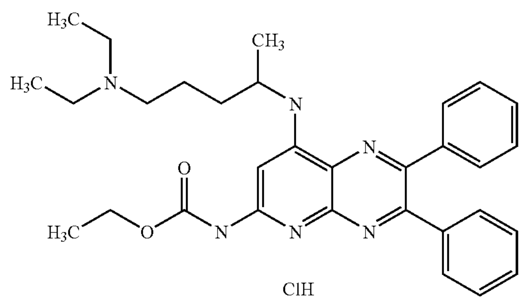 | 98 | 0.1 | 8.3 | 83 |
| A22 | 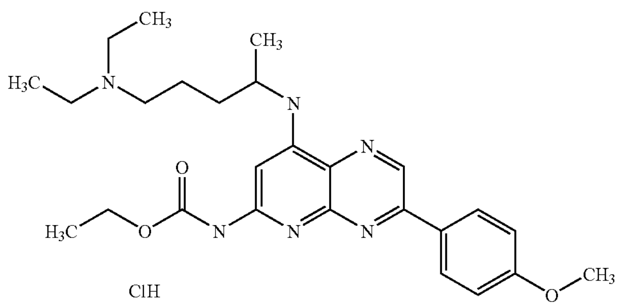 | 98 | 1.56 | 8.7 | 5.58 |
| A23 | 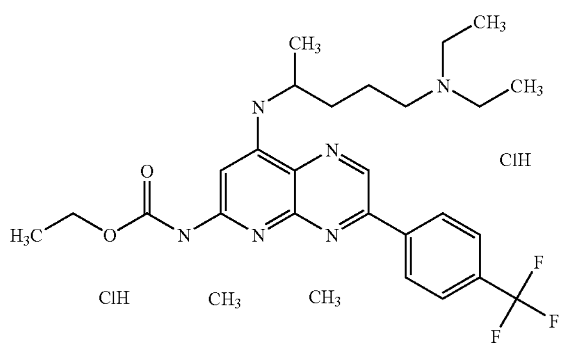 | 98 | 6.25 | 1.6 | 0.26 |
| A24 | 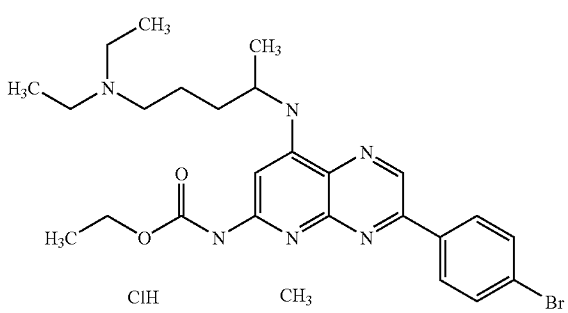 | 98 | 6.25 | 1.39 | 0.22 |
| A25 | 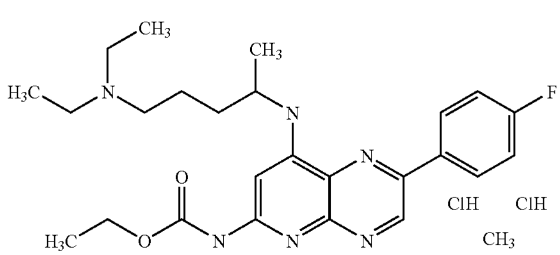 | 98 | 12.5 | 6.8 | 0.54 |

TABLE 8-continued
| Compound # | Structure | % Inh | MIC (μg/mL) | IC50 (μg/mL) | SI |
|---|---|---|---|---|---|
| A26 | 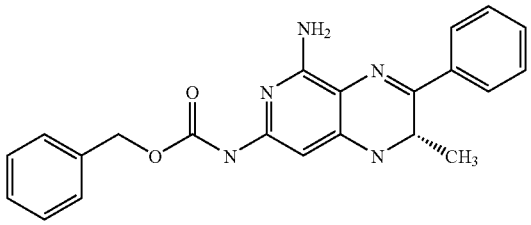 | 98 | 12.5 | 1.51 | 0.12 |
| A27 | 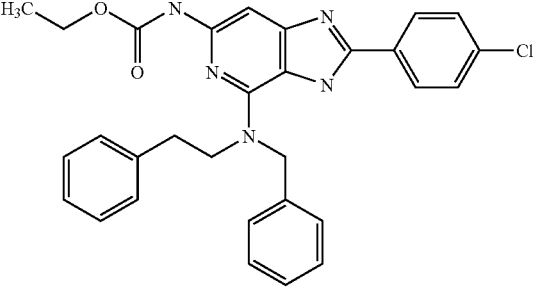 | 97 | | | |
| A28 | 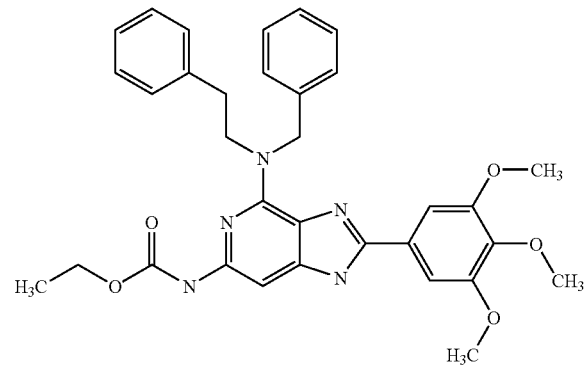 | 97 | | | |
| A29 | 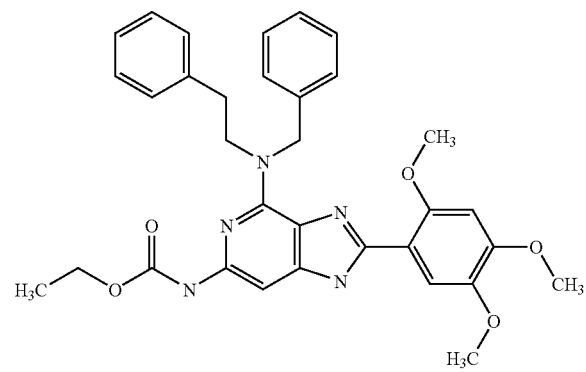 | 97 | | | |

TABLE 8-continued

| Compound # | Structure | % Inh | MIC (μg/mL) | IC50 (μg/mL) | SI |
|---|---|---|---|---|---|
| A30 | 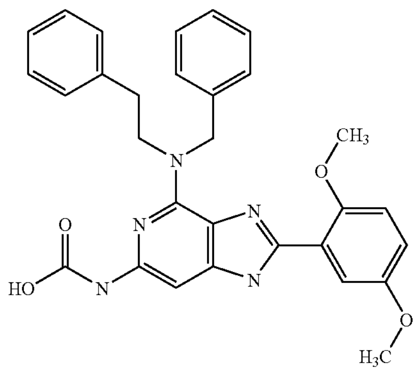 | 97 | | | |
| A31 | 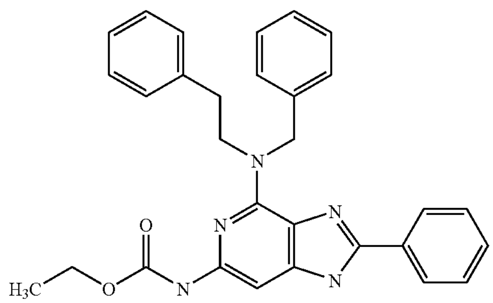 | 97 | | | |
| A32 | 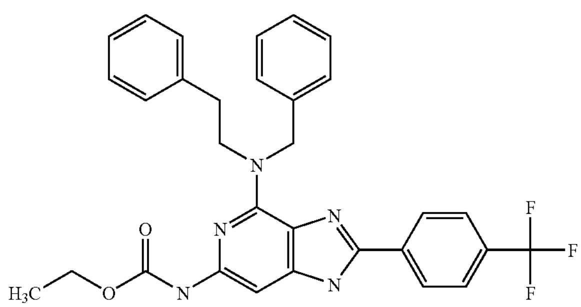 | 97 | | | |
| A33 | 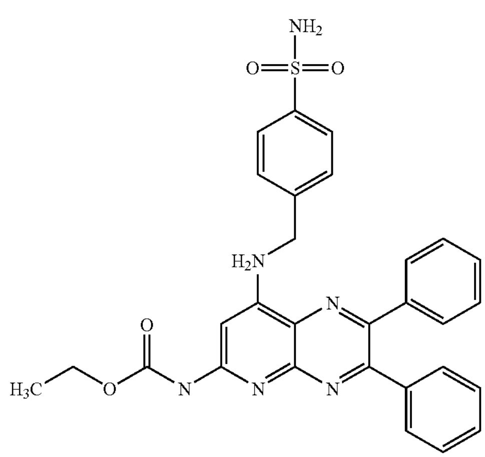 | 97 | 0.39 | >6.25 | >16 |

TABLE 8-continued
| Compound # | Structure | % Inh | MIC (μg/mL) | IC50 (μg/mL) | SI |
|---|---|---|---|---|---|
| A34 | 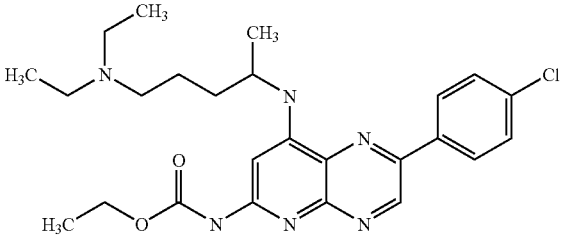 | 97 | 6.25 | 2.28 | 0.36 |
| A35 | 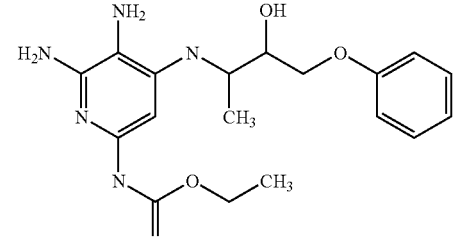 | 97 | 12.5 | >1000 | >80 |
| A36 | 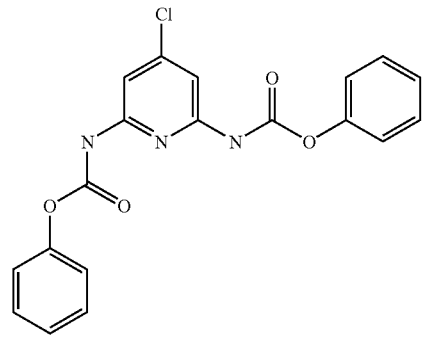 | 97 | 12.5 | | |
| A37 | 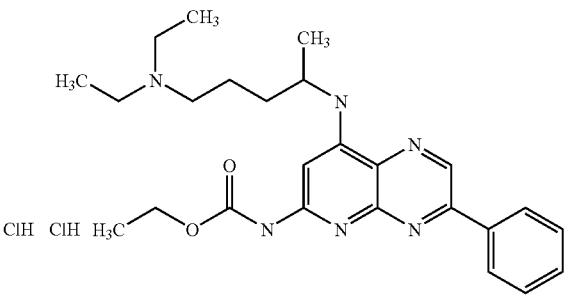 | 96 | 12.5 | | |
| A38 | 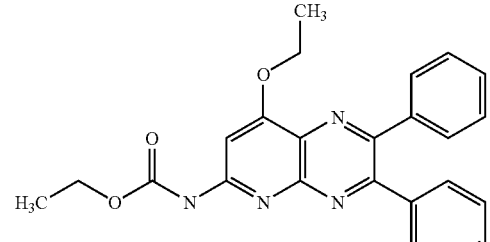 | 95 | | | |

TABLE 8-continued

| Compound # | Structure | % Inh | MIC (µg/mL) | IC50 (µg/mL) | SI |
|---|---|---|---|---|---|
| A39 | 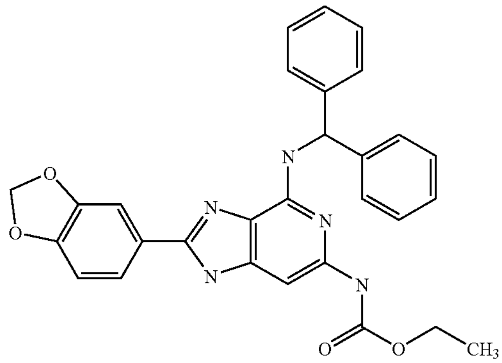 | 95 | 1.56 | >200 | >128.21 |
| A40 | Chiral; ClH | 95 | >6.25 | | |
| A41 | 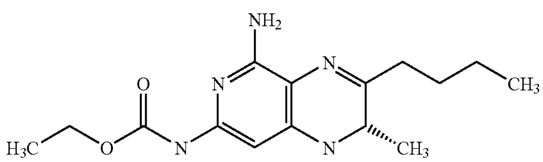 | 95 | 12.5 | 1.51 | 0.12 |
| A42 | 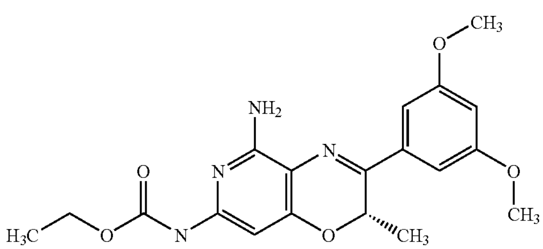 | 95 | 12.5 | | |
| A43 | 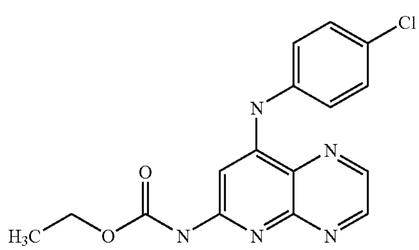 | 94 | 6.25 | | |
| A44 | 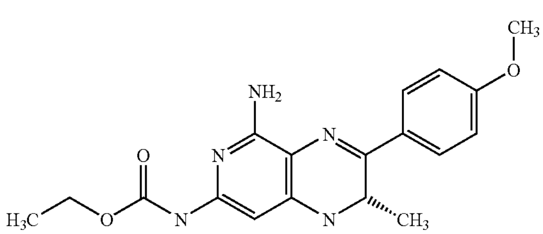 | 94 | 12.5 | 1.53 | 0.12 |

TABLE 8-continued

| Compound # | Structure | % Inh | MIC (μg/mL) | IC50 (μg/mL) | SI |
|---|---|---|---|---|---|
| A45 | 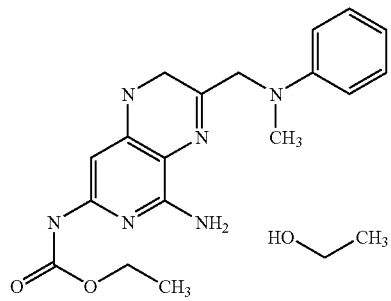 | 93 | | | |
| A46 | 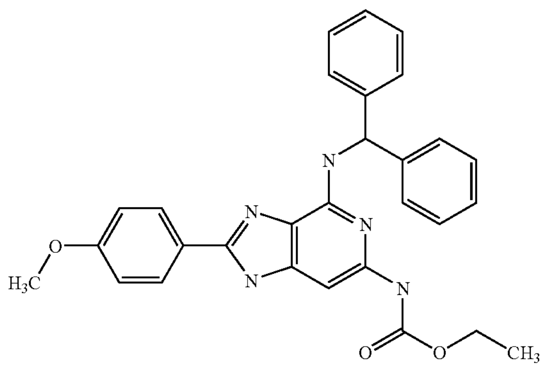 | 93 | 3.13 | 189.26 | 60.47 |
| A47 | 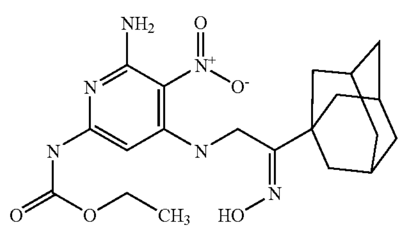 | 93 | >12.5 | | |
| A48 | 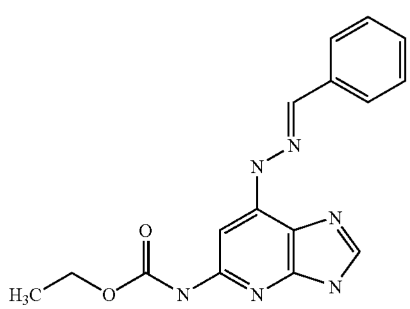 | 92 | | | |
| A49 | 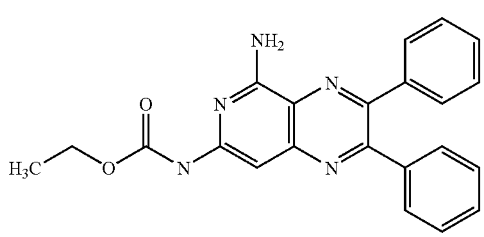 | 92 | | | |

TABLE 8-continued

| Compound # | Structure | % Inh | MIC (μg/mL) | IC50 (μg/mL) | SI |
| --- | --- | --- | --- | --- | --- |
| A50 | 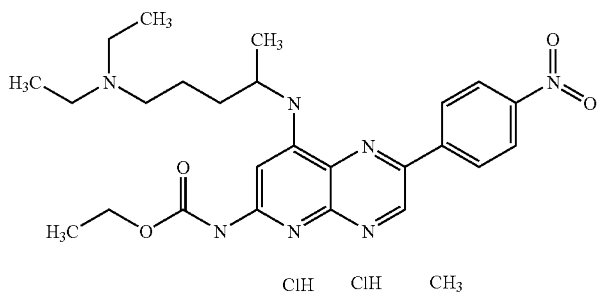 | 92 | >6.25 | | |
| A51 | 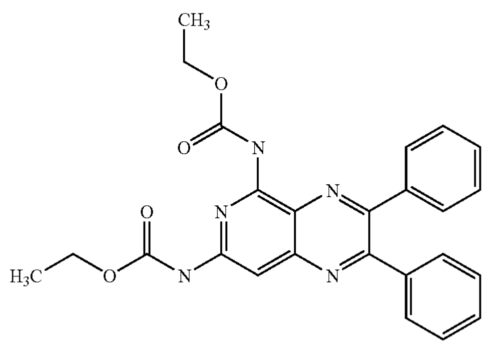 | 92 | >6.25 | | |
| A52 | 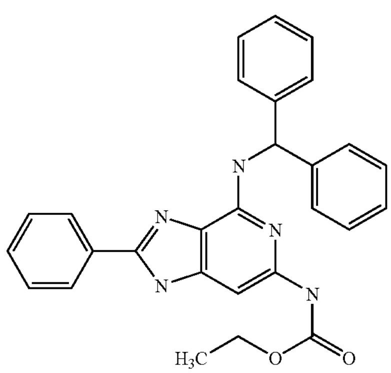 | 92 | 12.5 | >200 | >16 |
| A53 | 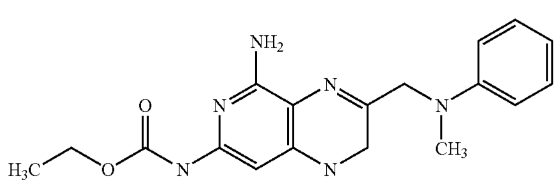 | 92 | 12.5 | 0.41 | <0.03 |
| A54 | 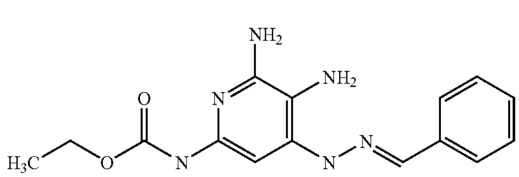 | 91 | | | |

TABLE 8-continued

| Compound # | Structure | % Inh | MIC (μg/mL) | IC50 (μg/mL) | SI |
|---|---|---|---|---|---|
| A55 | 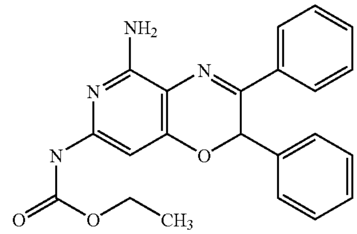 | 90 | 6.25 | | |
| A56 | 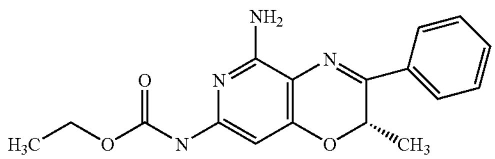 | 90 | 12.5 | | |
| A57 | 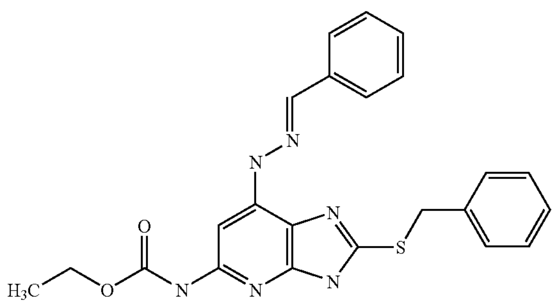 | 89 | | | |
| A58 | 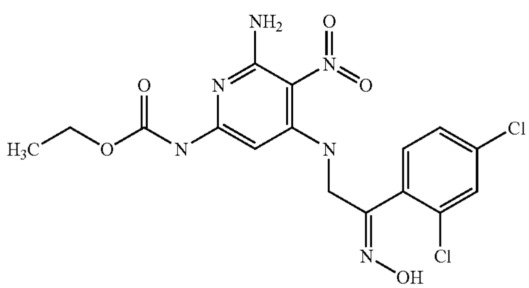 | 89 | | | |
| A59 | 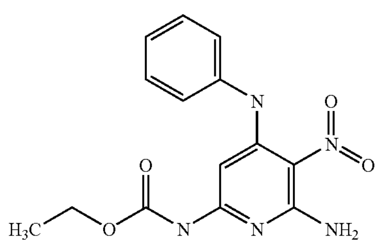 | 88 | | | |
| A60 | 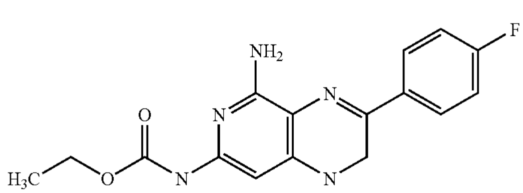 | 87 | | | |

TABLE 8-continued

| Compound # | Structure | % Inh | MIC (µg/mL) | IC50 (µg/mL) | SI |
|---|---|---|---|---|---|
| A61 | 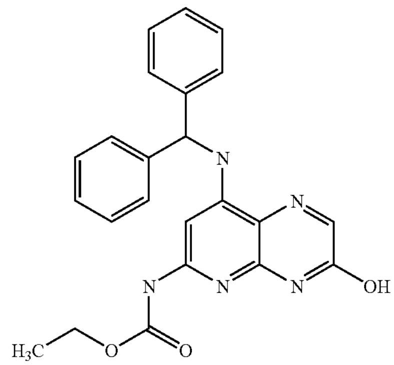 | 87 | | | |
| A62 | 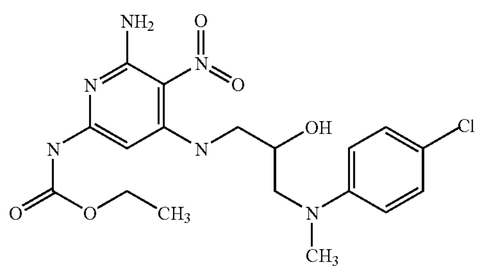 | 86 | | | |
| A63 | 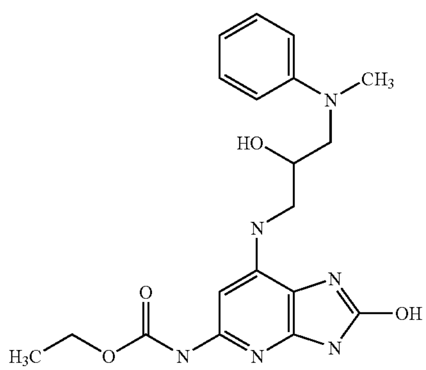 | 86 | | | |
| A64 | 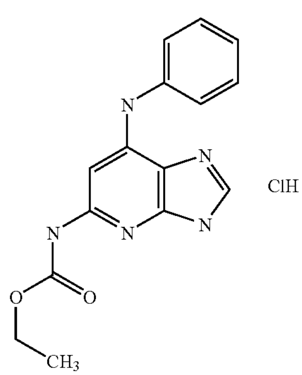 | 84 | | | |

TABLE 8-continued

| Compound # | Structure | % Inh | MIC (μg/mL) | IC50 (μg/mL) | SI |
|---|---|---|---|---|---|
| A65 | 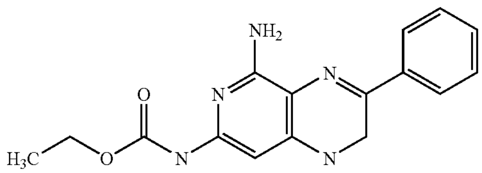 | 83 | | | |
| A66 | 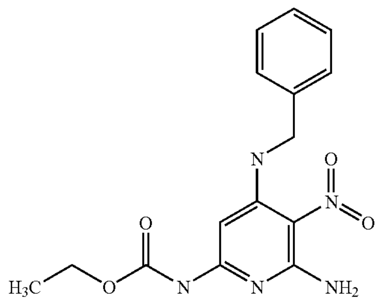 | 83 | | | |
| A67 | 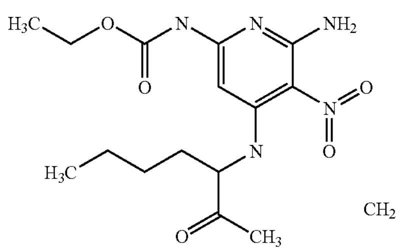 | 81 | | | |
| A68 | 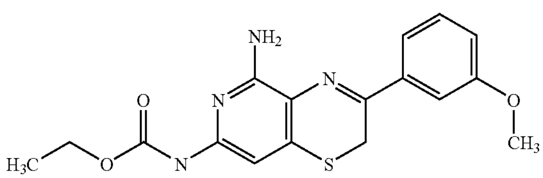 | 79 | | | |
| A69 | 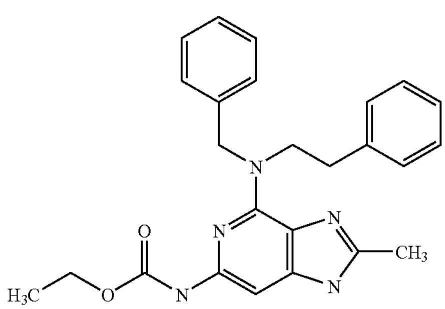 | 71 | | | |

TABLE 8-continued

| Compound # | Structure | % Inh | MIC (μg/mL) | IC50 (μg/mL) | SI |
|---|---|---|---|---|---|
| A70 | 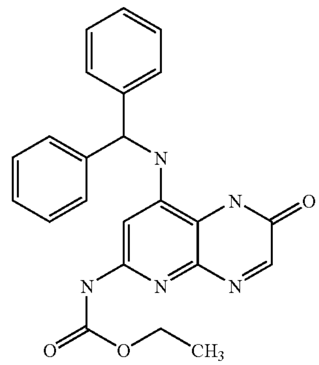 | 76 | | | |
| A71 | 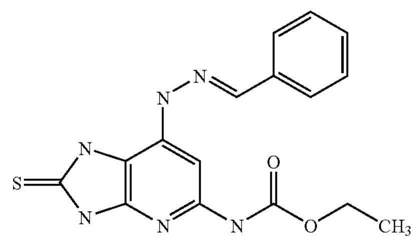 | 75 | | | |
| A72 | 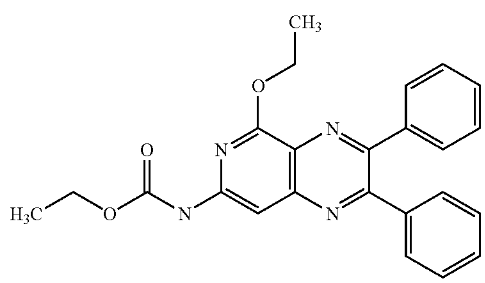 | 75 | | | |
| A73 | 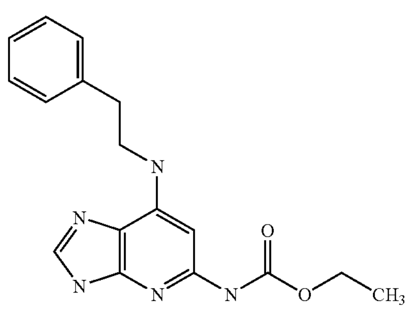 | 74 | | | |
| A74 | 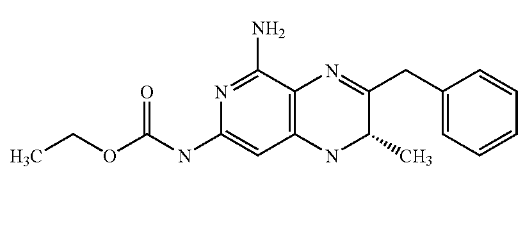 | 72 | | | |

TABLE 8-continued

| Compound # | Structure | % Inh | MIC (μg/mL) | IC50 (μg/mL) | SI |
|---|---|---|---|---|---|
| A75 | 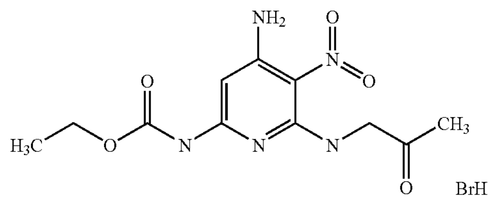 | 72 | | | |
| A76 | 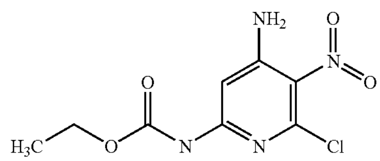 | 72 | | | |
| A77 | 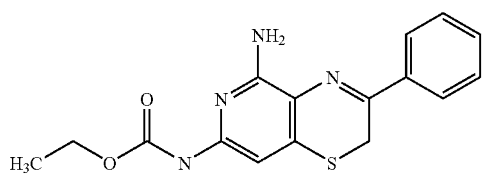 | 71 | | | |
| A78 | 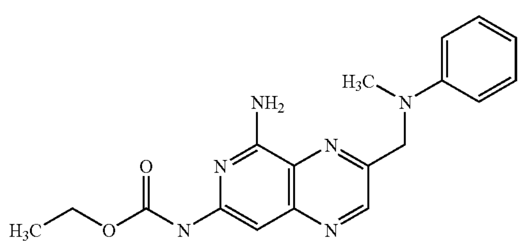 | 71 | | | |
| A79 | 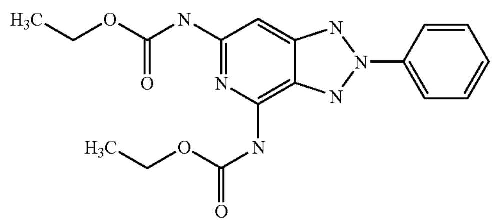 | 71 | | | |
| A80 | 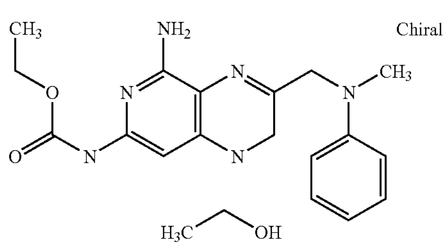 | 70 | | | |

TABLE 8-continued

| Compound # | Structure | % Inh | MIC (µg/mL) | IC50 (µg/mL) | SI |
|---|---|---|---|---|---|
| A81 | 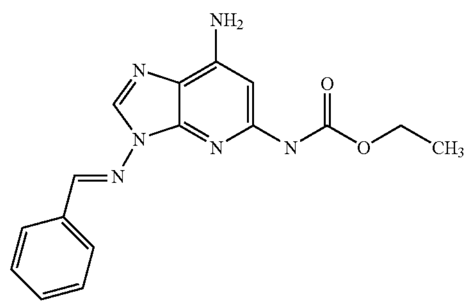 | 69 | | | |
| A82 | 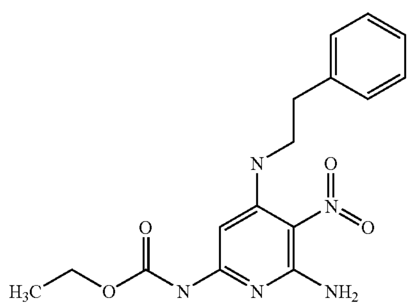 | 68 | | | |
| A83 | 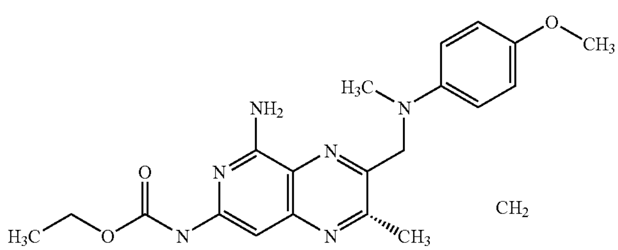 | 66 | | | |
| A84 | 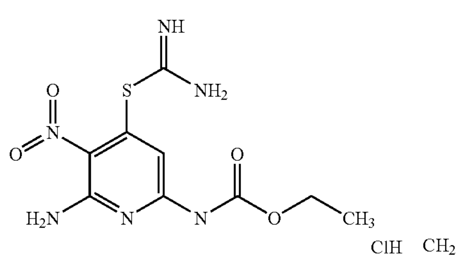 | 66 | | | |
| A85 | 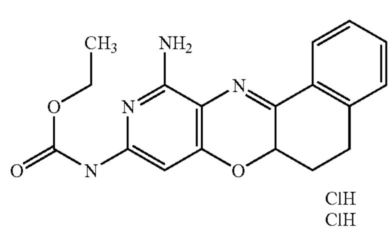 | 65 | | | |

TABLE 8-continued

| Compound # | Structure | % Inh | MIC (µg/mL) | IC50 (µg/mL) | SI |
|---|---|---|---|---|---|
| A86 | 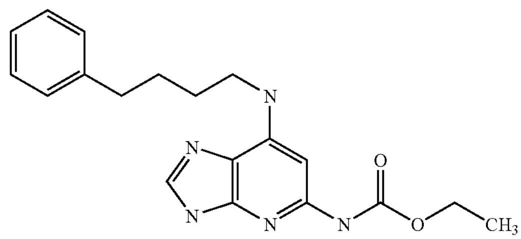 | 65 | | | |
| A87 | 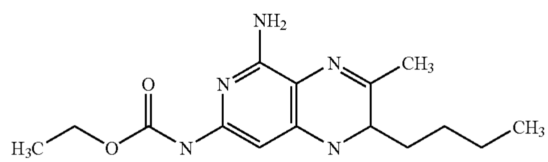 | 64 | | | |
| A88 | 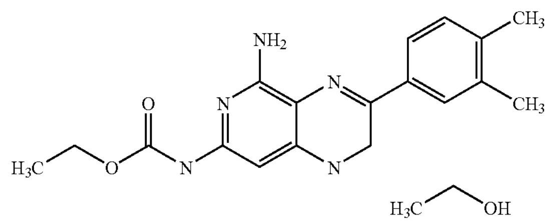 | 64 | | | |
| A89 | 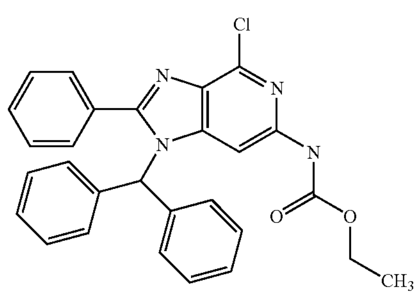 | 63 | | | |
| A90 | 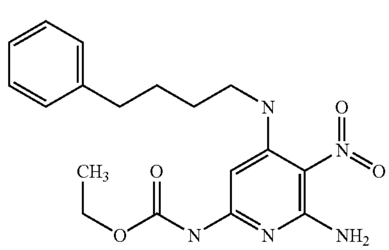 | 62 | | | |
| A91 | 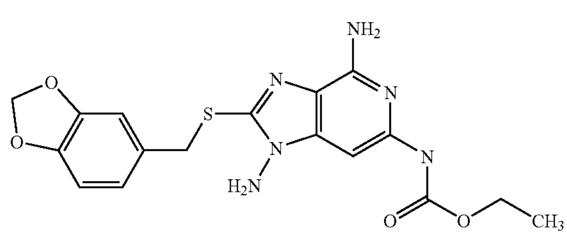 | 61 | | | |

TABLE 8-continued

| Compound # | Structure | % Inh | MIC (μg/mL) | IC50 (μg/mL) | SI |
|---|---|---|---|---|---|
| A92 | 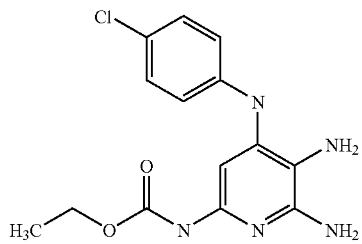 | 61 | | | |
| A93 | 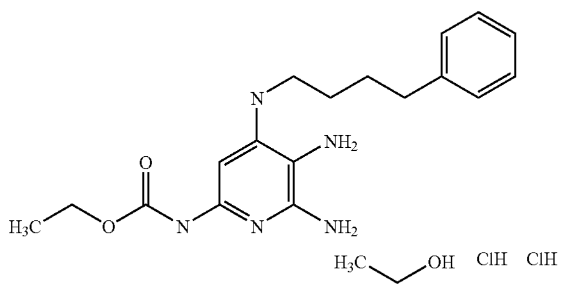 | 60 | | | |
| A94 | 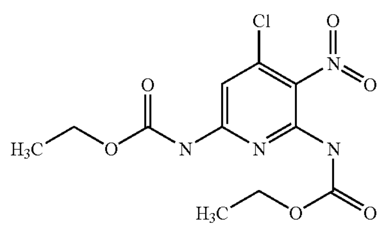 | 59 | | | |
| A95 | 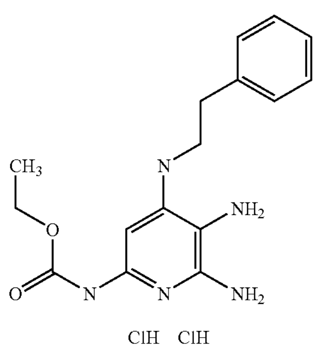 | 59 | | | |
| A96 | 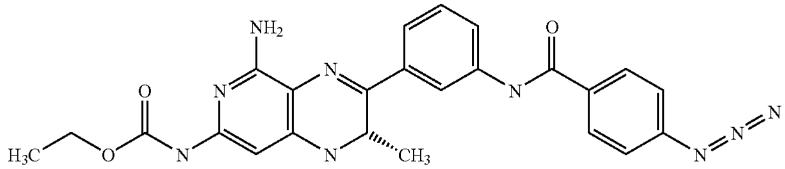 | 58 | | | |
| A97 | 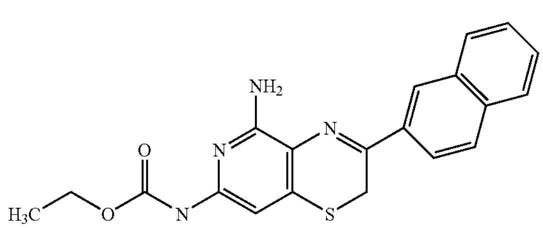 | 58 | | | |

TABLE 8-continued

| Compound # | Structure | % Inh | MIC (μg/mL) | IC50 (μg/mL) | SI |
|---|---|---|---|---|---|
| A98 | 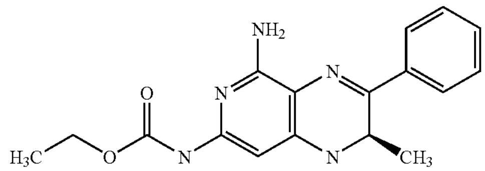 | 57 | | | |
| A99 | (Chiral) | 56 | | | |
| A100 | | 55 | | | |
| A101 | 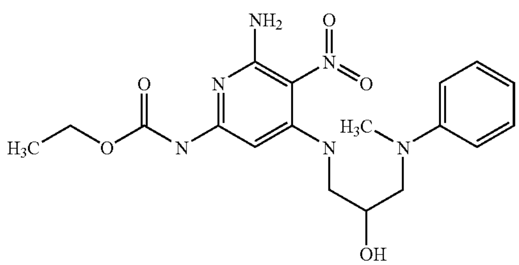 | 54 | | | |
| A102 | 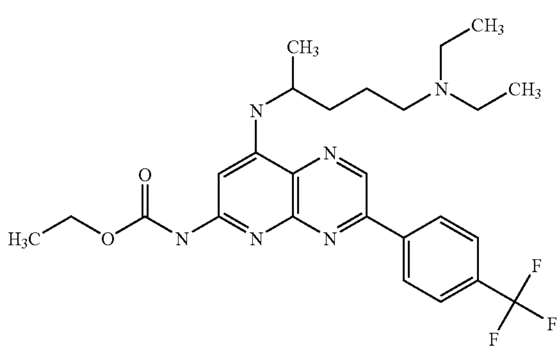 | 54 | | | |
| A103 | 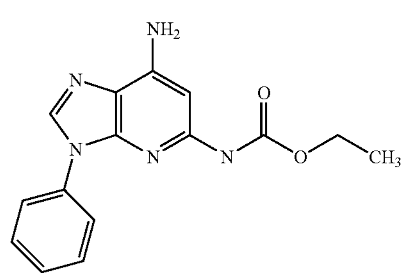 | 53 | | | |

TABLE 8-continued

| Compound # | Structure | % Inh | MIC (μg/mL) | IC50 (μg/mL) | SI |
|---|---|---|---|---|---|
| A104 | 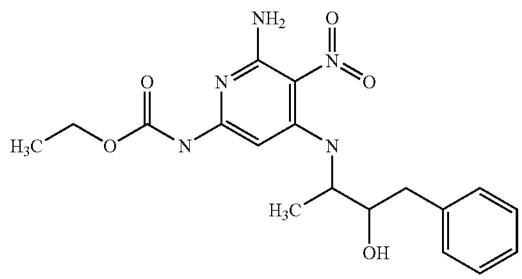 | 51 | | | |
| A105 | 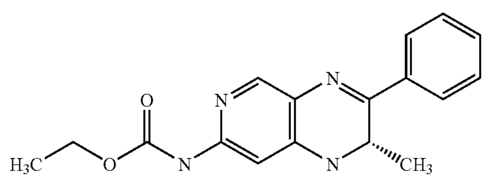 | 49 | | | |
| A106 | 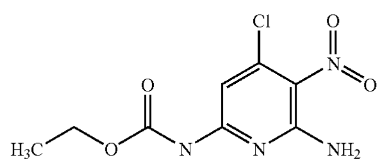 | 49 | | | |
| A107 | 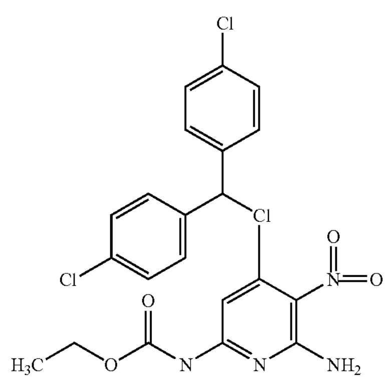 | 46 | | | |
| A108 | 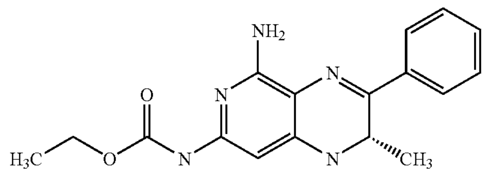 | 45 | | | |
| A109 | | 45 | | | |
| A110 | 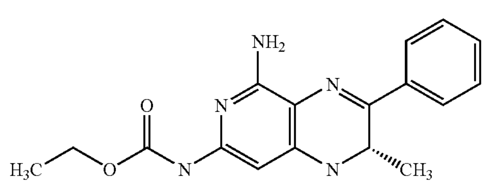 | 43 | | | |

TABLE 8-continued

| Compound # | Structure | % Inh | MIC (µg/mL) | IC50 (µg/mL) | SI |
|---|---|---|---|---|---|
| A111 | 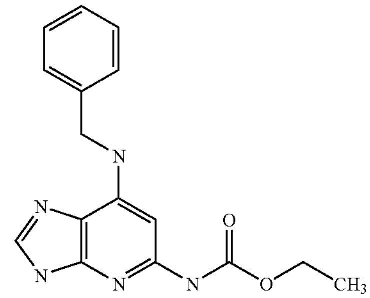 | 43 | | | |
| A112 | 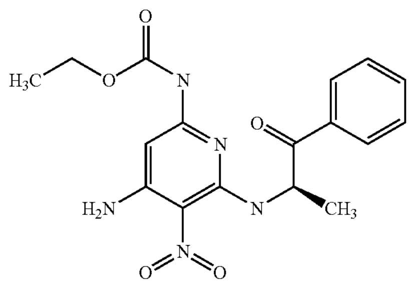 | 42 | | | |
| A113 | 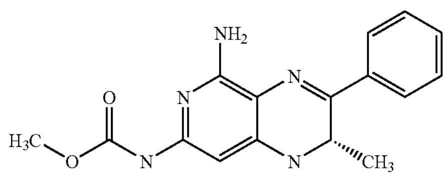 | 41 | | | |
| A114 | 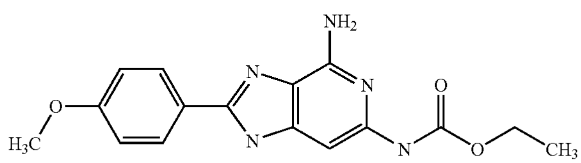 | 41 | | | |
| A115 | 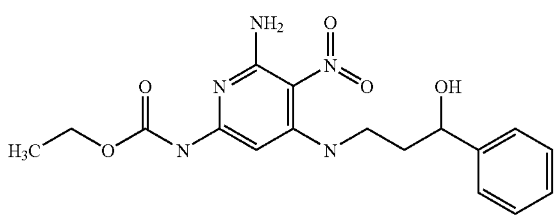 | 41 | | | |
| A116 | | 41 | | | |
| A117 | 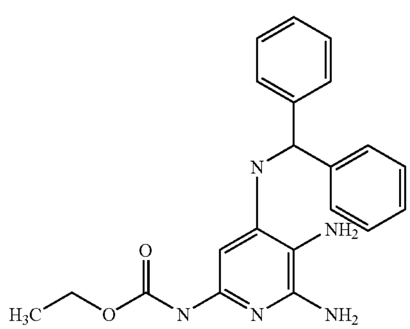 | 40 | | | |

TABLE 8-continued

| Compound # | Structure | % Inh | MIC (μg/mL) | IC50 (μg/mL) | SI |
|---|---|---|---|---|---|
| A118 | 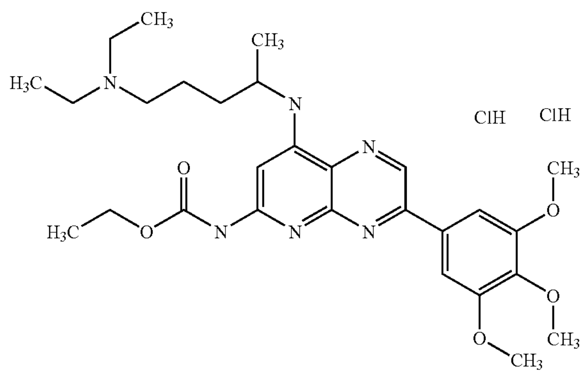 | 40 | | | |
| A119 | 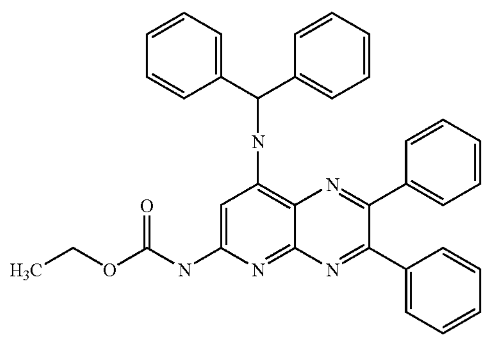 | 36 | | | |
| A120 | 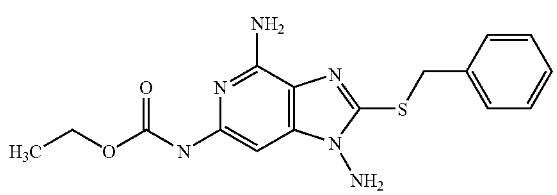 | 34 | | | |
| A121 | 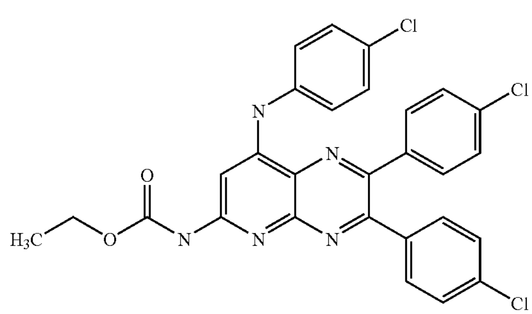 | 33 | | | |
| A122 | 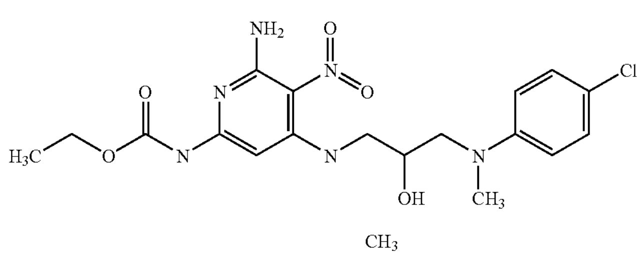 | 31 | | | |

TABLE 8-continued

| Compound # | Structure | % Inh | MIC (μg/mL) | IC50 (μg/mL) | SI |
|---|---|---|---|---|---|
| A123 | 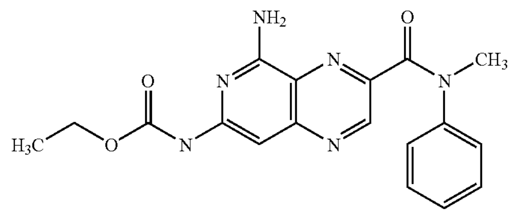 | 31 | | | |
| A124 | 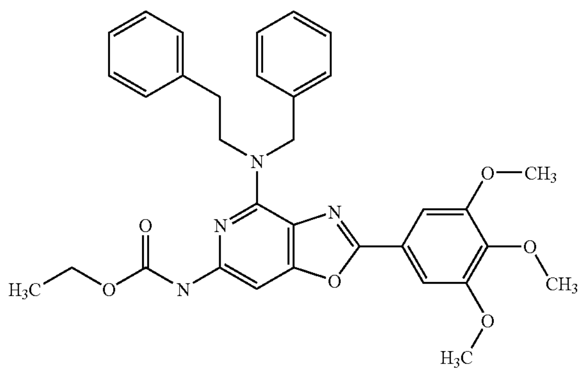 | 31 | | | |
| A125 | 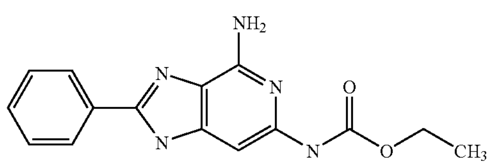 | 30 | | | |
| A126 | 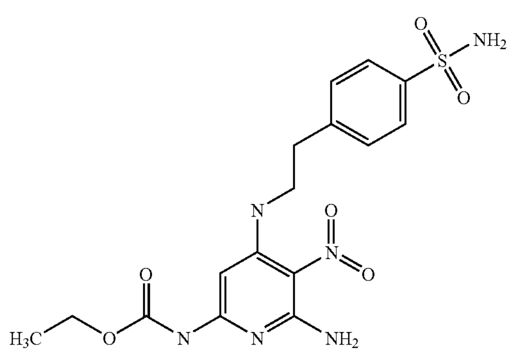 | 30 | | | |
| A127 | 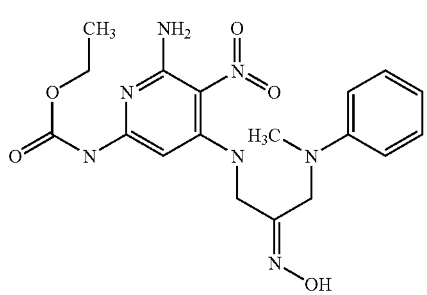 | 30 | | | |

TABLE 8-continued

| Compound # | Structure | % Inh | MIC (µg/mL) | IC50 (µg/mL) | SI |
|---|---|---|---|---|---|
| A128 | 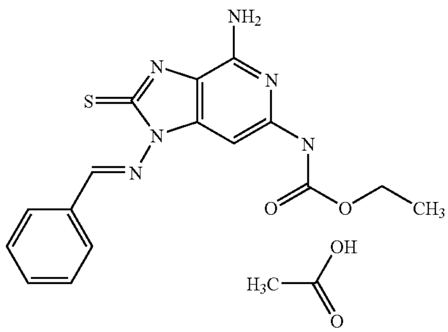 | 29 | | | |
| A129 | 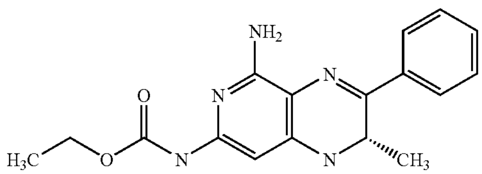 | 28 | | | |
| A130 | 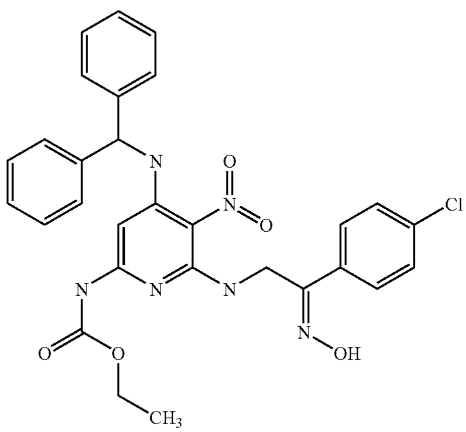 | 28 | | | |
| A131 | 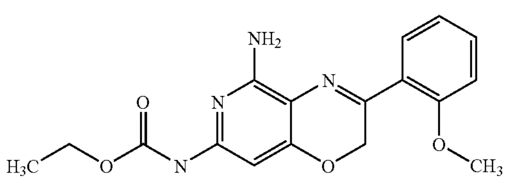 | 25 | | | |
| A132 | 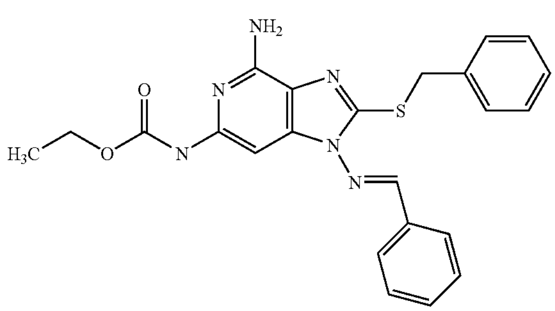 | 24 | | | |

TABLE 8-continued

| Compound # | Structure | % Inh | MIC (μg/mL) | IC50 (μg/mL) | SI |
|---|---|---|---|---|---|
| A133 | 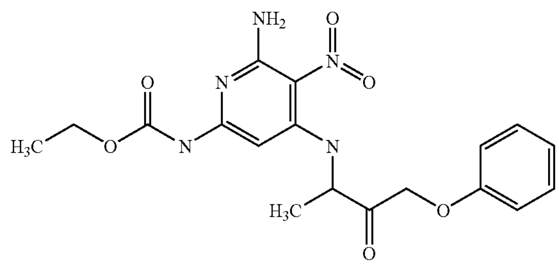 | 23 | | | |
| A134 | 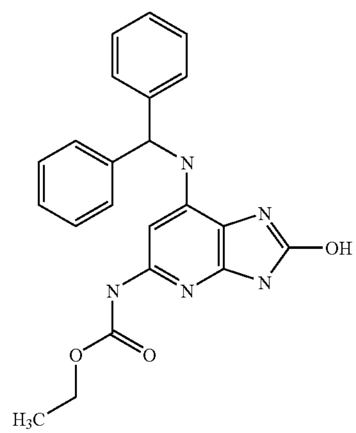 | 23 | | | |
| A135 | 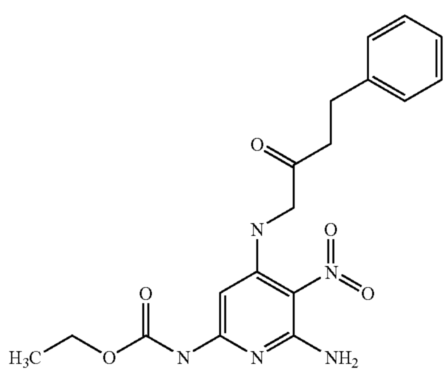 | 22 | | | |
| A136 | 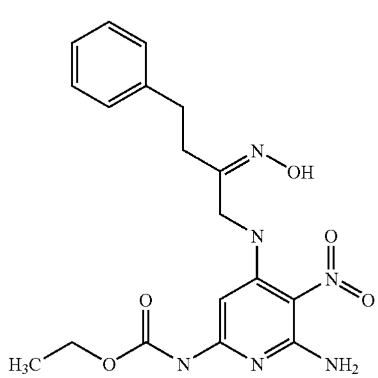 | 21 | | | |

TABLE 8-continued

| Compound # | Structure | % Inh | MIC (μg/mL) | IC50 (μg/mL) | SI |
|---|---|---|---|---|---|
| A137 | 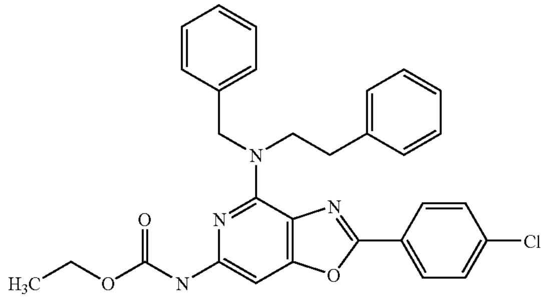 | 21 | | | |
| A138 | 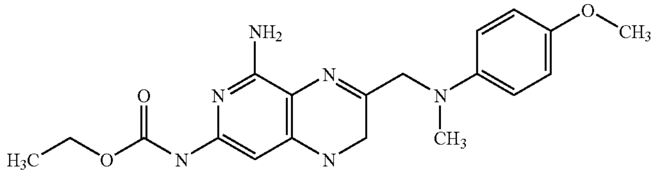 | 20 | | | |
| A139 | 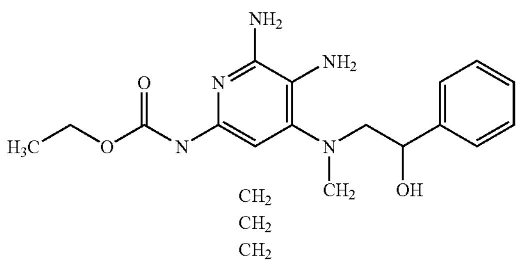 | 20 | | | |
| A140 | 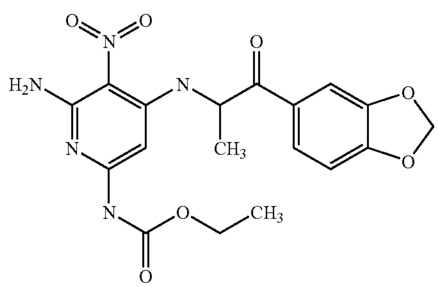 | 19 | | | |
| A141 | 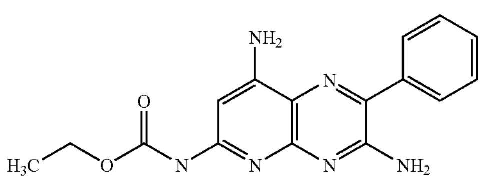 | 19 | | | |
| A142 | 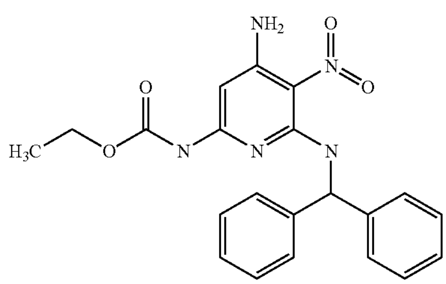 | 18 | | | |

TABLE 8-continued

| Compound # | Structure | % Inh | MIC (μg/mL) | IC50 (μg/mL) | SI |
|---|---|---|---|---|---|
| A143 | 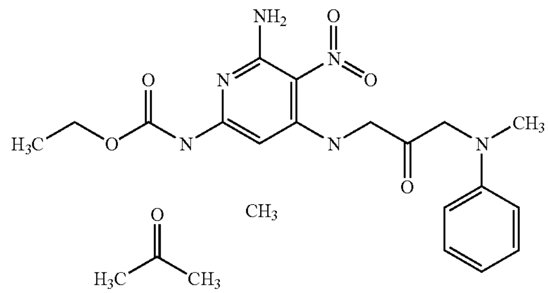 | 17 | | | |
| A144 | 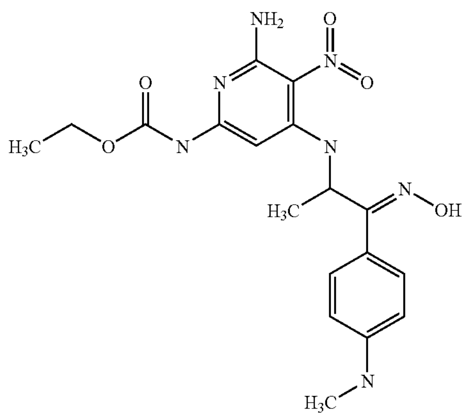 | 16 | | | |
| A145 | 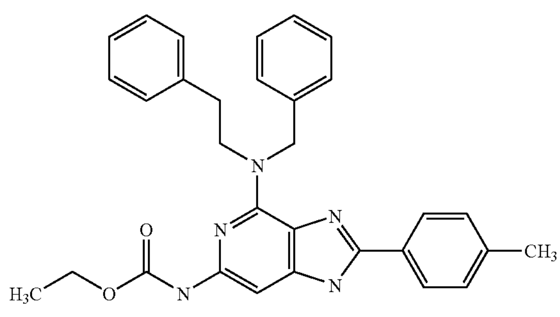 | 16 | | | |
| A146 | | 15 | | | |
| A147 | 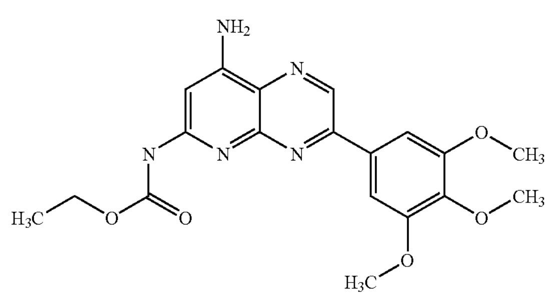 | 15 | | | |
| A148 | 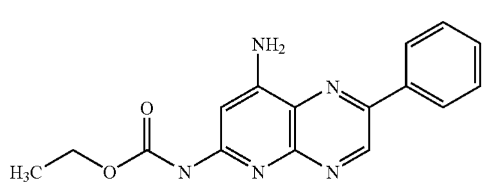 | 14 | | | |

TABLE 8-continued

| Compound # | Structure | % Inh | MIC (μg/mL) | IC50 (μg/mL) | SI |
|---|---|---|---|---|---|
| A149 | 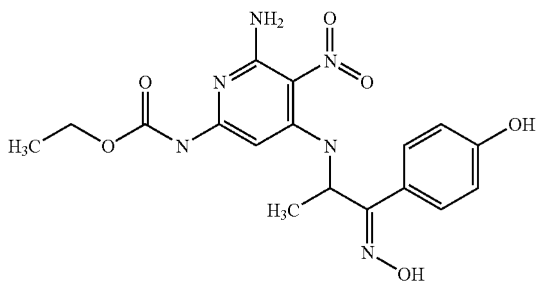 | 14 | | | |
| A150 | 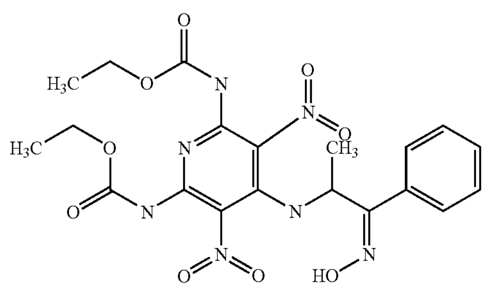 | 14 | | | |
| A151 | 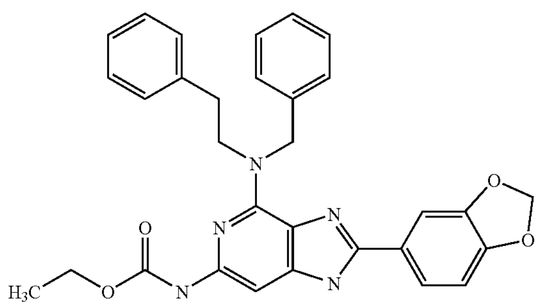 | 14 | | | |
| A152 | 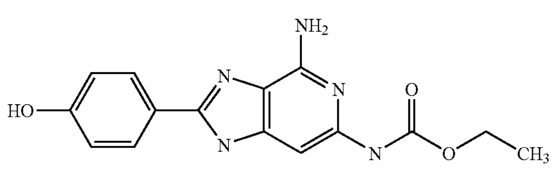 | 13 | | | |
| A153 | 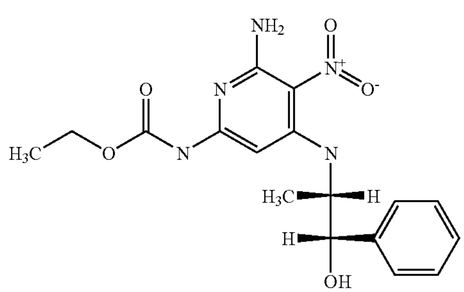 | 12 | | | |

TABLE 8-continued

| Compound # | Structure | % Inh | MIC (µg/mL) | IC50 (µg/mL) | SI |
|---|---|---|---|---|---|
| A154 | 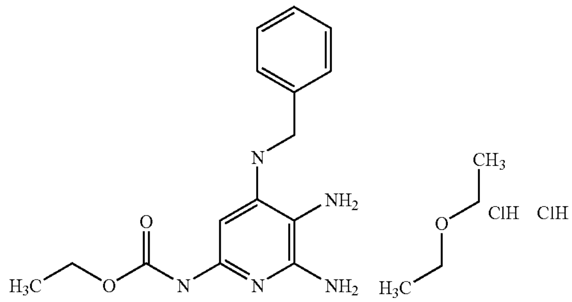 | 12 | | | |
| A155 | 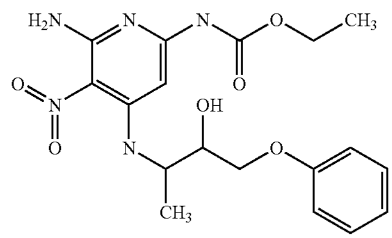 | 11 | | | |
| A156 | 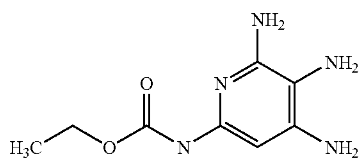 | 10 | | | |
| A157 | Chiral | 10 | | | |
| A158 | 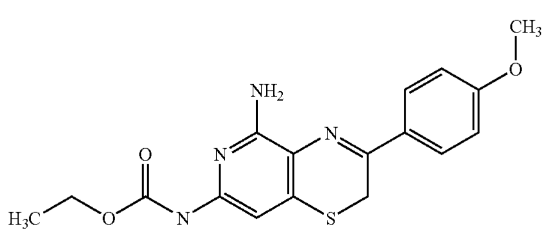 | 10 | | | |
| A159 | 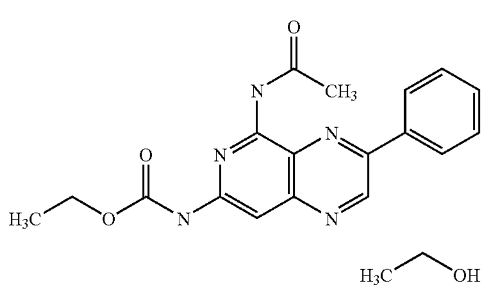 | 10 | | | |

TABLE 8-continued

| Compound # | Structure | % Inh | MIC (µg/mL) | IC50 (µg/mL) | SI |
|---|---|---|---|---|---|
| A160 | (chiral structure) | 10 | | | |
| A161 | (structure) | 9 | | | |
| A162 | (structure) | 8 | | | |
| A163 | (structure) | 8 | | | |
| A164 | (chiral structure) | 8 | | | |
| A165 | (structure) | 8 | | | |

TABLE 8-continued

| Compound # | Structure | % Inh | MIC (μg/mL) | IC50 (μg/mL) | SI |
|---|---|---|---|---|---|
| A166 | 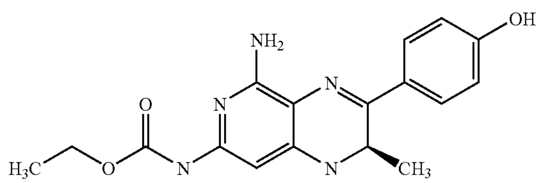 | 8 | | | |
| A167 | 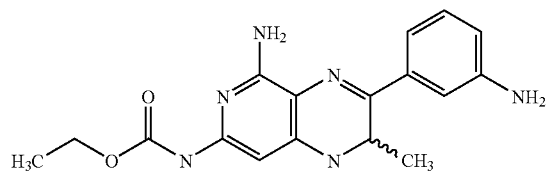 | 7 | | | |
| A168 | | 7 | | | |
| A169 | 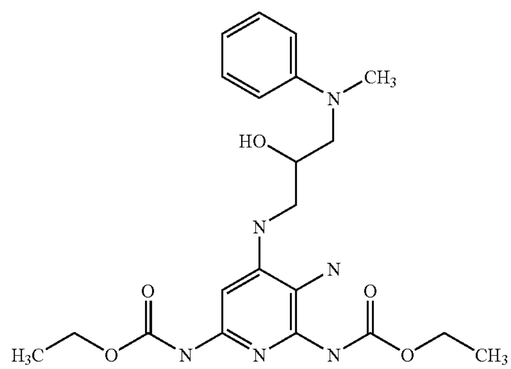 | 7 | | | |
| A170 | 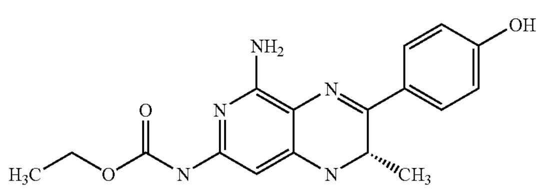 | 7 | | | |
| A171 | 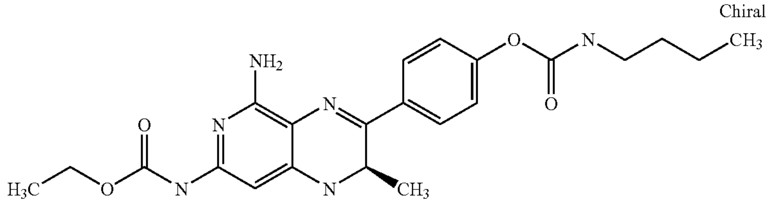 | 7 | | | |

TABLE 8-continued

| Compound # | Structure | % Inh | MIC (µg/mL) | IC50 (µg/mL) | SI |
|---|---|---|---|---|---|
| A172 | 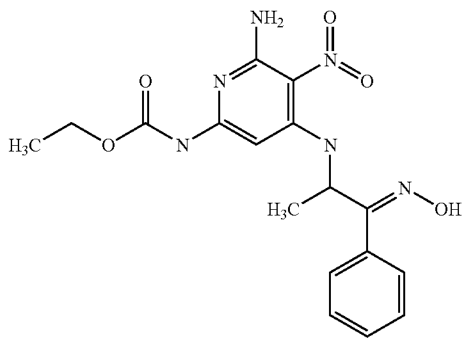 | 5 | | | |
| A173 | 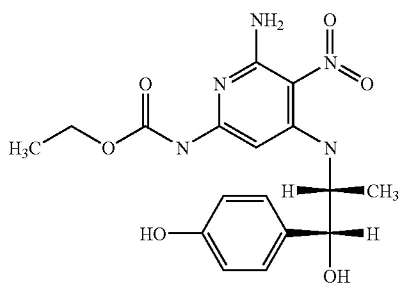 | 5 | | | |
| A174 | 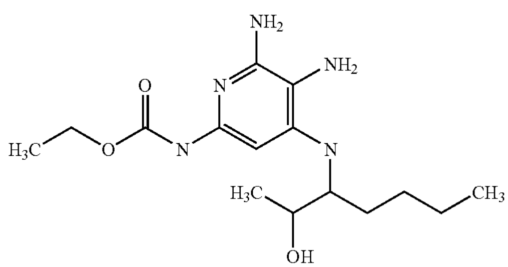 | 5 | | | |
| A175 | 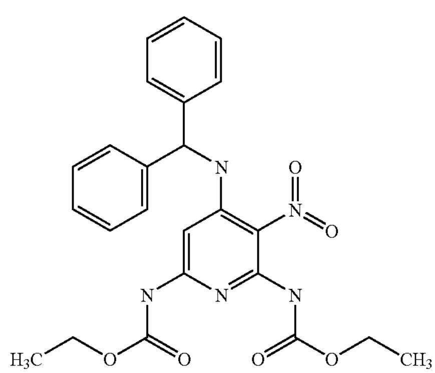 | 5 | | | |

TABLE 8-continued

| Compound # | Structure | % Inh | MIC (μg/mL) | IC50 (μg/mL) | SI |
|---|---|---|---|---|---|
| A176 | 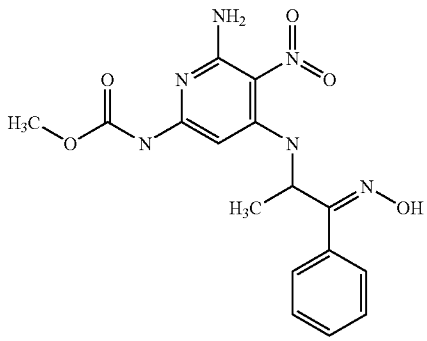 | 4 | | | |
| A177 | 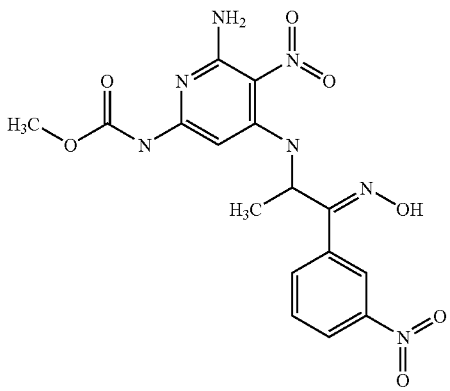 | 4 | | | |
| A178 | 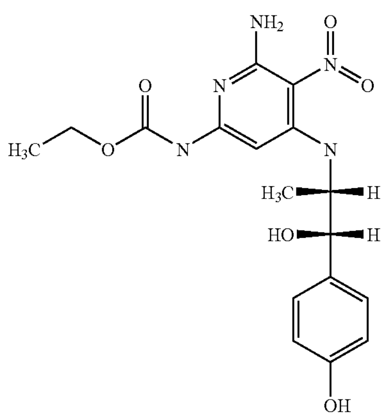 | 4 | | | |
| A179 | 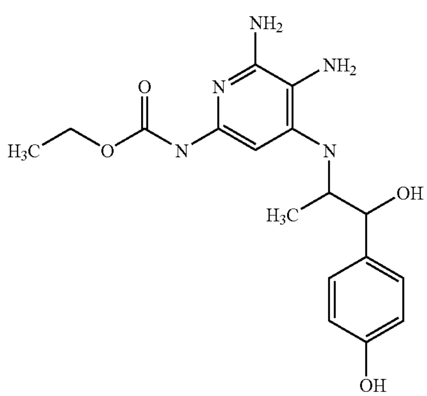 | 4 | | | |

TABLE 8-continued

| Compound # | Structure | % Inh | MIC (μg/mL) | IC50 (μg/mL) | SI |
|---|---|---|---|---|---|
| A180 | 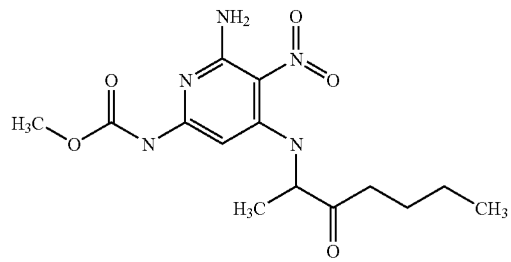 | 3 | | | |
| A181 | 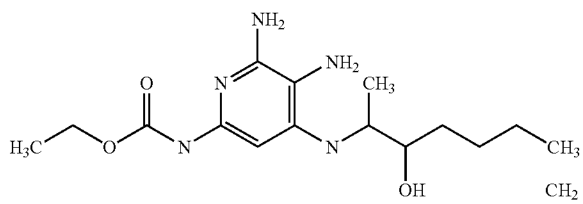 | 3 | | | |
| A182 | 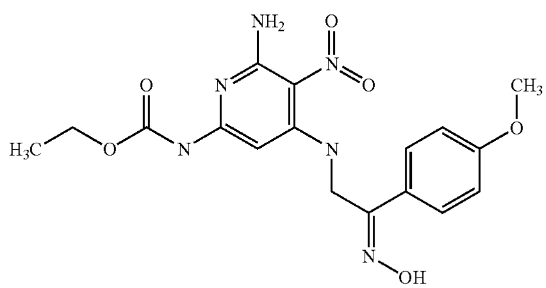 | 2 | | | |
| A183 | 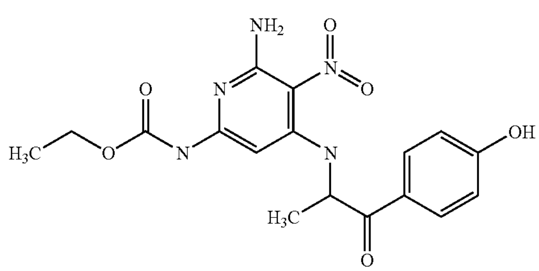 | 2 | | | |
| A184 | | 2 | | | |
| A185 | 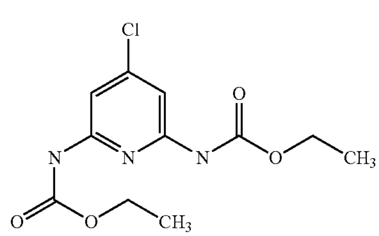 | 2 | | | |

TABLE 8-continued

| Compound # | Structure | % Inh | MIC (µg/mL) | IC50 (µg/mL) | SI |
|---|---|---|---|---|---|
| A186 | 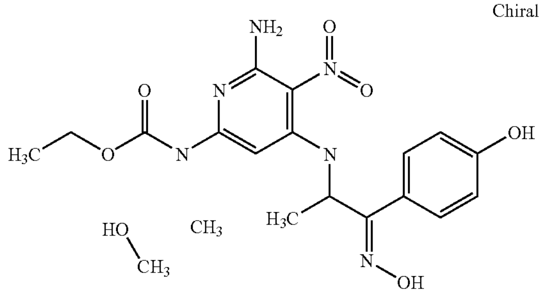 | 1 | | | |
| A187 | 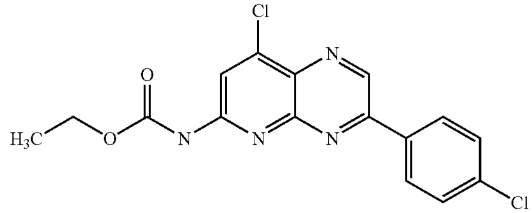 | 1 | | | |
| A188 | 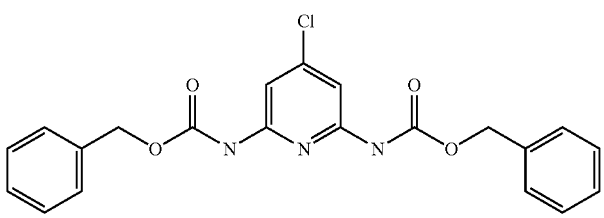 | 1 | | | |
| A189 | | 0 | | | |
| A190 | 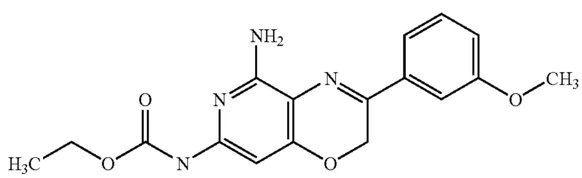 | 0 | | | |
| A191 | 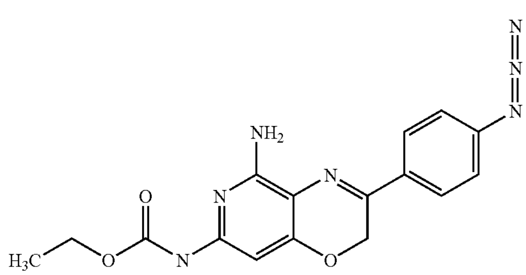 | 0 | | | |
| A192 | 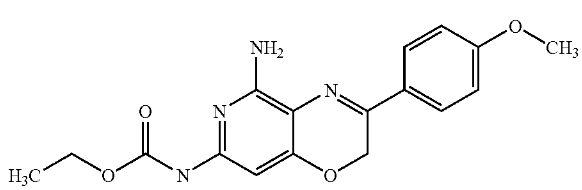 | 0 | | | |

TABLE 8-continued

| Compound # | Structure | % Inh | MIC (µg/mL) | IC50 (µg/mL) | SI |
|---|---|---|---|---|---|
| A193 | 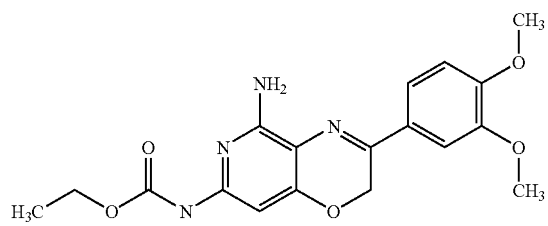 | 0 | | | |
| A194 | 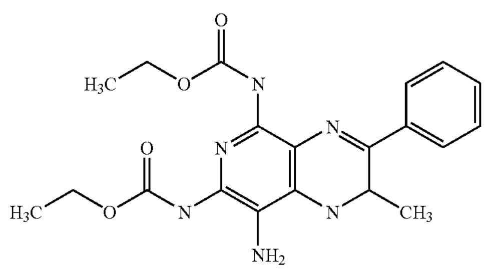 | 0 | | | |
| A195 | 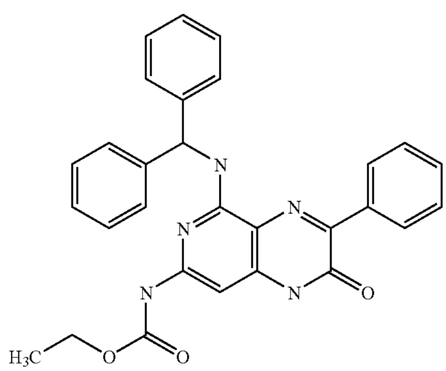 | 0 | | | |
| A196 | 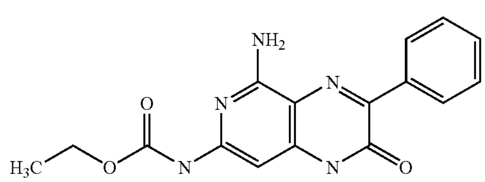 | 0 | | | |
| A197 | 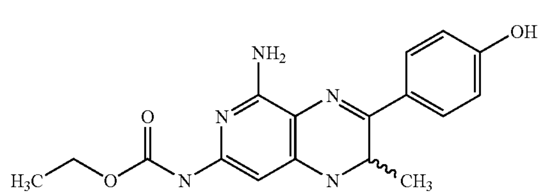 | 0 | | | |

TABLE 8-continued

| Compound # | Structure | % Inh | MIC (μg/mL) | IC50 (μg/mL) | SI |
|---|---|---|---|---|---|
| A198 | 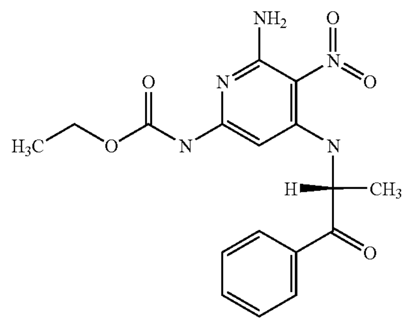 | 0 | | | |
| A199 | 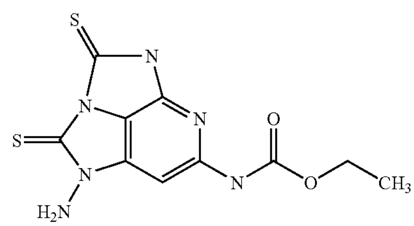 | 0 | | | |
| A200 | 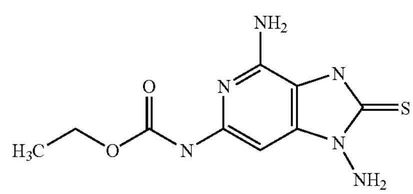 | 0 | | | |
| A201 | 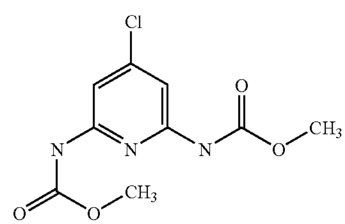 | 0 | | | |
| A202 | 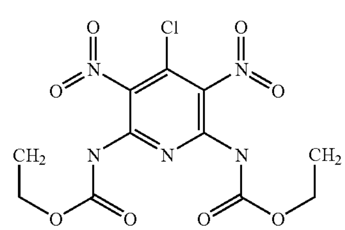 | 0 | | | |
| A203 | 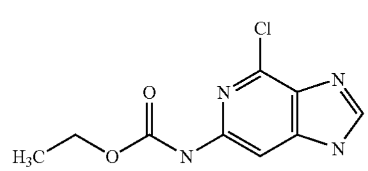 | 0 | | | |

TABLE 8-continued

| Compound # | Structure | % Inh | MIC (μg/mL) | IC50 (μg/mL) | SI |
|---|---|---|---|---|---|
| A204 | 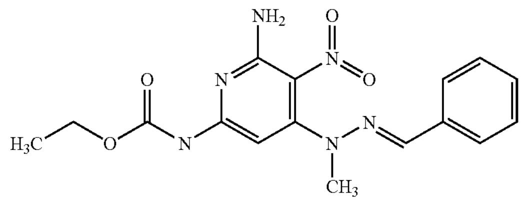 | 0 | | | |
| A205 | 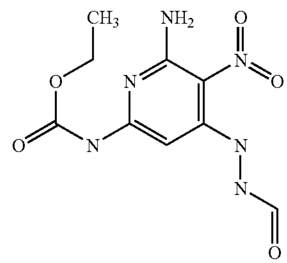 | 0 | | | |
| A206 | 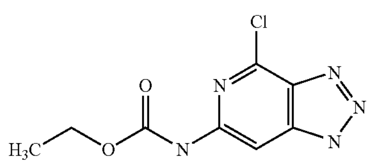 | 0 | | | |
| A207 | 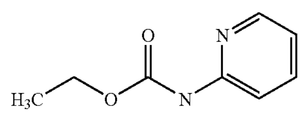 | 0 | | | |
| A208 | 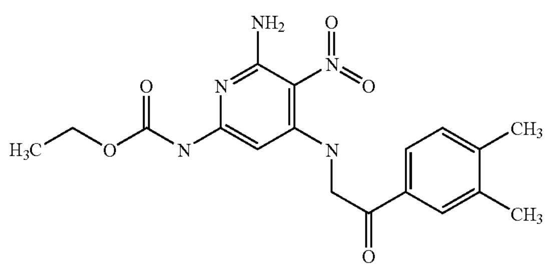 | 0 | | | |
| A209 | 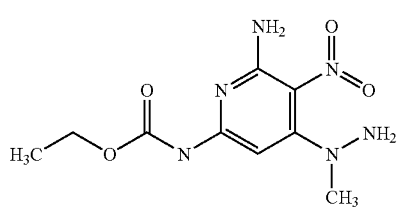 | 0 | | | |
| A210 | 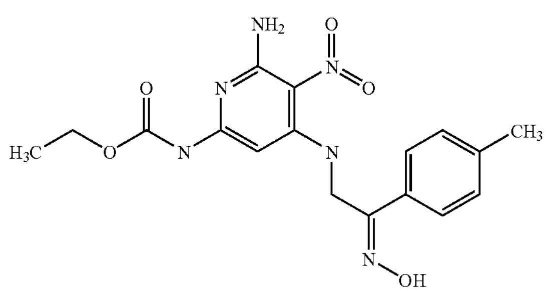 | 0 | | | |

TABLE 8-continued

| Compound # | Structure | % Inh | MIC (μg/mL) | IC50 (μg/mL) | SI |
|---|---|---|---|---|---|
| A211 | 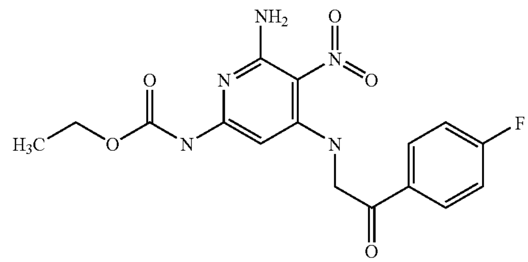 | 0 | | | |
| A212 | 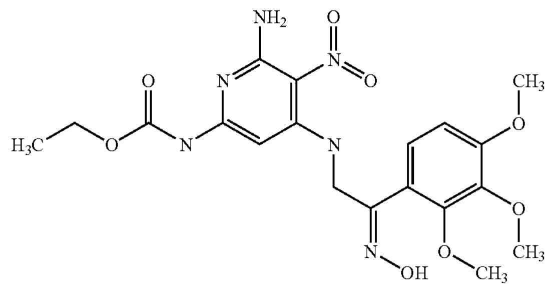 | 0 | | | |
| A213 | | 0 | | | |
| A214 | 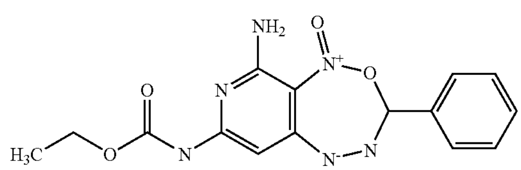 | 0 | | | |
| A215 | 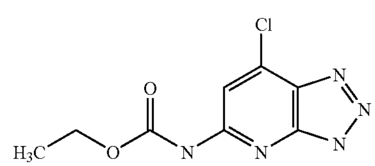 | 0 | | | |
| A216 | 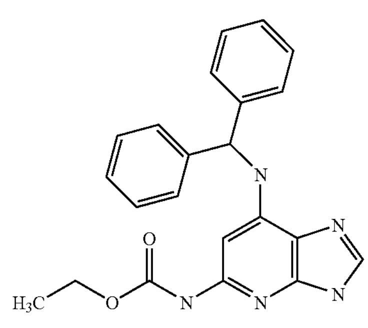 | 0 | | | |
| A217 | 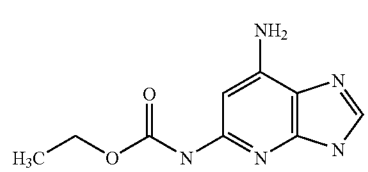 | 0 | | | |

TABLE 8-continued

| Compound # | Structure | % Inh | MIC (μg/mL) | IC50 (μg/mL) | SI |
|---|---|---|---|---|---|
| A218 | 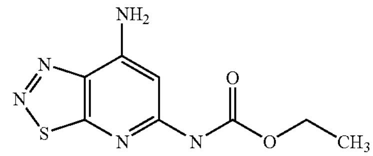 | 0 | | | |
| A219 | 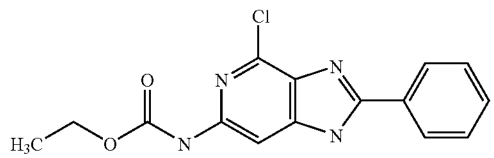 | 0 | | | |
| A220 | 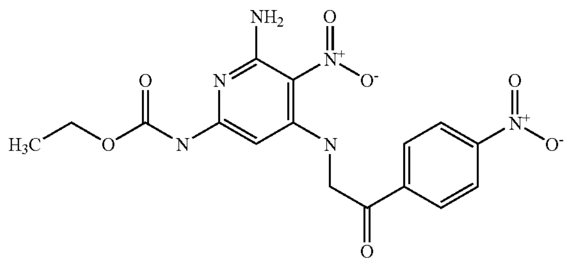 | 0 | | | |
| A221 | 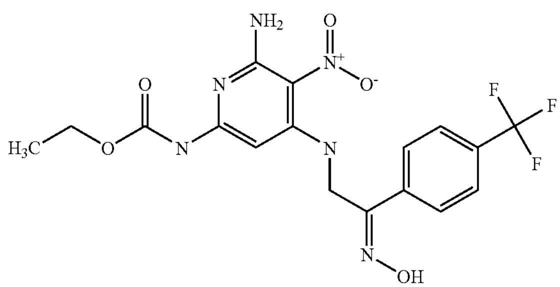 | 0 | | | |
| A222 | 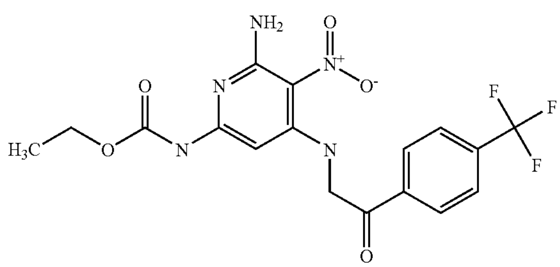 | 0 | | | |
| A223 | 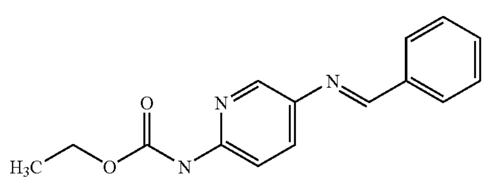 | 0 | | | |
| A224 | 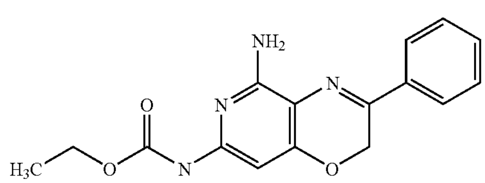 | 0 | | | |

TABLE 8-continued

| Compound # | Structure | % Inh | MIC (μg/mL) | IC50 (μg/mL) | SI |
|---|---|---|---|---|---|
| A225 | 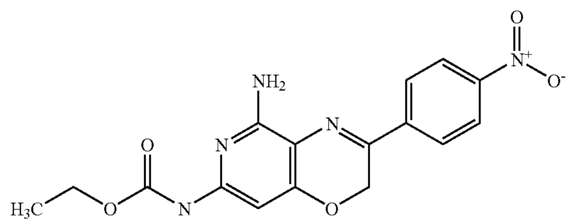 | 0 | | | |
| A226 | 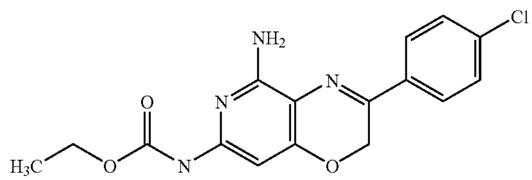 | 0 | | | |
| A227 | 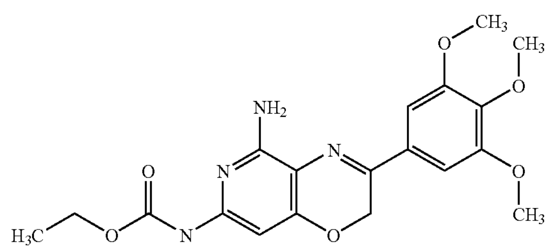 | 0 | | | |
| A228 | 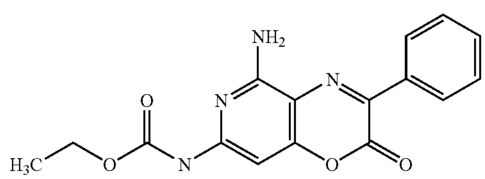 | 0 | | | |
| A229 | 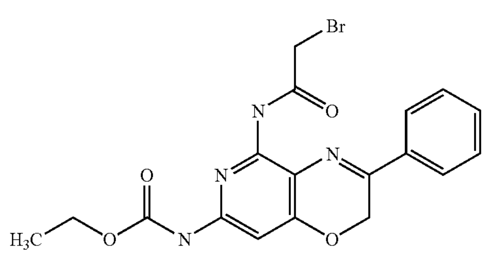 | 0 | | | |
| A230 | 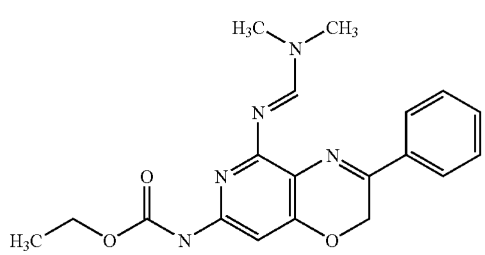 | 0 | | | |

TABLE 8-continued

| Compound # | Structure | % Inh | MIC (µg/mL) | IC50 (µg/mL) | SI |
|---|---|---|---|---|---|
| A231 | 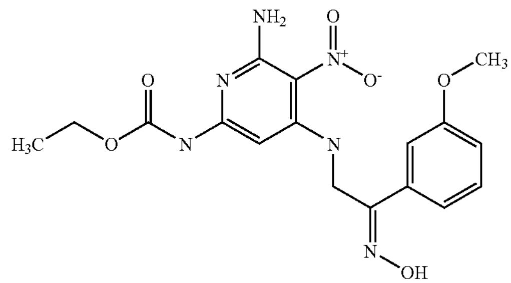 | 0 | | | |
| A232 | 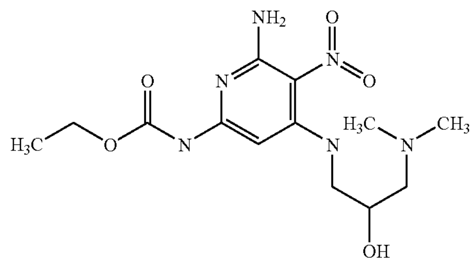 | 0 | | | |
| A233 | 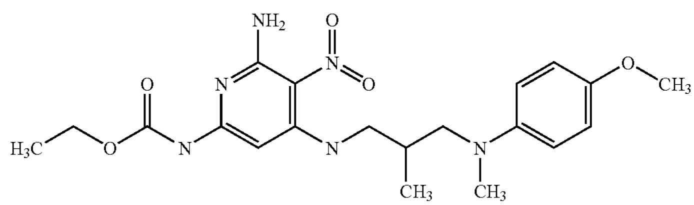 | 0 | | | |
| A234 | 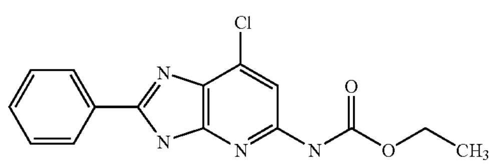 | 0 | | | |
| A235 | 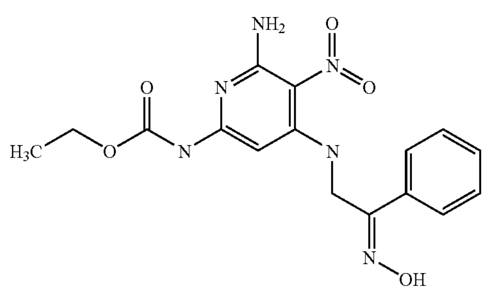 | 0 | | | |
| A236 | 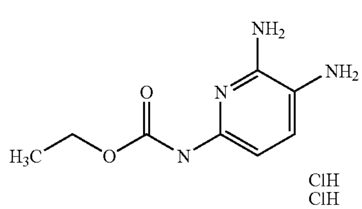 | 0 | | | |

TABLE 8-continued
| Compound # | Structure | % Inh | MIC (µg/mL) | IC50 (µg/mL) | SI |
|---|---|---|---|---|---|
| A237 | 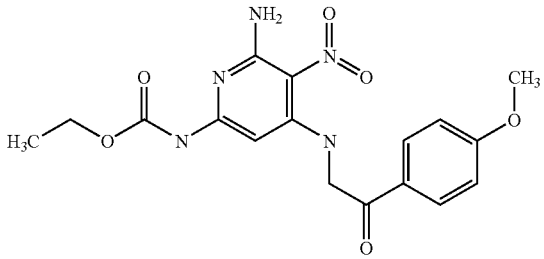 | 0 | | | |
| A238 | 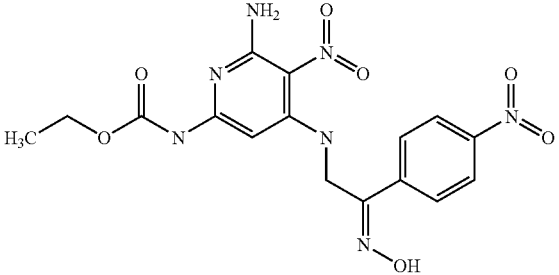 | 0 | | | |
| A239 | 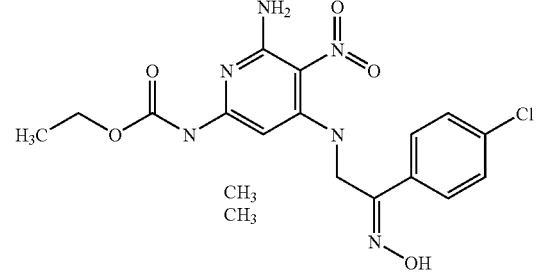 | 0 | | | |
| A240 | 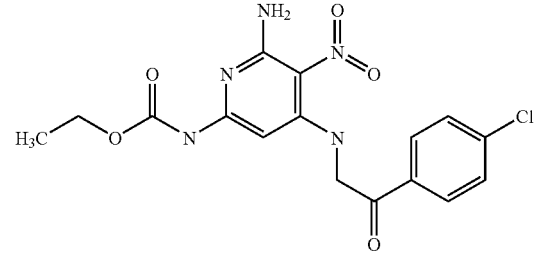 | 0 | | | |
| A241 | 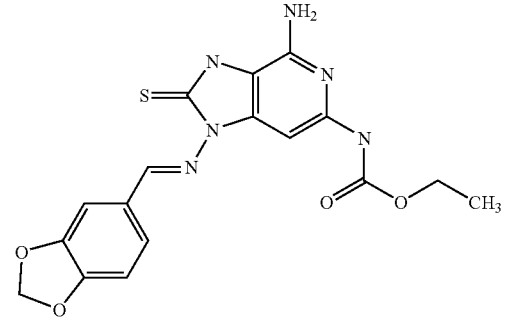 | 0 | | | |

TABLE 8-continued

| Compound # | Structure | % Inh | MIC (μg/mL) | IC50 (μg/mL) | SI |
|---|---|---|---|---|---|
| A242 | 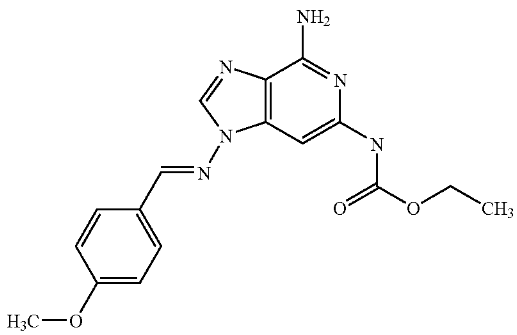 | 0 | | | |
| A243 | 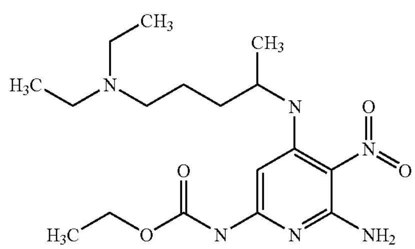 | 0 | | | |
| A244 | 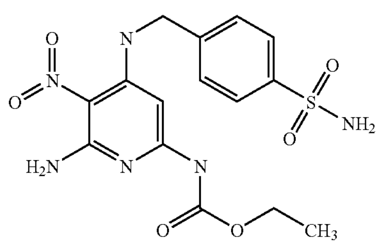 | 0 | | | |
| A245 | 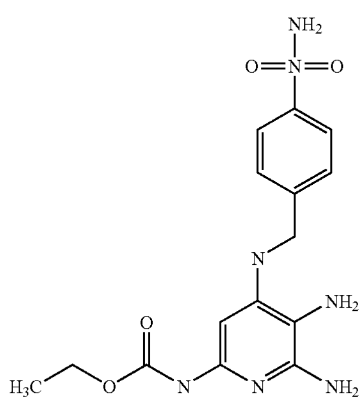 | 0 | | | |

TABLE 8-continued

| Compound # | Structure | % Inh | MIC (µg/mL) | IC50 (µg/mL) | SI |
|---|---|---|---|---|---|
| A246 | 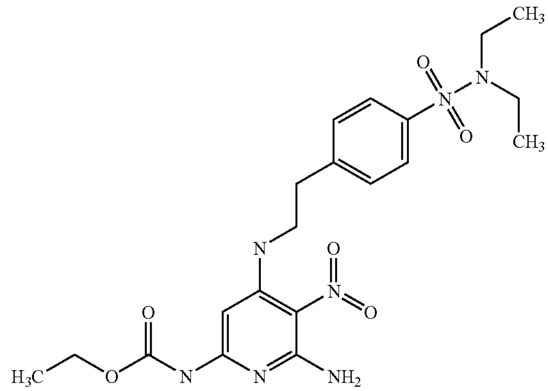 | 0 | | | |
| A247 | | 0 | | | |
| A248 | 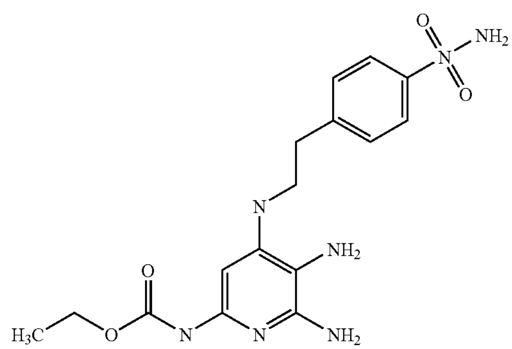 | 0 | | | |
| A249 | 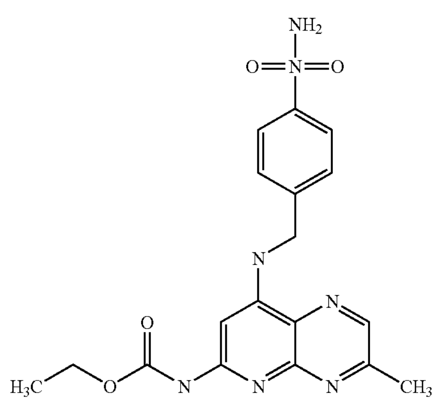 | 0 | | | |
| A250 | 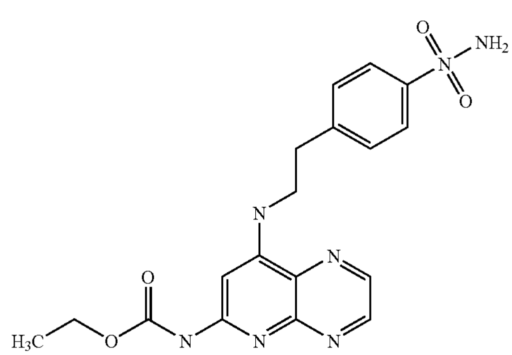 | 0 | | | |

TABLE 8-continued

| Compound # | Structure | % Inh | MIC (µg/mL) | IC50 (µg/mL) | SI |
|---|---|---|---|---|---|
| A251 | 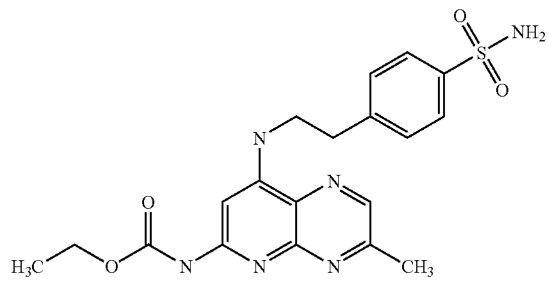 | 0 | | | |
| A252 | 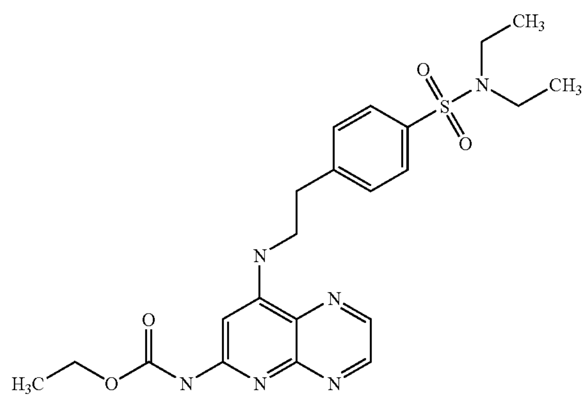 | 0 | | | |
| A253 | 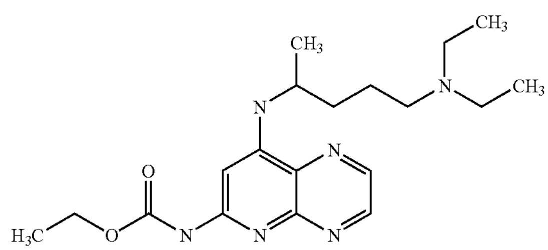 | 0 | | | |
| A254 | 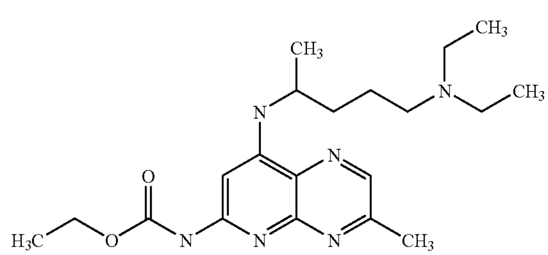 | 0 | | | |
| A255 | 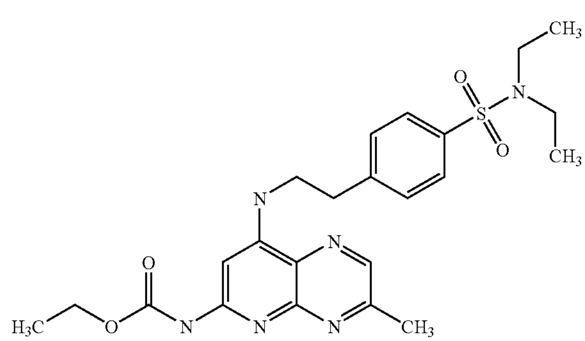 | 0 | | | |

TABLE 8-continued

| Compound # | Structure | % Inh | MIC (μg/mL) | IC50 (μg/mL) | SI |
|---|---|---|---|---|---|
| A256 | 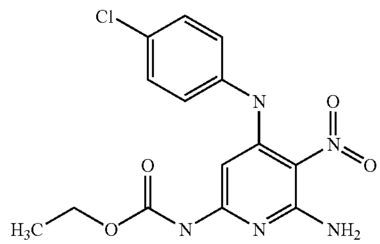 | 0 | | | |
| A257 | 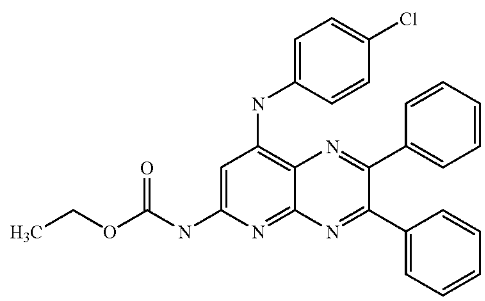 | 0 | | | |
| A258 | 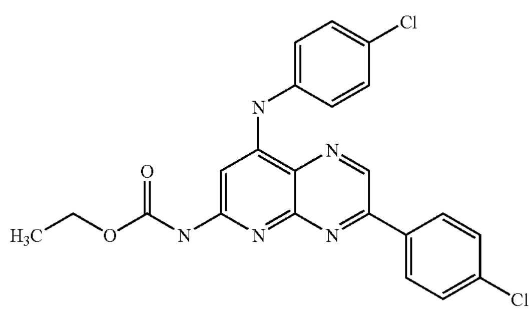 | 0 | | | |
| A259 | 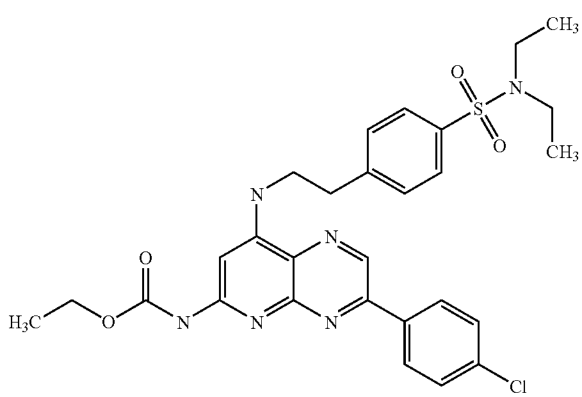 | 0 | | | |
| A260 | 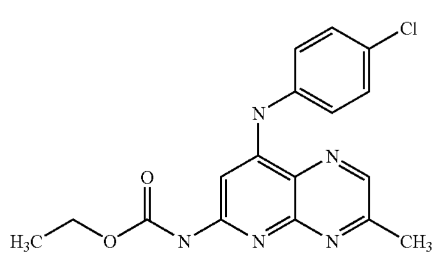 | 0 | | | |

TABLE 8-continued

| Compound # | Structure | % Inh | MIC (µg/mL) | IC50 (µg/mL) | SI |
|---|---|---|---|---|---|
| A261 | 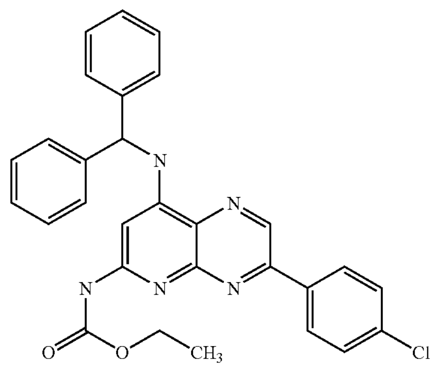 | 0 | | | |
| A262 | 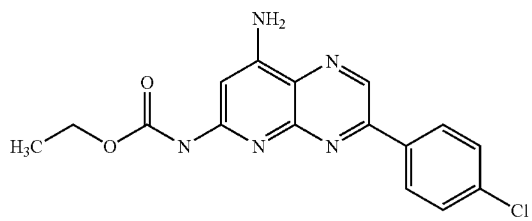 | 0 | | | |
| A263 | 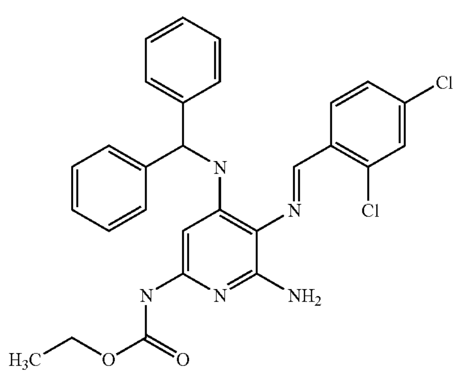 | 0 | | | |
| A264 | 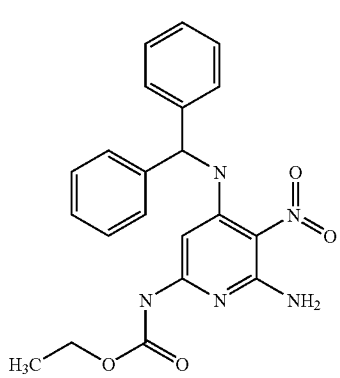 | 0 | | | |

TABLE 8-continued

| Compound # | Structure | % Inh | MIC (μg/mL) | IC50 (μg/mL) | SI |
|---|---|---|---|---|---|
| A265 | 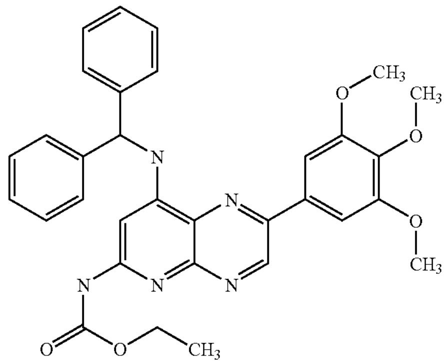 | 0 | | | |
| A266 | | 0 | | | |
| A267 | 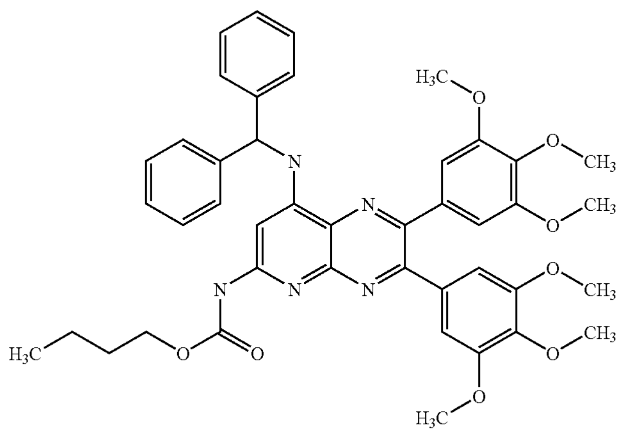 | 0 | | | |
| A268 | 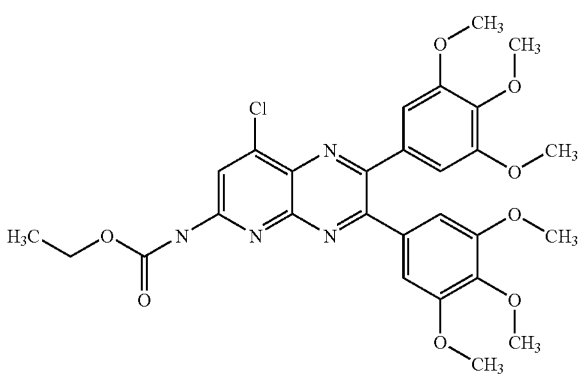 | 0 | | | |
| A269 | 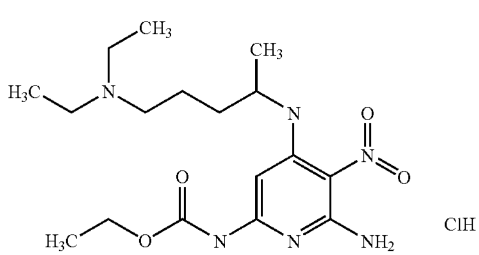 | 0 | | | |

TABLE 8-continued

| Compound # | Structure | % Inh | MIC (µg/mL) | IC50 (µg/mL) | SI |
|---|---|---|---|---|---|
| A270 | 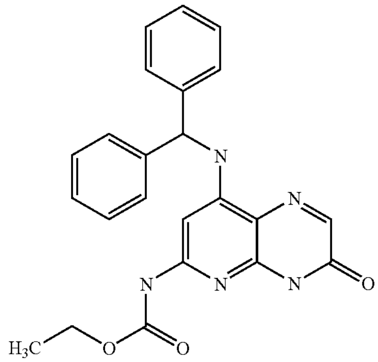 | 0 | | | |
| A271 | 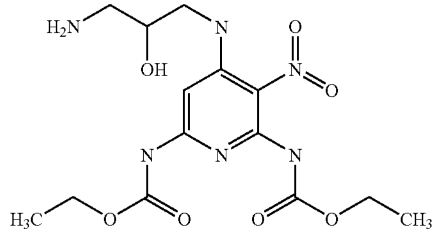 | 0 | | | |
| A272 | 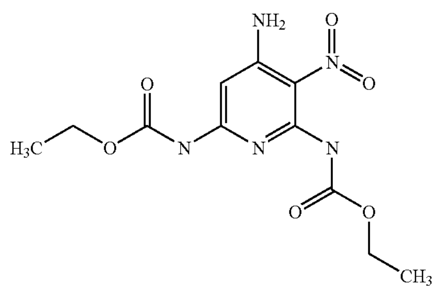 | 0 | | | |
| A273 | 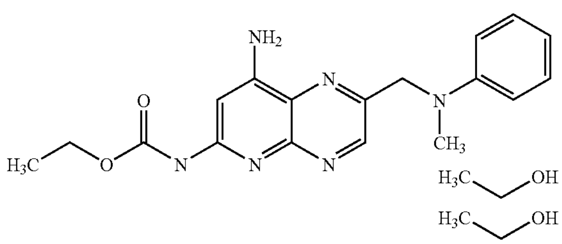 | 0 | | | |
| A274 | 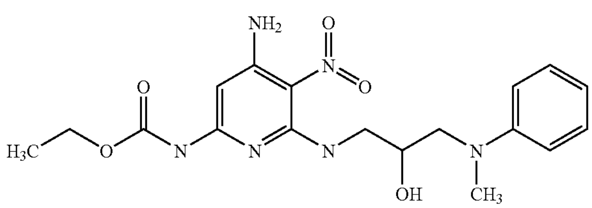 | 0 | | | |
| A275 | 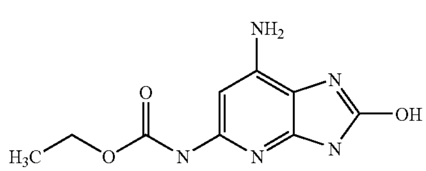 | 0 | | | |

TABLE 8-continued
| Compound # | Structure | % Inh | MIC (µg/mL) | IC50 (µg/mL) | SI |
|---|---|---|---|---|---|
| A276 | 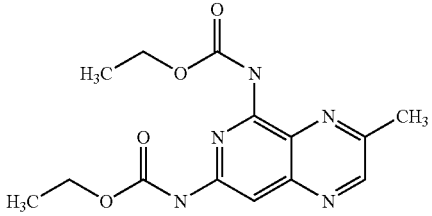 | 0 | | | |
| A277 | 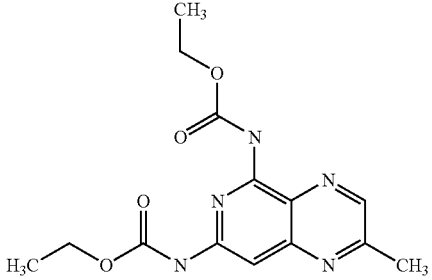 | 0 | | | |
| A278 | 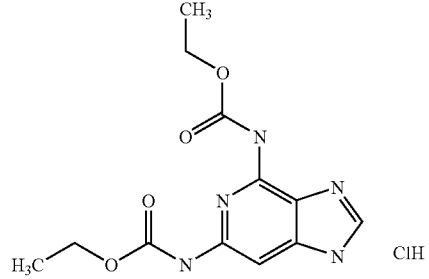 | 0 | | | |
| A279 | 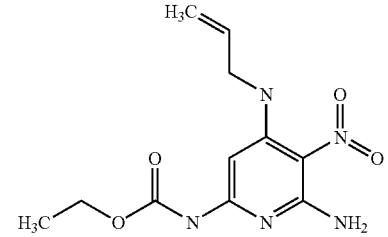 | 0 | | | |
| A280 | 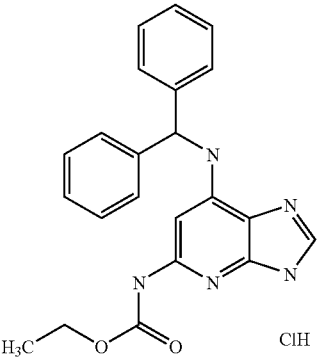 | 0 | | | |

TABLE 8-continued

| Compound # | Structure | % Inh | MIC (μg/mL) | IC50 (μg/mL) | SI |
|---|---|---|---|---|---|
| A281 | 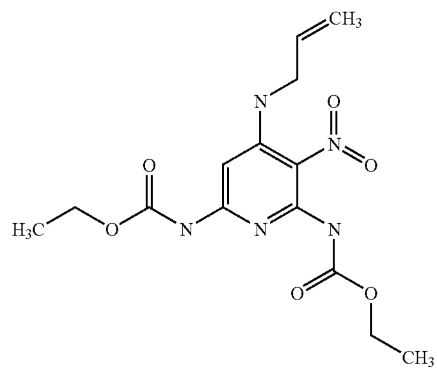 | 0 | | | |
| A282 | 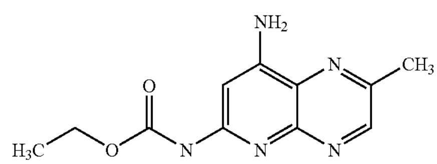 | 0 | | | |
| A283 | 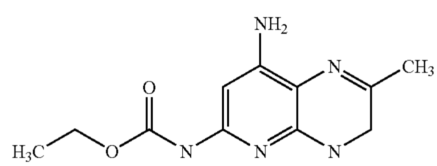 | 0 | | | |
| A284 | | 0 | | | |
| A285 | | 0 | | | |
| A286 | 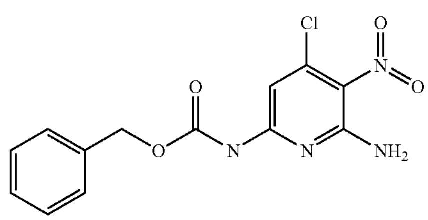 | 0 | | | |
| A287 | | 0 | | | |
| A288 | 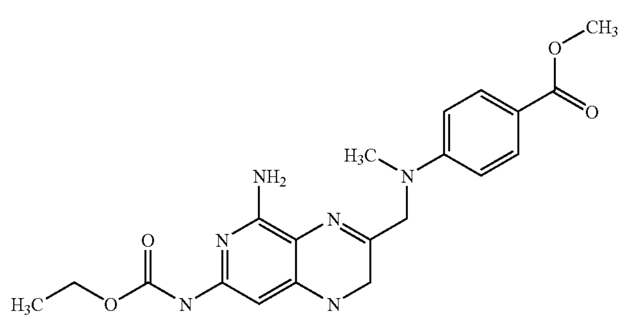 | 0 | | | |

TABLE 8-continued

| Compound # | Structure | % Inh | MIC (µg/mL) | IC50 (µg/mL) | SI |
|---|---|---|---|---|---|
| A289 | 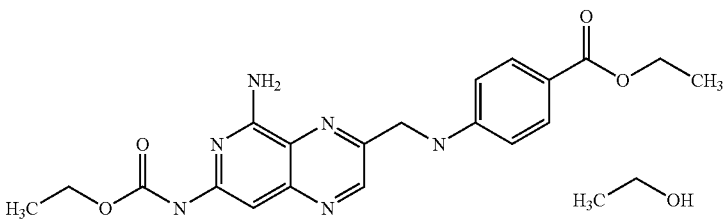 | 0 | | | |
| A290 | 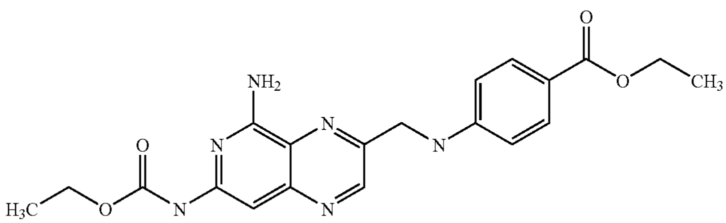 | 0 | | | |
| A291 | 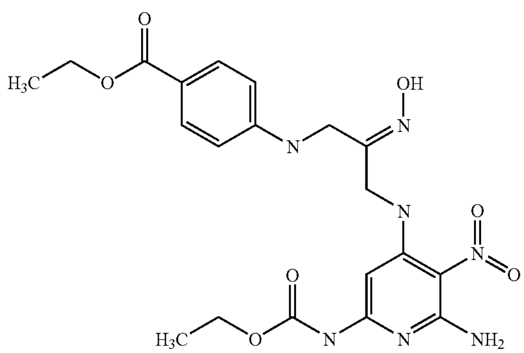 | 0 | | | |
| A292 | 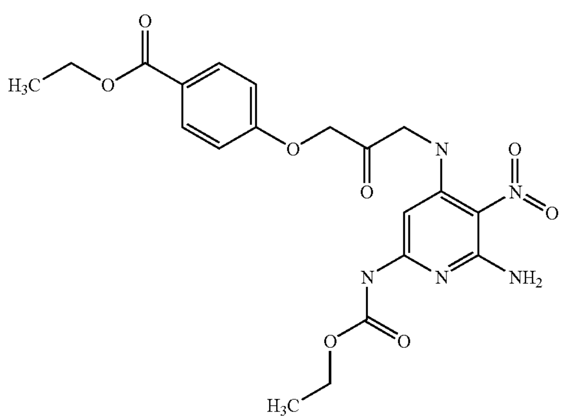 | 0 | | | |
| A293 | 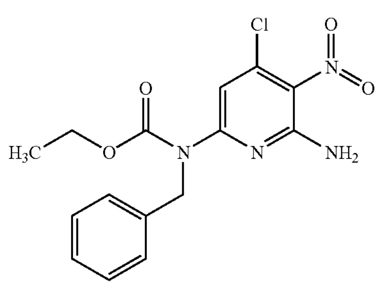 | 0 | | | |

TABLE 8-continued

| Compound # | Structure | % Inh | MIC (μg/mL) | IC50 (μg/mL) | SI |
|---|---|---|---|---|---|
| A294 | 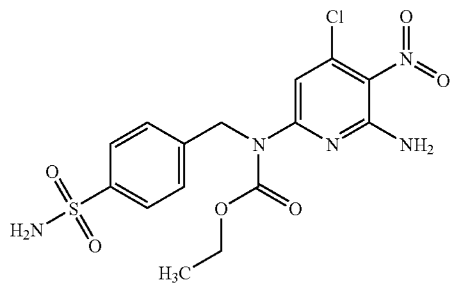 | 0 | | | |
| A295 | 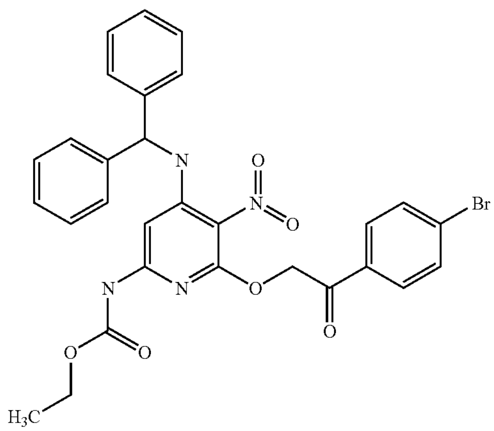 | 0 | | | |
| A296 | | 0 | | | |
| A297 | 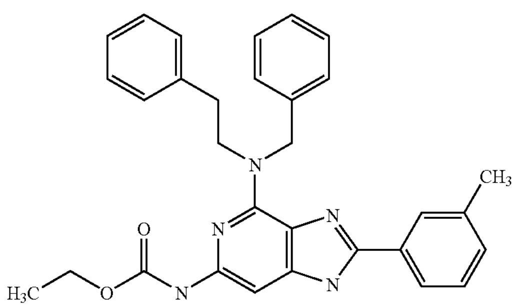 | 0 | | | |
| A298 | 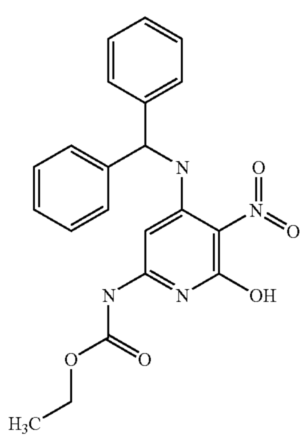 | 0 | | | |

TABLE 8-continued
| Compound # | Structure | % Inh | MIC (µg/mL) | IC50 (µg/mL) | SI |
|---|---|---|---|---|---|
| A299 | 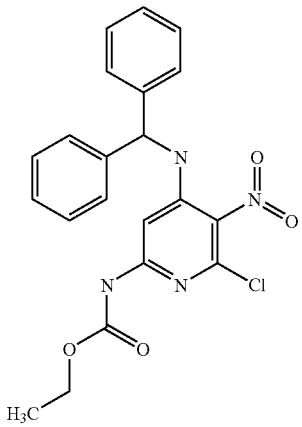 | 0 | | | |
| A300 | 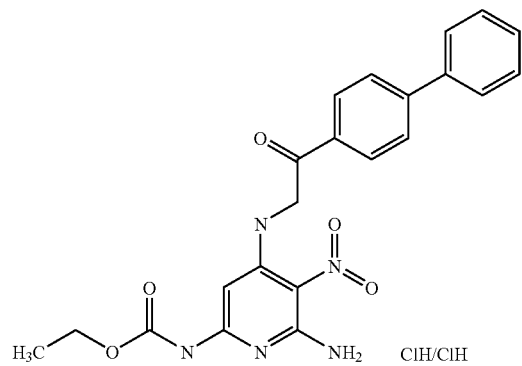 ClH/ClH | 0 | | | |
| A301 | 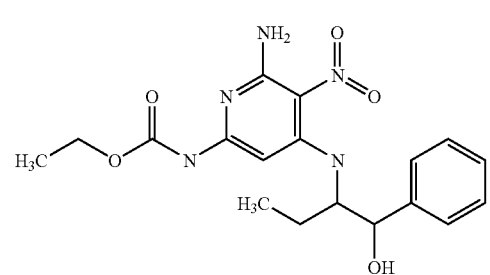 | −1 | | | |
| A302 | 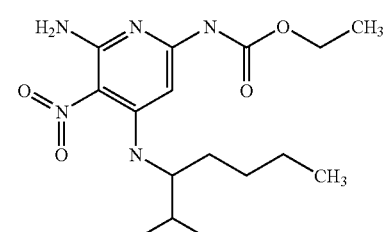 | −1 | | | |

TABLE 8-continued

| Compound # | Structure | % Inh | MIC (µg/mL) | IC50 (µg/mL) | SI |
|---|---|---|---|---|---|
| A303 | 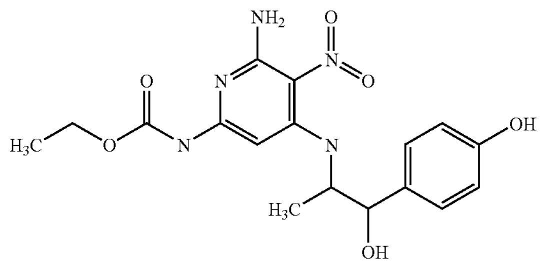 | −2 | | | |
| A304 | Chiral | −2 | | | |
| A305 | Chiral | −2 | | | |
| A306 | 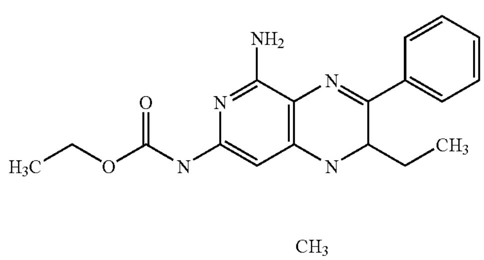 | −3 | | | |
| A307 | 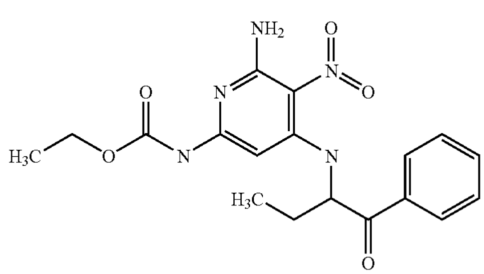 | −8 | | | |

TABLE 8-continued

| Compound # | Structure | % Inh | MIC (µg/mL) | IC50 (µg/mL) | SI |
|---|---|---|---|---|---|
| A308 | 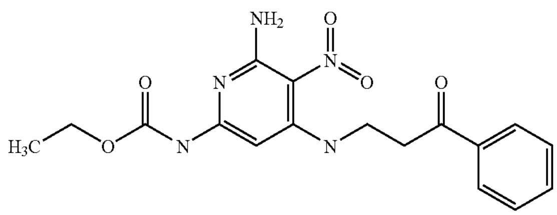 | −8 | | | |
| A309 | 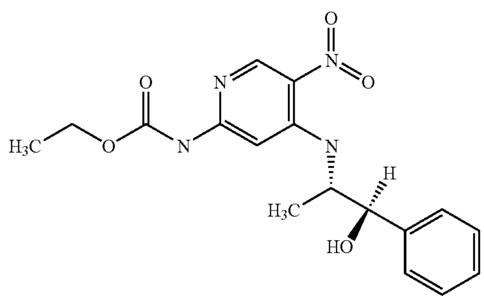 | −10 | | | |
| A310 | Chiral | −15 | | | |
| A311 | 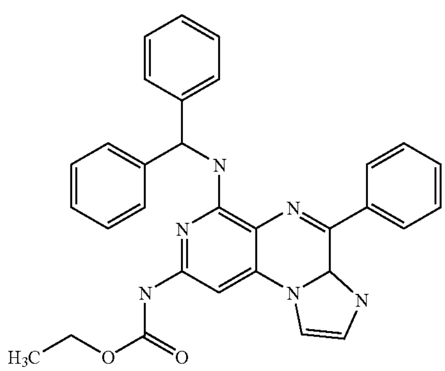 | −16 | | | |
| A312 | Chiral | −19 | | | |

TABLE 8-continued
| Compound # | Structure | % Inh | MIC (μg/mL) | IC50 (μg/mL) | SI |
|---|---|---|---|---|---|
| A313 | 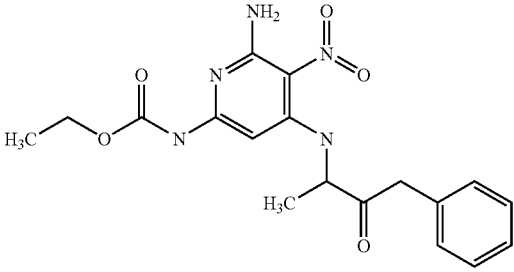 | −21 | | | |
| A314 | 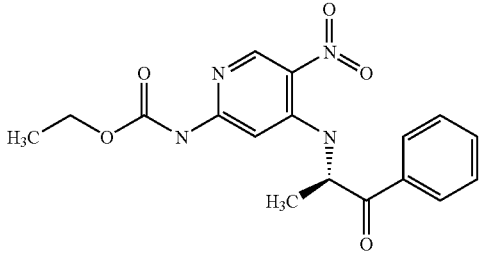 | −36 | | | |
| A315 | | | | | |
| A316 | 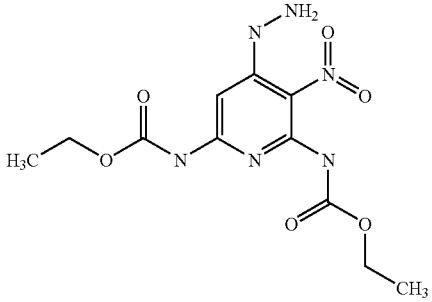 | | | | |
| A317 | 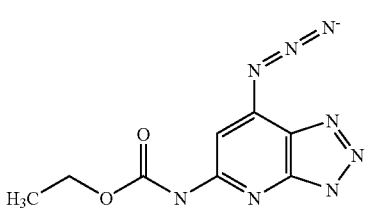 | | | | |
| A318 | 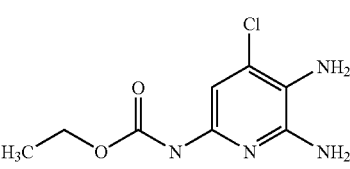 | | | | |

TABLE 8-continued

| Compound # | Structure | % Inh | MIC (μg/mL) | IC50 (μg/mL) | SI |
|---|---|---|---|---|---|
| A319 | 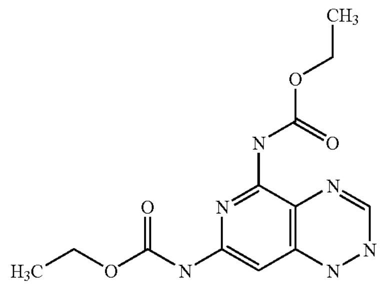 | | | | |
| A320 | 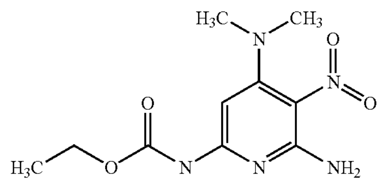 | | | | |
| A321 | 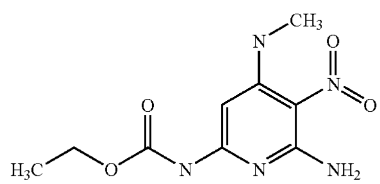 | | | | |
| A322 | 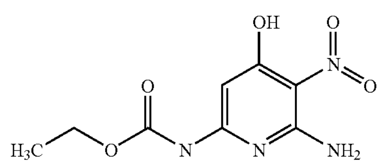 | | | | |
| A323 | 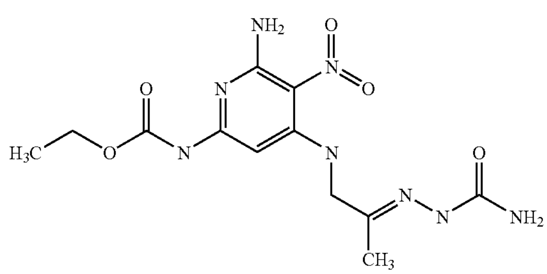 | | | | |

What is claimed is:

1. A method of inhibiting Ftsz polymerization in a bacterium comprising contacting the bacterium with an effective amount of a compound with following structure:

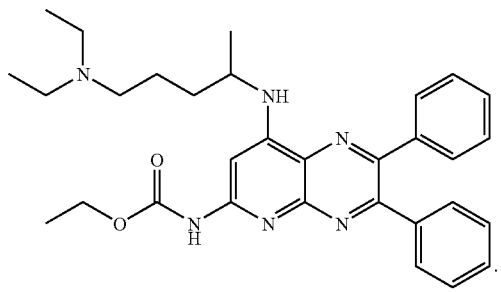

2. The method of claim 1, wherein the bacterium is a Gram positive bacterium and said bacterium is *Mycobacterium (M.) tuberculosis*.

3. The method of claim 1, wherein the compound is linked to a permeability enhancer, wherein the permeability enhancer allows the compound to cross the cell envelope of the bacterium.

4. The method of claim 3, wherein the permeability enhancer is selected from the group consisting of polymyxin B, surface active agents, defensins, other membrane active peptides and chelating agents.

5. The method of claim 1, further comprising contacting the bacterium with a permeability enhancer.

6. The method of claim 5, wherein the permeability enhancer is selected from the group consisting of polymyxin B, surface active agents, defensins, other membrane active peptides and chelating agents.

* * * * *

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence; Note = synthetic construct
<220> FEATURE:
<221> NAME/KEY: VARIANT
<222> LOCATION: 6
<223> OTHER INFORMATION: Xaa can be either Ser or Thr

```
<400> SEQUENCE: 1

Gly Gly Gly Thr Gly Xaa Gly
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Asp Ala Val Ile Lys
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Val Ala Thr Gly Ile Gly
 1               5
```